US007846964B2

(12) United States Patent
Bolli et al.

(10) Patent No.: US 7,846,964 B2
(45) Date of Patent: Dec. 7, 2010

(54) THIOPHENE DERIVATIVES AS SPINGOSINE-1-PHOSPHATE-1 RECEPTOR AGONISTS

(75) Inventors: Martin Bolli, Allschwil (CH); David Lehmann, Basel (CH); Boris Mathys, Egerkingen (CH); Claus Mueller, Weil am Rhein (DE); Oliver Nayler, Arlesheim (CH); Jorg Velker, Huningue (FR); Thomas Weller, Binningen (CH)

(73) Assignee: Actelion Pharmaceuticals Ltd., Allschwil (CH)

( * ) Notice: Subject to any disclaimer, the term of this patent is extended or adjusted under 35 U.S.C. 154(b) by 721 days.

(21) Appl. No.: 11/909,440

(22) PCT Filed: Mar. 20, 2006

(86) PCT No.: PCT/IB2006/050853

§ 371 (c)(1),
(2), (4) Date: Sep. 21, 2007

(87) PCT Pub. No.: WO2006/100635

PCT Pub. Date: Sep. 28, 2006

(65) Prior Publication Data

US 2008/0194670 A1    Aug. 14, 2008

(30) Foreign Application Priority Data

Mar. 23, 2005    (WO) ................ PCT/EP2005/003072

(51) Int. Cl.
*A61K 31/381*    (2006.01)
*C07D 333/78*    (2006.01)
(52) U.S. Cl. ........................................ 514/443; 549/43
(58) Field of Classification Search ................ 514/443; 549/43
See application file for complete search history.

(56) References Cited

U.S. PATENT DOCUMENTS

| 4,808,599 | A | 2/1989 | Dubroeucq et al. |
| 6,156,787 | A | 12/2000 | Broughton et al. |
| 2004/0058894 | A1 | 3/2004 | Doherty |
| 2008/0064740 | A1 | 3/2008 | Bolli et al. |
| 2008/0176926 | A1 | 7/2008 | Bolli et al. |
| 2008/0300294 | A1 | 12/2008 | Bolli et al. |
| 2008/0318955 | A1 | 12/2008 | Bolli et al. |
| 2009/0005421 | A1 | 1/2009 | Bolli et al. |
| 2010/0075946 | A1 | 3/2010 | Bolli et al. |

FOREIGN PATENT DOCUMENTS

| EP | 0476 646 | 6/1997 |
| WO | WO-91/15583 A1 | 10/1991 |
| WO | WO-99/46277 A1 | 9/1999 |
| WO | WO 03/062248 | 7/2003 |
| WO | WO 2004/007517 | 1/2004 |
| WO | WO 2005/014525 | 2/2005 |
| WO | WO 2005/058848 | 6/2005 |
| WO | WO-2006/010379 A1 | 2/2006 |

OTHER PUBLICATIONS

T. Hla, et al., "An Abundant Transcript Induced in Differentiating Human Endothelial Cells Encodes a Polypeptide with Structural Similiarites to G-protein-coupled Receptors," J. Biol Chem, 265 (1990), pp. 9308-9313.
Philip L. Gould, "Salt selection for basic drugs," Int. J. Pharm., 33 (1986), pp. 201-217.
Mark Gibson, Editor, Pharmaceutical Preformulation and Formulation, IHS Health Group, Englewood, CO, USA, 2001.
M. Mentzel, et al.,"N-Metroxy-N-methylamides (Weinreb Amides) in Modern Organic Synthesis," Journal fuer Praktische Chemie/ Chemiker-Zeitung 339 (1997), pp. 517-524.
J. Singh, et al., "The Growing Synthetic Utility of Weinreb's Amide," Journal fuer Praktische Chemie (Weinheim, Germany, 342 (2000), pp. 340-347.
V.K. Khlestkin, et al., "Recent Advances in the Application of N,O-Dialkylhydroxylamines in Organic Chemistry," Current Organic Chemistry 7, (2003), pp. 967-993.
T.W. Greene, et al., "Protective Groups in Organic Synthesis," 3rd Edition, Wiley New York, 1991.
P.J. Kocienski, Protecting Group, Thieme Stuttgart, 1994.
S.A. Popov, et al., "Synthesis of New Chiral Heterocycles of the Pyrazole and 2-Isoxazoline Types from (+)-3-Carene," Tetrahedron: Asymmetry, vol. 5, No. 3 (1994), pp. 479-489.
S.A. Popov, et al., "Synthesis of 2-Alkyl and 2-Aryl Pyrimidines from β-Chlorovinyl Ketones of Cyclopentanone Type," Synthetic Commmunications, 31(2), (2001), pp. 233-243.
W. Cocker, et al., "A Convenient Preparation of (−)-β-3,4-Epoxycarane," Tetrahedron Letters No. 51, (1969), pp. 4451-4452.
S. Lochynski, et al., "Modification of Synthesis of Dihydrochrysanthemolactone from (+)-Car-3-ene," J. Prakt. Chem. (Leipzig) 330 (1988), pp. 284-288.
M. Walkowicz, et al., "Uber Stereoisomere 6,6-Dimethyl-Bicyclo-[3.1.0]-Hexanole-3," Roczniki Chemii Ann. Soc. Chim. Polonorum 41(1967) pp. 927-937.
H. Kuczynski, et al., "O Krystalicznym (−)-Dwubromo-3,4-Karanie," Roczniki Chemii Ann. Soc. Chim. Polonorum 38, (1964), pp. 1625-1633.
A.V. Pol, et al., "Oxidation of Δ$^3$-Carene & α-Pinene with Thallium(III) Nitrate," Indian J. Chem., Sect. B, vol. 19B, (1980) pp. 603-604.
G. Trapani, et al., "Propofol Analogues. Synthesis, Relationships between Structure and Affinity at GABA$_A$ Receptor in Rat Brain and Differential Electrophysiological Profile at Recombinant Human GABA$_A$ Receptors," J. Med. Chem. 41 (1998) pp. 1846-1854.
G.G. Ecke, et al., "ortho-Alkylation of Aromatic Amines," J. Org. Chem., vol. 22, (1957) pp. 639-642.
V.M. Christl, et al., "Einige Valene von Benzanellierten fuenfgliedrigen Hetroarenen-Synthesen und NMR-Spektren," Angewandte Chemie VCH Verlagsgesellschaft, Weinheim, DE, vol. 102 , No. 6 (1990) pp. 704-706.

*Primary Examiner*—Taofiq A Solola
(74) *Attorney, Agent, or Firm*—Hoxie & Associates LLC

(57) ABSTRACT

The invention relates to novel thiophene derivatives, their preparation and their use as pharmaceutically active compounds. Said compounds particularly act as immunosuppressive agents.

22 Claims, No Drawings

THIOPHENE DERIVATIVES AS SPINGOSINE-1-PHOSPHATE-1 RECEPTOR AGONISTS

FIELD OF THE INVENTION

The present invention relates to S1P1/EDG1 receptor agonists of Formula (I) and their use as active ingredients in the preparation of pharmaceutical compositions. The invention also concerns related aspects including processes for the preparation of the compounds, pharmaceutical compositions containing a compound of the Formula (I), and their use as compounds improving vascular function and as immunomodulating agents, either alone or in combination with other active compounds or therapies.

BACKGROUND OF THE INVENTION

The human immune system is designed to defend the body against foreign micro-organisms and substances that cause infection or disease. Complex regulatory mechanisms ensure that the immune response is targeted against the intruding substance or organism and not against the host. In some cases, these control mechanisms are unregulated and autoimmune responses can develop. A consequence of the uncontrolled inflammatory response is severe organ, cell, tissue or joint damage. With current treatment, the whole immune system is usually suppressed and the body's ability to react to infections is also severely compromised. Typical drugs in this class include azathioprine, chlorambucil, cyclophosphamide, cyclosporin, or methotrexate. Corticosteroids which reduce inflammation and suppress the immune response, may cause side effects when used in long term treatment. Nonsteroidal anti-infammatory drugs (NSAIDs) can reduce pain and inflammation, however, they exhibit considerable side effects. Alternative treatments include agents that activate or block cytokine signaling.

Orally active compounds with immunomodulating properties, without compromising immune responses and with reduced side effects would significantly improve current treatments of uncontrolled inflammatory disease.

In the field of organ transplantation the host immune response must be suppressed to prevent organ rejection. Organ transplant recipients can experience some rejection even when they are taking immunosuppressive drugs. Rejection occurs most frequently in the first few weeks after transplantation, but rejection episodes can also happen months or even years after transplantation. Combinations of up to three or four medications are commonly used to give maximum protection against rejection while minimizing side effects. Current standard drugs used to treat the rejection of transplanted organs interfere with discrete intracellular pathways in the activation of T-type or B-type white blood cells. Examples of such drugs are cyclosporin, daclizumab, basiliximab, everolimus, or FK506, which interfere with cytokine release or signaling; azathioprine or leflunomide, which inhibit nucleotide synthesis; or 15-deoxyspergualin, an inhibitor of leukocyte differentiation.

The beneficial effects of broad immunosuppressive therapies relate to their effects; however, the generalized immunosuppression which these drugs produce diminishes the immune system's defense against infection and malignancies. Furthermore, standard immunosuppressive drugs are often used at high dosages and can cause or accelerate organ damage.

DESCRIPTION OF THE INVENTION

The present invention provides novel compounds of Formula (I) that are agonists for the G protein-coupled receptor S1P1/EDG1 and have a powerful and long-lasting immunosuppressive effect which is achieved by reducing the number of circulating and infiltrating T- and B-lymphocytes, without affecting their maturation, memory, or expansion. The reduction of circulating T-/B-lymphocytes as a result of S1P1/EDG1 agonism, possibly in combination with the observed improvement of endothelial cell layer function associated with S1P1/EDG1 activation, makes such compounds useful to treat uncontrolled inflammatory disease and to improve vascular functionality.

The compounds of the present invention can be utilized alone or in combination with standard drugs inhibiting T-cell activation, to provide a new immunosuppressive therapy with a reduced propensity for infections when compared to standard immunosuppressive therapy. Furthermore, the compounds of the present invention can be used in combination with reduced dosages of traditional immunosuppressant therapies, to provide on the one hand effective immunosuppressive activity, while on the other hand reducing end organ damage associated with higher doses of standard immunosuppressive drugs. The observation of improved endothelial cell layer function associated with S1P1/EDG1 activation provides additional benefits of compounds to improve vascular function.

The nucleotide sequence and the amino acid sequence for the human S1P1/EDG1 receptor are known in the art and are published in e.g.: Hla, T., and Maciag, T. *J. Biol Chem.* 265 (1990), 9308-9313; WO 91/15583 published 17 Oct. 1991; WO 99/46277 published 16 Sep. 1999. The potency and efficacy of the compounds of Formula (I) are assessed using a GTPγS assay to determine $EC_{50}$ values and by measuring the circulating lymphocytes in the rat after oral administration, respectively (see Examples).

The following paragraphs provide definitions of the various chemical moieties that make up the compounds according to the invention and are intended to apply uniformly throughout the specification and claims unless an otherwise expressly set out definition provides a broader definition.

The term $C_{1-5}$-alkyl, alone or in combination with other groups, means saturated, branched or preferably straight chain groups with one to five carbon atoms, preferably one to three carbon atoms. Examples of $C_{1-5}$-alkyl groups are methyl, ethyl, n-propyl, iso-propyl, n-butyl, iso-butyl, sec-butyl, tert-butyl, and n-pentyl.

The term $C_{1-5}$-alkoxy, alone or in combination with other groups, means an R—O group, wherein R is a $C_{1-5}$-alkyl. Preferred examples of $C_{1-5}$-alkoxy groups are methoxy, ethoxy, propoxy, iso-propoxy, iso-butoxy, sec-butoxy and tert-butoxy.

The term $C_{1-5}$-alkylamino or di-($C_{1-5}$-alkyl)amino, alone or in combination with other groups, means an R'—NH— or an R'—NR"— group, respectively, wherein R' and R" are each independently a $C_{1-5}$-alkyl group. Preferred examples of $C_{1-5}$-alkylamino or di-($C_{1-5}$-alkyl)amino groups are methylamino, ethylamino, N,N-dimethylamino, and N-methyl-N-ethyl-amino.

The term halogen means fluoro, chloro, bromo or iodo, preferably fluoro or chloro.

If the group A of Formula (I) represents an asymmetric bivalent group, such a group is connected in a way that the beginning part of the group A is linked to the carbonyl group of Formula (I) (that means that for example the —NH part of —NH—CH$_2$— is linked to the carbonyl group of Formula (I)).

Where the plural form is used for compounds, salts, pharmaceutical compositions, diseases and the like, this is intended to mean also a single compound, salt, or the like.

Any reference hereinbefore or hereinafter to a compound of Formula (I) is to be understood as referring also to configurational isomers such as optically pure enantiomers, mixtures of enantiomers such as racemates, diastereomers, mixtures of diastereomers, diastereomeric racemates, and mixtures of diastereomeric racemates, as well as salts (especially pharmaceutically acceptable salts) and solvent complexes (including hydrates) of such compounds, and morphological forms, as appropriate and expedient.

Salts are preferably the pharmaceutically acceptable salts of the compounds of Formula (I).

Salt-forming groups are groups or radicals having basic or acidic properties. Compounds having at least one basic group or at least one basic radical, for example amino, a secondary amino group not forming a peptide bond or a pyridyl radical, may form acid addition salts, for example with inorganic acids. When several basic groups are present mono- or polyacid addition salts may be formed.

Compounds having acidic groups, such as a carboxy group or a phenolic hydroxy group, may form metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri-(2-hydroxyethyl)-amine, or heterocyclic bases, for example N-ethyl-piperidine or N,N'-dimethylpiperazine. Mixtures of salts are possible.

Compounds having both acidic and basic groups can form internal salts.

For the purposes of isolation or purification, as well as in the case of compounds that are used further as intermediates, it is also possible to use pharmaceutically unacceptable salts, e.g. the picrates. Only pharmaceutically acceptable, non-toxic salts may be used for therapeutic purposes, however, and those salts are therefore preferred.

The expression pharmaceutically acceptable salts encompasses either salts with inorganic acids or organic acids like hydrochloric acid, hydrobromic acid, hydroiodic acid, sulfuric acid, sulfamic acid, phosphoric acid, nitric acid, phosphorous acid, nitrous acid, citric acid, formic acid, acetic acid, oxalic acid, maleic acid, lactic acid, tartaric acid, fumaric acid, benzoic acid, mandelic acid, cinnamic acid, pamoic acid, stearic acid, glutamic acid, aspartic acid, methanesulfonic acid, ethanedisulfonic acid, p-toluenesulfonic acid, salicylic acid, succinic acid, trifluoroacetic acid, and the like that are non toxic to living organisms or in case the compound of Formula (I) is acidic in nature with an inorganic base like an alkali or earth alkali base, e.g. sodium hydroxide, potassium hydroxide, calcium hydroxide and the like. For other examples of pharmaceutically acceptable salts, reference can be made to "Salt selection for basic drugs", *Int. J. Pharm.* (1986), 33, 201-217.

The compounds of the Formula (I) may contain asymmetric carbon atoms. Substituents at a double bond or a ring may be present in cis-(=Z—) or trans (=E-) form unless indicated otherwise. The compounds of Formula (I) may thus be present as mixtures of stereoisomers or preferably as pure stereoisomers. Mixtures of stereoisomers may be separated in a manner known per se, e.g. by column chromatography, thin layer chromatography, HPLC or crystallization.

i) The invention relates to novel thiophene compounds of the Formula (I),

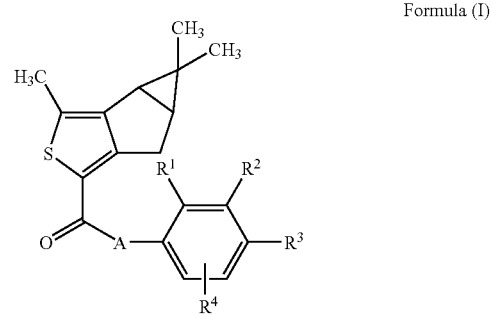

Formula (I)

wherein
A represents —CH$_2$CH$_2$—, —CH=CH—, —NH—CH$_2$—, —CH$_2$—O—, or —CH$_2$—NH—;
R$^1$ represents hydrogen, C$_{1-5}$-alkyl, C$_{1-5}$-alkoxy, or halogen;
R$^2$ represents hydrogen, C$_{1-5}$-alkyl, C$_{1-5}$-alkoxy, trifluoromethyl, trifluoromethoxy, or halogen;
R$^3$ represents 2,3-dihydroxypropyl, —CH$_2$—(CH$_2$)$_k$—NR$^{31}$R$^{32}$, (azetidine-3-carboxylic acid)-1-yl-methyl, (azetidine-3-carboxylic acid C$_{1-5}$-alkylester)-1-yl-methyl, 2-[(azetidine-3-carboxylic acid)-1-yl]-ethyl, 2-[(azetidine-3-carboxylic acid C$_{1-5}$-alkylester)-1-yl]-ethyl, 3-[(azetidine-3-carboxylic acid)-1-yl]-propyl, 3-[(azetidine-3-carboxylic acid C$_{1-5}$-alkylester)-1-yl]-propyl, (pyrrolidine-3-carboxylic acid)-1-yl-methyl, (pyrrolidine-3-carboxylic acid C$_{1-5}$-alkylester)-1-yl-methyl, (pyrrolidine-2-carboxylic acid)-1-yl-methyl, (pyrrolidine-2-carboxylic acid C$_{1-5}$-alkylester)-1-yl-methyl, 2-[(pyrrolidine-3-carboxylic acid)-1-yl]-ethyl, 2-[(pyrrolidine-3-carboxylic acid C$_{1-5}$-alkylester)-1-yl]-ethyl, 2-[(pyrrolidine-2-carboxylic acid)-1-yl]-ethyl, 2-[(pyrrolidine-2-carboxylic acid C$_{1-5}$-alkylester)-1-yl]-ethyl, 3-[(pyrrolidine-3-carboxylic acid)-1-yl]-propyl, 3-[(pyrrolidine-3-carboxylic acid C$_{1-5}$-alkylester)-1-yl]-propyl, 3-[(pyrrolidine-2-carboxylic acid)-1-yl]-propyl, 3-[(pyrrolidine-2-carboxylic acid C$_{1-5}$-alkylester)-1-yl]-propyl, —CH$_2$-(CH$_2$)$_n$—COOH, —CH$_2$—(CH$_2$)$_n$—CONR$^{31}$R$^{32}$, —CO—NHR$^{31}$, 1-(1-(3-carboxy-azetidinyl))-2-acetyl, 1-(1-(2-carboxy-pyrrolidinyl))-2-acetyl, 1-(1-(3-carboxy-pyrrolidinyl))-2-acetyl, 1-(1-(3-carboxy-azetidinyl))-3-propionyl, 1-(1-(2-carboxy-pyrrolidinyl))-3-propionyl, 1-(1-(3-carboxy-pyrrolidinyl))-3-propionyl, —(CH$_2$)$_n$CH(OH)—CH$_2$—NR$^{31}$R$^{32}$, 2-hydroxy-3-methoxy-propoxy, —OCH$_2$—(CH$_2$)$_m$—NR$^{31}$R$^{32}$, 2-pyrrolidin-1-yl-ethoxy, 3-pyrrolidin-1-yl-propoxy, 2-piperazin-1-yl-ethoxy, 2-[4-(C$_{1-5}$-alkyl)-piperazin-1-yl]-ethoxy, 2-[4-(2-hydroxy-ethyl)-piperazin-1-yl]-ethoxy, 3-piperazin-1-yl-propoxy, 3-[4-(C$_{1-5}$-alkyl)-piperazin-1-yl]-propoxy, 3-[4-(2-hydroxy-ethyl)-piperazin-1-yl]-propoxy, 2-morpholin-4-yl-ethoxy, 3-morpholin-4-yl-propoxy, 2-[(azetidine-3-carboxylic acid)-1-yl]-ethoxy, 2-[(azetidine-3-carboxylic acid C$_{1-5}$-alkylester)-1-yl]-ethoxy, 2-[(pyrrolidine-3-carboxylic acid)-1-yl]-ethoxy, 2-[(pyrrolidine-3-carboxylic acid C$_{1-5}$-alkylester)-1-yl]-ethoxy, 2-[(pyrrolidine-2-carboxylic acid)-1-yl]-ethoxy, 2-[(pyrrolidine-2-carboxylic acid C$_{1-5}$-alkylester)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid $C_{1-5}$-alkylester)-1-yl]-propoxy, 3-[(pyrrolidine-3-carboxylic acid)-1-yl]-propoxy, 3-[(pyrrolidine-3-carboxylic acid $C_{1-5}$-alkylester)-1-yl]-propoxy, 3-[(pyrrolidine-2-carboxylic acid)-1-yl]-propoxy, 3-[(pyrrolidine-2-carboxylic acid $C_{1-5}$-alkylester)-1-yl]-propoxy, 3-[(2-hydroxy-pyrrolidine)-1-yl]-propoxy, 3-[(3-hydroxy-pyrrolidine)-1-yl]-propoxy, —O—CH$_2$—CONR$^{31}$R$^{32}$, 1-(1-(3-carboxy-azetidinyl))-1-oxo-2-ethoxy, 1-(1-(pyrrolidine-2-carboxylic acid)-1-yl)-1-oxo-2-ethoxy, 1-(1-(pyrrolidine-3-carboxylic acid)-1-yl)-1-oxo-2-ethoxy, 3-carbamoyl-propoxy, 3-($C_{1-5}$-alkylcarbamoyl)propoxy, 3-(2-hydroxyethylcarbamoyl)propoxy, —OCH$_2$—CH(OH)—CH$_2$—NR$^{31}$R$^{32}$, 3-[(azetidine-3-carboxylic acid)-1-yl]-2-hydroxypropoxy, 3-[(azetidine-3-carboxylic acid $C_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid $C_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid $C_{1-5}$-alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-($C_{1-5}$-alkyl)-piperazin-1-yl]-propoxy, 2-hydroxy-3-[4-(2-hydroxy-ethyl)-piperazin-1-yl]-propoxy, 2-hydroxy-3-morpholin-4-yl-propoxy, —NR$^{31}$R$^{32}$, —NHCO—R$^{31}$, —CH$_2$—(CH$_2$)$_k$—NHSO$_2$R$^{33}$, —(CH$_2$)$_n$CH(OH)—CH$_2$—NHSO$_2$R$^{33}$, —OCH$_2$—(CH$_2$)$_m$—NHSO$_2$R$^{33}$, —OCH$_2$—CH(OH)—CH$_2$—NHSO$_2$R$^{33}$, —CH$_2$—(CH$_2$)$_k$—NHCOR$^{34}$, —(CH$_2$)$_n$CH(OH)—CH$_2$—NHCOR$^{34}$, —OCH$_2$—(CH$_2$)$_m$—NHCOR$^{34}$, or —OCH$_2$—CH(OH)—CH$_2$—NHCOR$^{34}$;

R$^{31}$ represents hydrogen, methyl, ethyl, n-propyl, isopropyl, 2-hydroxyethyl, 2-hydroxy-1-hydroxymethyl-ethyl, 2-$C_{1-5}$-alkoxyethyl, 3-hydroxypropyl, 3-$C_{1-5}$-alkoxypropyl, 2-aminoethyl, 2-($C_{1-5}$-alkylamino)ethyl, 2-(di-($C_{1-5}$-alkyl)amino)ethyl, carboxymethyl, $C_{1-5}$-alkylcarboxymethyl, 2-carboxyethyl, or 2-($C_{1-5}$-alkylcarboxy)ethyl;

R$^{32}$ represents hydrogen, methyl, or ethyl;

R$^{33}$ represents methyl, ethyl, propyl, isopropyl, butyl, 2-hydroxyethyl, 2-methoxyethyl, methylamino, ethylamino, propylamino, isopropylamino, n-butylamino, or dimethylamino;

R$^{34}$ represents hydroxymethyl, hydroxyethyl, aminomethyl, methylaminomethyl, dimethylaminomethyl, aminoethyl, 2-methylamino-ethyl, or 2-dimethylamino-ethyl;

k represents the integer 1, 2, or 3;

m represents the integer 1 or 2;

n represents 0, 1, or 2; and

R$^4$ represents hydrogen, $C_{1-5}$-alkyl, methoxy or halogen;

and configurational isomers such as optically pure enantiomers, mixtures of enantiomers such as racemates, diastereomers, mixtures of diastereomers, diastereomeric racemates, and mixtures of diastereomeric racemates, as well as salts and solvent complexes of such compounds, and morphological forms.

ii) A particular embodiment of the invention relates to thiophene derivatives according to embodiment i), wherein R$^3$ represents 2,3-dihydroxypropyl, —CH$_2$—(CH$_2$)$_k$—NR$^{31}$R$^{32}$, (azetidine-3-carboxylic acid)-1-yl-methyl, (azetidine-3-carboxylic acid $C_{1-5}$-alkylester)-1-yl-methyl, 2-[(azetidine-3-carboxylic acid)-1-yl]-ethyl, 2-[(azetidine-3-carboxylic acid $C_{1-5}$-alkylester)-1-yl]-ethyl, 3-[(azetidine-3-carboxylic acid)-1-yl]-propyl, 3-[(azetidine-3-carboxylic acid $C_{1-5}$-alkylester)-1-yl]-propyl, (pyrrolidine-3-carboxylic acid)-1-yl-methyl, (pyrrolidine-3-carboxylic acid $C_{1-5}$-alkylester)-1-yl-methyl, (pyrrolidine-2-carboxylic acid)-1-yl-methyl, (pyrrolidine-2-carboxylic acid $C_{1-5}$-alkylester)-1-yl-methyl, 2-[(pyrrolidine-3-carboxylic acid)-1-yl]-ethyl, 2-[(pyrrolidine-3-carboxylic acid $C_{1-5}$-alkylester)-1-yl]-ethyl, 2-[(pyrrolidine-2-carboxylic acid)-1-yl]-ethyl, 2-[(pyrrolidine-2-carboxylic acid $C_{1-5}$-alkylester)-1-yl]-ethyl, 3-[(pyrrolidine-3-carboxylic acid)-1-yl]-propyl, 3-[(pyrrolidine-3-carboxylic acid $C_{1-5}$-alkylester)-1-yl]-propyl, 3-[(pyrrolidine-2-carboxylic acid)-1-yl]-propyl, 3-[(pyrrolidine-2-carboxylic acid $C_{1-5}$-alkylester)-1-yl]-propyl, —CH$_2$—(CH$_2$)$_n$—CONR$^{31}$R$^{32}$, —CO—NHR$^{31}$, 1-(1-(3-carboxy-azetidinyl))-2-acetyl, 1-(1-(2-carboxy-pyrrolidinyl))-2-acetyl, 1-(1-(3-carboxy-pyrrolidinyl))-2-acetyl, 1-(1-(3-carboxy-azetidinyl))-3-propionyl, 1-(1-(2-carboxy-pyrrolidinyl))-3-propionyl, 1-(1-(3-carboxy-pyrrolidinyl))-3-propionyl, —(CH$_2$)$_n$CH(OH)—CH$_2$—NR$^{31}$R$^{32}$, 2-hydroxy-3-methoxy-propoxy, —OCH$_2$—(CH$_2$)$_m$—NR$^{31}$R$^{32}$, 2-pyrrolidin-1-yl-ethoxy, 3-pyrrolidin-1-yl-propoxy, 2-piperazin-1-yl-ethoxy, 2-[4-($C_{1-5}$-alkyl)-piperazin-1-yl]-ethoxy, 2-[4-(2-hydroxy-ethyl)-piperazin-1-yl]-ethoxy, 3-piperazin-1-yl-propoxy, 3-[4-($C_{1-5}$-alkyl)-piperazin-1-yl]-propoxy, 3-[4-(2-hydroxy-ethyl)-piperazin-1-yl]-propoxy, 2-morpholin-4-yl-ethoxy, 3-morpholin-4-yl-propoxy, 2-[(azetidine-3-carboxylic acid)-1-yl]-ethoxy, 2-[(azetidine-3-carboxylic acid $C_{1-5}$-alkylester)-1-yl]-ethoxy, 2-[(pyrrolidine-3-carboxylic acid)-1-yl]-ethoxy, 2-[(pyrrolidine-3-carboxylic acid $C_{1-5}$-alkylester)-1-yl]-ethoxy, 2-[(pyrrolidine-2-carboxylic acid)-1-yl]-ethoxy, 2-[(pyrrolidine-2-carboxylic acid $C_{1-5}$-alkylester)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid $C_{1-5}$-alkylester)-1-yl]-propoxy, 3-[(pyrrolidine-3-carboxylic acid)-1-yl]-propoxy, 3-[(pyrrolidine-3-carboxylic acid $C_{1-5}$-alkylester)-1-yl]-propoxy, 3-[(pyrrolidine-2-carboxylic acid)-1-yl]-propoxy, 3-[(pyrrolidine-2-carboxylic acid $C_{1-5}$-alkylester)-1-yl]-propoxy, 3-[(2-hydroxy-pyrrolidine)-1-yl]-propoxy, 3-[(3-hydroxy-pyrrolidine)-1-yl]-propoxy, —O—CH$_2$—CONR$^{31}$R$^{32}$, 1-(1-(3-carboxy-azetidinyl))-1-oxo-2-ethoxy, 1-(1-(pyrrolidine-2-carboxylic acid)-1-yl)-1-oxo-2-ethoxy, 1-(1-(pyrrolidine-3-carboxylic acid)-1-yl)-1-oxo-2-ethoxy, 3-carbamoyl-propoxy, 3-($C_{1-5}$-alkylcarbamoyl)propoxy, 3-(2-hydroxyethylcarbamoyl)propoxy, —OCH$_2$—CH(OH)—CH$_2$—NR$^{31}$R$^{32}$, 3-[(azetidine-3-carboxylic acid)-1-yl]-2-hydroxypropoxy, 3-[(azetidine-3-carboxylic acid $C_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid $C_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid $C_{1-5}$-alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-($C_{1-5}$-alkyl)-piperazin-1-yl]-propoxy, 2-hydroxy-3-[4-(2-hydroxy-ethyl)-piperazin-1-yl]-propoxy, 2-hydroxy-3-morpholin-4-yl-propoxy, —NR$^{31}$R$^{32}$, —NHCO—R$^{31}$, —CH$_2$—(CH$_2$)$_k$—NHSO$_2$R$^{33}$, —(CH$_2$)$_n$CH(OH)—CH$_2$—NHSO$_2$R$^{33}$—OCH$_2$—(CH$_2$)$_m$—NHSO$_2$R$^{33}$—OCH$_2$—CH(OH)—CH$_2$—NHSO$_2$R$^{33}$, —CH$_2$—(CH$_2$)$_k$—NHCOR$^{34}$, —(CH$_2$)$_n$CH(OH)—CH$_2$—NHCOR$^{34}$, —OCH$_2$—(CH$_2$)$_m$—NHCOR$^{34}$, or —OCH$_2$—CH(OH)—CH$_2$—NHCOR$^{34}$ wherein R$^{31}$, R$^{32}$, R$^{33}$ and R$^{34}$ are as defined above in embodiment i), and R$^4$ represents hydrogen, $C_{1-5}$-alkyl or halogen.

iii) Another particular embodiment of the invention relates to thiophene derivatives according to embodiment i) or ii), wherein the compounds represented in Formula (I) constitute the (1aS,5aR)-isomer of the 1,1,2-trimethyl-1,1a,5,5a-tetrahydro-3-thia-cyclopropa[a]pentalene derivative.

iv) A preferred embodiment of the invention relates to thiophene derivatives according to any one of embodiments i) to iii), wherein A represents —$CH_2$—$CH_2$—.

v) A particular embodiment of the invention relates to thiophene derivatives according to any one of embodiments i) to iii), wherein A represents —NH—$CH_2$—.

vi) Another particular embodiment of the invention relates to thiophene derivatives according to any one of embodiments i) to iii), wherein A represents —$CH_2$—O—.

vii) A further preferred embodiment of the invention relates to thiophene derivatives according to any one of embodiments i) to vi), wherein $R^1$ represents hydrogen, and $R^2$ and $R^4$ represent a methyl group.

viii) Another further preferred embodiment of the invention relates to thiophene derivatives according to any one of embodiments i) to vii), wherein $R^4$ is in the ortho-position with respect to $R^3$.

ix) Another further preferred embodiment of the invention relates to thiophene derivatives according to any one of embodiments i) to vi), wherein $R^1$ represents hydrogen, $R^2$ represents a methyl group, and $R^4$ represents an ethyl group in the ortho-position with respect to $R^3$.

x) Another further preferred embodiment of the invention relates to thiophene derivatives according to any one of embodiments i) to vi), wherein $R^1$ represents hydrogen, $R^2$ represents a methoxy group, and $R^4$ represents chloro or fluoro both in the ortho-position with respect to $R^3$.

xi) Another further preferred embodiment of the invention relates to thiophene derivatives according to any one of embodiments i) to vi), wherein $R^1$ represents hydrogen, $R^2$ represents a methyl group and $R^4$ represents chloro in the ortho-position with respect to $R^3$.

xii) Another further preferred embodiment of the invention relates to thiophene derivatives according to any one of embodiments i) to xi), wherein $R^3$ represents 2,3-dihydroxypropyl, —$CH_2$—$(CH_2)_k$—$NR^{31}R^{32}$, (azetidine-3-carboxylic acid)-1-yl-methyl, (azetidine-3-carboxylic acid $C_{1-5}$-alkylester)-1-yl-methyl, 2-[(azetidine-3-carboxylic acid)-1-yl]-ethyl, 2-[(azetidine-3-carboxylic acid $C_{1-5}$-alkylester)-1-yl]-ethyl, 3-[(azetidine-3-carboxylic acid)-1-yl]-propyl, 3-[(azetidine-3-carboxylic acid $C_{1-5}$-alkylester)-1-yl]-propyl, (pyrrolidine-3-carboxylic acid)-1-yl-methyl, (pyrrolidine-3-carboxylic acid $C_{1-5}$-alkylester)-1-yl-methyl, (pyrrolidine-2-carboxylic acid)-1-yl-methyl, (pyrrolidine-2-carboxylic acid $C_{1-5}$-alkylester)-1-yl-methyl, 2-[(pyrrolidine-3-carboxylic acid)-1-yl]-ethyl, 2-[(pyrrolidine-3-carboxylic acid $C_{1-5}$-alkylester)-1-yl]-ethyl, 2-[(pyrrolidine-2-carboxylic acid)-1-yl]-ethyl, 2-[(pyrrolidine-2-carboxylic acid $C_{1-5}$-alkylester)-1-yl]-ethyl, 3-[(pyrrolidine-3-carboxylic acid)-1-yl]-propyl, 3-[(pyrrolidine-3-carboxylic acid $C_{1-5}$-alkylester)-1-yl]-propyl, 3-[(pyrrolidine-2-carboxylic acid)-1-yl]-propyl, 3-[(pyrrolidine-2-carboxylic acid $C_{1-5}$-alkylester)-1-yl]-propyl, —$CH_2$—$(CH_2)_n$$CONR^{31}R^{32}$, —CO—$NHR^{31}$, or —$(CH_2)_n$CH(OH)—$CH_2$—$NR^{31}R^{32}$ and wherein $R^{31}$ and $R^{32}$ are as defined above in embodiment i).

xiii) Another further preferred embodiment of the invention relates to thiophene derivatives according to any one of embodiments i) and iii) to xi), wherein $R^3$ represents 2,3-dihydroxypropyl, —$CH_2$—$(CH_2)_k$—$NR^{31}R^{32}$, (azetidine-3-carboxylic acid)-1-yl-methyl, (azetidine-3-carboxylic acid $C_{1-5}$-alkylester)-1-yl-methyl, 2-[(azetidine-3-carboxylic acid)-1-yl]-ethyl, 2-[(azetidine-3-carboxylic acid $C_{1-5}$-alkylester)-1-yl]-ethyl, 3-[(azetidine-3-carboxylic acid)-1-yl]-propyl, 3-[(azetidine-3-carboxylic acid $C_{1-5}$-alkylester)-1-yl]-propyl, (pyrrolidine-3-carboxylic acid)-1-yl-methyl, (pyrrolidine-3-carboxylic acid $C_{1-5}$-alkylester)-1-yl-methyl, (pyrrolidine-2-carboxylic acid)-1-yl-methyl, (pyrrolidine-2-carboxylic acid $C_{1-5}$-alkylester)-1-yl-methyl, 2-[(pyrrolidine-3-carboxylic acid)-1-yl]-ethyl, 2-[(pyrrolidine-3-carboxylic acid $C_{1-5}$-alkylester)-1-yl]-ethyl, 2-[(pyrrolidine-2-carboxylic acid)-1-yl]-ethyl, 2-[(pyrrolidine-2-carboxylic acid $C_{1-5}$-alkylester)-1-yl]-ethyl, 3-[(pyrrolidine-3-carboxylic acid)-1-yl]-propyl, 3-[(pyrrolidine-3-carboxylic acid $C_{1-5}$-alkylester)-1-yl]-propyl, 3-[(pyrrolidine-2-carboxylic acid)-1-yl]-propyl, 3-[(pyrrolidine-2-carboxylic acid $C_{1-5}$-alkylester)-1-yl]-propyl, —$CH_2$—$(CH_2)_n$—COOH, —$CH_2$—$(CH_2)_n$—$CONR^{31}R^{32}$, —CO—$NHR^{31}$, or —$(CH_2)_n$CH(OH)—$CH_2$—$NR^{31}R^{32}$ and wherein $R^{31}$ and $R^{32}$ are as defined above in embodiment i).

xiv) Another further preferred embodiment of the invention relates to thiophene derivatives according to any one of embodiments i) to xi), wherein $R^3$ represents —$OCH_2$—$(CH_2)_m$—$NR^{31}R^{32}$, 2-pyrrolidin-1-yl-ethoxy, 3-pyrrolidin-1-yl-propoxy, 2-piperazin-1-yl-ethoxy, 2-[4-($C_{1-5}$-alkyl)-piperazin-1-yl]-ethoxy, 2-[4-(2-hydroxy-ethyl)-piperazin-1-yl]-ethoxy, 3-piperazin-1-yl-propoxy, 3-[4-($C_{1-5}$-alkyl)-piperazin-1-yl]-propoxy, 3-[4-(2-hydroxy-ethyl)-piperazin-1-yl]-propoxy, 2-morpholin-4-yl-ethoxy, 3-morpholin-4-yl-propoxy, 2-[(azetidine-3-carboxylic acid)-1-yl]-ethoxy, 2-[(azetidine-3-carboxylic acid $C_{1-5}$-alkylester)-1-yl]-ethoxy, 2-[(pyrrolidine-3-carboxylic acid)-1-yl]-ethoxy, 2-[(pyrrolidine-3-carboxylic acid $C_{1-5}$-alkylester)-1-yl]-ethoxy, 2-[(pyrrolidine-2-carboxylic acid)-1-yl]-ethoxy, 2-[(pyrrolidine-2-carboxylic acid $C_{1-5}$-alkylester)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid $C_{1-5}$-alkylester)-1-yl]-propoxy, 3-[(pyrrolidine-3-carboxylic acid)-1-yl]-propoxy, 3-[(pyrrolidine-3-carboxylic acid $C_{1-5}$-alkylester)-1-yl]-propoxy, 3-[(pyrrolidine-2-carboxylic acid)-1-yl]-propoxy, 3-[(pyrrolidine-2-carboxylic acid $C_{1-5}$-alkylester)-1-yl]-propoxy, 3-[(2-hydroxy-pyrrolidine)-1-yl]-propoxy, 3-[(3-hydroxy-pyrrolidine)-1-yl]-propoxy, —O—$CH_2$—$CONR^{31}R^{32}$, 3-carbamoyl-propoxy, 3-($C_{1-5}$-alkylcarbamoyl)propoxy, 3-(2-hydroxyethylcarbamoyl)propoxy, —$OCH_2$—CH(OH)—$CH_2$—$NR^{31}R^{32}$, 3-[(azetidine-3-carboxylic acid)-1-yl]-2-hydroxypropoxy, 3-[(azetidine-3-carboxylic acid $C_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid $C_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid $C_{1-5}$-alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-($C_{1-5}$-alkyl)-piperazin-1-yl]-propoxy, 2-hydroxy-3-[4-(2-hydroxy-ethyl)-piperazin-1-yl]-propoxy, or 2-hydroxy-3-morpholin-4-yl-propoxy and wherein $R^{31}$ and $R^{32}$ are as defined above in embodiment i).

xv) Another further preferred embodiment of the invention relates to thiophene derivatives according to any one of embodiments i) to xi), wherein $R^3$ represents —$OCH_2$—$(CH_2)_m$—$NR^{31}R^{32}$, —O—$CH_2$—$CONR^{31}R^{32}$, or —OCH$_2$—CH(OH)—CH$_2$—NR$^{31}$R$^{32}$, wherein R$^{31}$ represents methyl or 2-hydroxyethyl, and R$^{32}$ represents hydrogen.

xvi) Another further preferred embodiment of the invention relates to thiophene derivatives according to any one of embodiments i) to xi), wherein R$^3$ represents —OCH$_2$—(CH$_2$)$_m$—NR$^{31}$R$^3$, 2-[(azetidine-3-carboxylic acid)-1-yl]-ethoxy, 2-[(pyrrolidine-3-carboxylic acid)-1-yl]-ethoxy, 2-[(pyrrolidine-2-carboxylic acid)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(pyrrolidine-3-carboxylic acid)-1-yl]-propoxy, 3-[(pyrrolidine-2-carboxylic acid)-1-yl]-propoxy, 3-[(2-hydroxy-pyrrolidine)-1-yl]-propoxy, 3-[(3-hydroxy-pyrrolidine)-1-yl]-propoxy, —O—CH$_2$—CONR$^{31}$R$^{32}$, —OCH$_2$—CH(OH)—CH$_2$—NR$^{31}$R$^{32}$, 3-[(azetidine-3-carboxylic acid)-1-yl]-2-hydroxypropoxy, 2-hydroxy-3-[(pyrrolidine-3-carboxylic acid)-1-yl]-propoxy, 2-hydroxy-3-[(pyrrolidine-2-carboxylic acid)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-(C$_{1-5}$-alkyl)-piperazin-1-yl]-propoxy and wherein R$^{31}$ and R$^{32}$ are as defined above in embodiment i).

xvii) Another further preferred embodiment of the invention relates to thiophene derivatives according to any one of embodiments i) to xi), wherein R$^3$ represents —CH$_2$—(CH$_2$)$_k$—NHSO$_2$R$^{33}$, —(CH$_2$)$_n$CH(OH)—CH$_2$—NHSO$_2$R$^{33}$, —OCH$_2$—(CH$_2$)$_m$—NHSO$_2$R$^{33}$, —OCH$_2$—CH(OH)—CH$_2$—NHSO$_2$R$^{33}$ —CH$_2$—(CH$_2$)$_k$—NHCOR$^{34}$, —(CH$_2$)$_n$CH(OH)—CH$_2$—NHCOR$^{34}$, —OCH$_2$—(CH$_2$)$_m$—NHCOR$^{34}$, or —OCH$_2$—CH(OH)—CH$_2$—NHCOR$^{34}$ and wherein R$^{33}$ and R$^{34}$ are as defined above in embodiment i).

xviii) Specific especially preferred thiophene derivatives according to Formula (I) are:

3-[4-(3-amino-propyl)-phenyl]-1-((1aS,5aR)-1,1,2-trimethyl-1,1a,5,5a-tetrahydro-3-thia-cyclopropa[a]pentalen-4-yl)-propan-1-one, 3-[4-(3-methylamino-propyl)-phenyl]-1-((1aS,5aR)-1,1,2-trimethyl-1,1a,5,5a-tetrahydro-3-thia-cyclopropa[a]pentalen-4-yl)-propan-1-one, 3-{4-[3-(2-hydroxy-ethylamino)-propyl]-phenyl}-1-((1aS,5aR)-1,1,2-trimethyl-1,1a,5,5a-tetrahydro-3-thia-cyclopropa[a]pentalen-4-yl)-propan-1-one, 3-{4-[3-(2-hydroxy-1-hydroxymethyl-ethylamino)-propyl]-phenyl}-1-((1aS,5aR)-1,1,2-trimethyl-1,1a,5,5a-tetrahydro-3-thia-cyclopropa[a]pentalen-4-yl)-propan-1-one, 1-{4-[3-oxo-3-((1aS,5aR)-1,1,2-trimethyl-1,1a,5,5a-tetrahydro-3-thia-cyclopropa[a]pentalen-4-yl)-propyl]-benzyl}-azetidine-3-carboxylic acid, 3-(2-hydroxy-3-{2-methyl-4-[3-oxo-3-((1aS,5aR)-1,1,2-trimethyl-1,1a5,5a-tetrahydro-3-thia-cyclopropa[a]pentalen-4-yl)-propyl]-phenoxy}-propylamino)-propionic acid, 3-[3-chloro-4-(2-hydroxy-3-methylamino-propoxy)-phenyl]-1-((1aS,5aR)-1,1,2-trimethyl-1,1a,5,5a-tetrahydro-3-thia-cyclopropa[a]pentalen-4-yl)-propan-1-one, 3-(3-{2-chloro-4-[3-oxo-3-((1aS,5aR)-1,1,2-trimethyl-1,1a,5,5a-tetrahydro-3-thia-cyclopropa[a]pentalen-4-yl)-propyl]-phenoxy}-2-hydroxy-propylamino)-propionic acid, 3-[3,5-dimethyl-4-(2-methylamino-ethoxy)-phenyl]-1-((1aS,5aR)-1,1,2-trimethyl-1,1a,5,5a-tetrahydro-3-thia-cyclopropa[a]pentalen-4-yl)-propan-1-one, 3-[4-(2-dimethylamino-ethoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one, 3-{4-[2-(2-hydroxy-ethylamino)-ethoxy]-3,5-dimethyl-phenyl}-1-((1aS,5aR)-1,1,2-trimethyl-1,1a,5,5a-tetrahydro-3-thia-cyclopropa[a]pentalen-4-yl)-propan-1-one, 3-{4-[2-(2-hydroxy-1-hydroxymethyl-ethylamino)-ethoxy]-3,5-dimethyl-phenyl}-1-((1aS,5aR)-1,1,2-trimethyl-1,1a,5,5a-tetrahydro-3-thia-cyclopropa[a]pentalen-4-yl)-propan-1-one, 3-[3,5-dimethyl-4-(2-pyrrolidin-1-yl-ethoxy)-phenyl]-1-((1aS,5aR)-1,1,2-trimethyl-1,1a,5,5a-tetrahydro-3-thia-cyclopropa[a]pentalen-4-yl)-propan-1-one, 1-(2-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-ethyl)-azetidine-3-carboxylic acid, 3-{4-[3-(2-hydroxy-ethylamino)-propoxy]-3,5-dimethyl-phenyl}-1-((1aS,5aR)-1,1,2-trimethyl-1,1a,5,5a-tetrahydro-3-thia-cyclopropa[a]pentalen-4-yl)-propan-1-one, (3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-propylamino)-acetic acid, 3-[4-(3-amino-2-hydroxy-propoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one, 3-[4-(2-hydroxy-3-methylamino-propoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one, 3-{4-[2-hydroxy-3-(2-hydroxy-ethylamino)-propoxy]-3,5-dimethyl-phenyl}-1-((1aS,5aR)-1,1,2-trimethyl-1,1a,5,5a-tetrahydro-3-thia-cyclopropa[a]pentalen-4-yl)-propan-1-one, 3-{4-[2-hydroxy-3-(2-hydroxy-1-hydroxymethyl-ethylamino)-propoxy]-3,5-dimethyl-phenyl}-1-((1aS,5aR)-1,1,2-trimethyl-1,1a,5,5a-tetrahydro-3-thia-cyclopropa[a]pentalen-4-yl)-propan-1-one, (3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-2-hydroxy-propylamino)-acetic acid, 1-(3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-2-hydroxy-propyl)-azetidine-3-carboxylic acid, 2-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-acetamide, 2-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-N-(2-hydroxy-ethyl)-acetamide, 3-{3-ethyl-4-[2-hydroxy-3-(2-hydroxy-ethylamino)-propoxy]-5-methyl-phenyl}-1-((1aR,5aS)-1,1,2-trimethyl-1,1a,5,5a-tetrahydro-3-thia-cyclopropa[a]pentalen-4-yl)-propan-1-one, 3-[3-chloro-5-methoxy-4-(2-methylamino-ethoxy)-phenyl]-1-((1aS,5aR)-1,1,2-trimethyl-1,1a,5,5a-tetrahydro-3-thia-cyclopropa[a]pentalen-4-yl)-propan-1-one, 3-[3-chloro-4-(2-dimethylamino-ethoxy)-5-methoxy-phenyl]-1-((1aS,5aR)-1,1,2-trimethyl-1,1a,5,5a-tetrahydro-3-thia-cyclopropa[a]pentalen-4-yl)-propan-1-one, 3-{3-chloro-4-[2-(2-hydroxy-ethylamino)-ethoxy]-5-methoxy-phenyl}-1-((1aS,5aR)-1,1,2-trimethyl-1,1a,5,5a-tetrahydro-3-thia-cyclopropa[a]pentalen-4-yl)-propan-1-one, 1-(2-{2-chloro-6-methoxy-4-[3-oxo-3-((1aS,5aR)-1,1,2-trimethyl-1,1a,5,5a-tetrahydro-3-thia-cyclopropa[a]pentalen-4-yl)-propyl]-phenoxy}-ethyl)-azetidine-3-carboxylic acid, 3-{3-chloro-4-[3-(2-hydroxy-ethylamino)-propoxy]-5-methoxy-phenyl}-1-((1aS,5aR)-1,1,2-trimethyl-1,1a,5,5a-tetrahydro-3-thia-cyclopropa[a]pentalen-4-yl)-propan-1-one, 3-{3-chloro-4-[2-hydroxy-3-(2-hydroxy-ethylamino)-propoxy]-5-methoxy-phenyl}-1-((1aS,5aR)-1,1,2-trimethyl-1,1a,5,5a-tetrahydro-3-thia-cyclopropa[a]pentalen-4-yl)-propan-1-one, 3-(3-{2-chloro-6-methoxy-4-[3-oxo-3-((1aS,5aR)-1,1,2-trimethyl-1,1a,5,5a-tetrahydro-3-thia-cyclopropa[a]pentalen-4-yl)-propyl]-phenoxy}-2-hydroxy-propylamino)-propionic acid, 3-[3-chloro-4-(2-hydroxy-3-methoxy-propoxy)-5-methyl-phenyl]-1-((1aS,5aR)-1,1,2-trimethyl-1,1a,5,5a-tetrahydro-3-thia-cyclopropa[a]pentalen-4-yl)-propan-1-one, N-(2-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-ethyl)-methanesulfonamide, ethanesulfonic acid (2-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-ethyl)-amide, propane-1-sulfonic acid (2-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-ethyl)-amide, N-(3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-propyl)-methanesulfonamide, N-(3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-2-hydroxy-propyl)-methanesulfonamide, ethanesulfonic acid (3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-2-hydroxy-propyl)-amide, propane-1-sulfonic acid (3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-2-hydroxy-propyl)-amide, N-(3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-2-hydroxy-propyl)-2-hydroxy-acetamide, and N-(3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-propyl)-2-hydroxy-acetamide.

xix) Additional specific preferred thiophene derivatives according to Formula (I) are:

3-[4-(2-hydroxy-3-methoxy-propoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one, 2-amino-N-(3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-2-hydroxy-propyl)-acetamide, 3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenyl}-N-(2-hydroxy-1-hydroxymethyl-ethyl)-propionamide, 3-[4-(2,3-dihydroxy-propyl)-3,5-dimethyl-phenyl]-1-((1aR,5aS)-1,1,2-trimethyl-1,1a,5,5a-tetrahydro-3-thia-cyclopropa[a]pentalen-4-yl)-propan-1-one, N-(3-{2-ethyl-6-methyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-2-hydroxy-propyl)-2-hydroxy-acetamide, 3-{2-ethyl-6-methyl-4-[3-oxo-3-((1aS,5aR)-1,1,2-trimethyl-1,1a,5,5a-tetrahydro-3-thia-cyclopropa[a]pentalen-4-yl)-propyl]-phenyl}-N-(2-hydroxy-ethyl)-propionamide, 3-{2-ethyl-6-methyl-4-[3-oxo-3-((1aS,5aR)-1,1,2-trimethyl-1,1a,5,5a-tetrahydro-3-thia-cyclopropa[a]pentalen-4-yl)-propyl]-phenyl}-N-(2-hydroxy-1-hydroxymethyl-ethyl)-propionamide, 3-[3,5-dichloro-4-(2-hydroxy-3-methoxy-propoxy)-phenyl]-1-((1aS,5aR)-1,1,2-trimethyl-1,1a,5,5a-tetrahydro-3-thia-cyclopropa[a]pentalen-4-yl)-propan-1-one, 3-[4-(2-hydroxy-ethylamino)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one, and 3-[4-(3-hydroxy-propylamino)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one.

The compounds of Formula (I) and their pharmaceutically acceptable salts can be used as medicaments, e.g. in the form of pharmaceutical compositions for enteral, parental or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical compositions can be effected in a manner which will be familiar to any person skilled in the art (see for example Mark Gibson, Editor, Pharmaceutical Preformulation and Formulation, IHS Health Group, Englewood, Colo. USA, 2001; Remington, The Science and Practice of Pharmacy, 20th Edition, Philadelphia College of Pharmacy and Science) by bringing the described compounds of Formula (I) or their pharmaceutically acceptable salts, optionally in combination with other therapeutically valuable substances, into a galenical administration form together with suitable, non-toxic, inert, pharmaceutically acceptable solid or liquid carrier materials and, if desired, usual pharmaceutical adjuvants.

The pharmaceutical compositions comprising a compound of Formula (I) are useful for the prevention and/or treatment of diseases or disorders associated with an activated immune system.

Such diseases or disorders are selected from the group consisting of rejection of transplanted organs such as kidney, liver, heart, lung, pancreas, cornea, and skin; graft-versus-host diseases brought about by stem cell transplantation; autoimmune syndromes including rheumatoid arthritis, multiple sclerosis, inflammatory bowel diseases such as Crohn's disease and ulcerative colitis, psoriasis, psoriatic arthritis, thyroiditis such as Hashimoto's thyroiditis, uveo-retinitis; atopic diseases such as rhinitis, conjunctivitis, dermatitis; asthma; type I diabetes; post-infectious autoimmune diseases including rheumatic fever and post-infectious glomerulonephritis; solid cancers and tumor metastasis.

Preferably, the diseases or disorders to be prevented or treated with the compounds of Formula (I) are selected from the group consisting of rejection of transplanted organs selected from kidney, liver, heart and lung; graft-versus-host diseases brought about by stem cell transplantation; autoimmune syndromes selected from rheumatoid arthritis, multiple sclerosis, psoriasis, psoriatic arthritis, Crohn's disease, and Hashimoto's thyroiditis; and atopic dermatitis.

The present invention also relates to a method for the prevention or treatment of a disease or disorder mentioned herein comprising administering to a patient a pharmaceutically active amount of a compound of Formula (I).

Furthermore, compounds of the Formula (I) are also useful, in combination with one or several immunomodulating agents, for the prevention and/or treatment of the diseases and disorders mentioned herein. According to a preferred embodiment of the invention, said agents are selected from the group consisting of immunosuppressants, corticosteroids, NSAID's, cytotoxic drugs, adhesion molecule inhibitors, cytokines, cytokine inhibitors, cytokine receptor antagonists and recombinant cytokine receptors.

Still a further object of the present invention is a process to prepare a pharmaceutical composition comprising a compound of the Formula (I) by mixing one or more active ingredients with inert excipients in a manner known per se.

The present invention also relates to the use of a compound of Formula (I) for the preparation of a pharmaceutical composition, optionally for use in combination with one or several immunomodulating agents, for the prevention and/or treatment of the diseases and disorders mentioned herein.

The present invention also relates to pro-drugs of a compound of Formula (I) that convert in vivo to the compound of Formula (I) as such. Any reference to a compound of Formula (I) is therefore to be understood as referring also to the corresponding pro-drugs of the compound of Formula (I), as appropriate and expedient.

The compounds of Formula (I) can be manufactured by the methods given below, by the methods given in the Examples or by analogous methods. Optimum reaction conditions may vary with the particular reactants or solvents used, but such conditions can be determined by a person skilled in the art by routine optimisation procedures.

Compounds of the Formula (I) of the present invention can be prepared according to the general sequence of reactions outlined below. Only a few of the synthetic possibilities leading to compounds of Formula (I) are described.

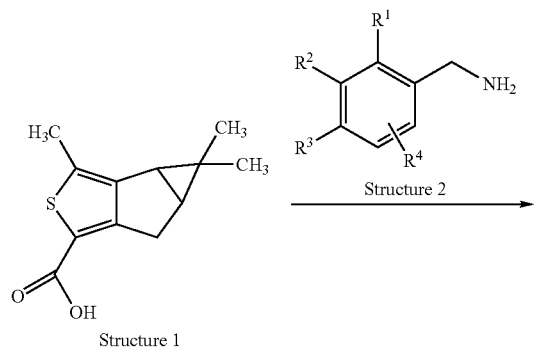

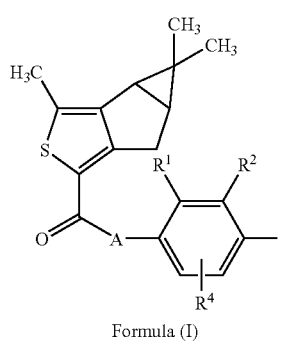

Formula (I)

In case A represents —NH—CH$_2$—, the compounds of the Formula (I) may be prepared by reacting a compound of Structure 1 with a compound of Structure 2 in the presence of an activating agent such as EDC, DCC, HOBt, BOP, PyBOP, BOP—Cl, etc. in a solvent such as THF, dioxane, DMF, DCM, acetonitrile, etc. In case A represents —CH$_2$—CH$_2$—, the compounds of Formula (I) may be prepared by reacting a compound of Structure 3 with a compound of Structure 4 under Grignard conditions, preferably at temperatures below rt. The Grignard reagent of Structure 4 is prepared according to standard methodology. The functional groups present in the residues R$^1$ to R$^4$ may require temporary protection or may even be introduced in additional steps that follow the Grignard reaction. The Weinreb amide compound of Structure 3 is prepared by treating the compound of Structure 1 with N,O-dimethylhydroxylamine hydrochloride in the presence of coupling reagent such as EDC, DCC, etc. (M. Mentzel, H. M. R. Hoffmann, N-Methoxy N-methyl amides (Weinreb amides) in modern organic synthesis, *Journal fuer Praktische Chemie/Chemiker-Zeitung* 339 (1997), 517-524; J. Singh, N. Satyamurthi, I. S. Aidhen, The growing synthetic utility of Weinreb's amide, *Journal fuer Praktische Chemie* (Weinheim, Germany) 342 (2000) 340-347; V. K. Khlestkin, D. G. Mazhukin, Recent advances in the application of N,O-dialkylhydroxylamines in organic chemistry, *Current Organic Chemistry* 7 (2003), 967-993).

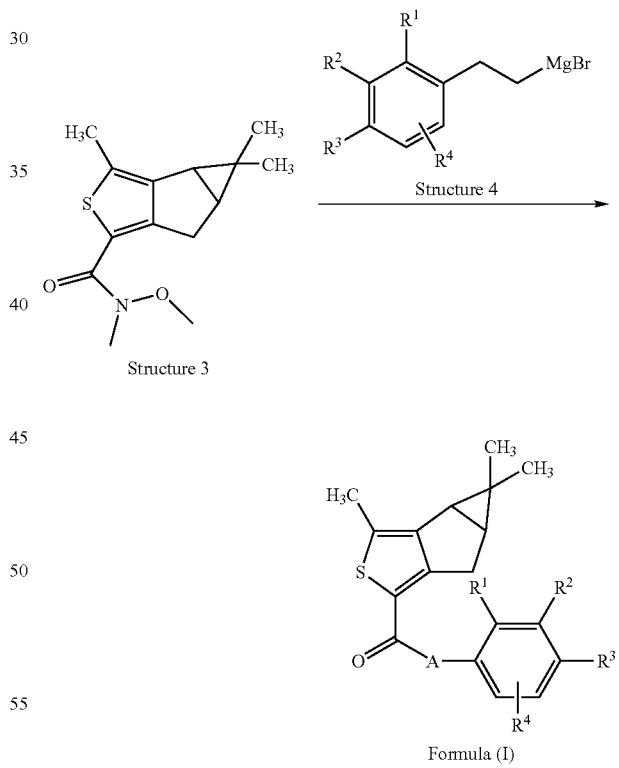

In case A represents —CH═CH—, the compounds of Formula (I) may be prepared by reacting a compound of Structure 5 with a compound of Structure 6. Compounds of Formula (I) wherein A represents —CH$_2$—CH$_2$— may also be prepared by reacting a compound of Formula (I) wherein A represents —CH═CH— (Structure 12) with hydrogen in the presence of a catalyst such as Pd/C, Pt/C, PtO$_2$, etc. in a solvent such as ethanol, methanol, THF, etc.

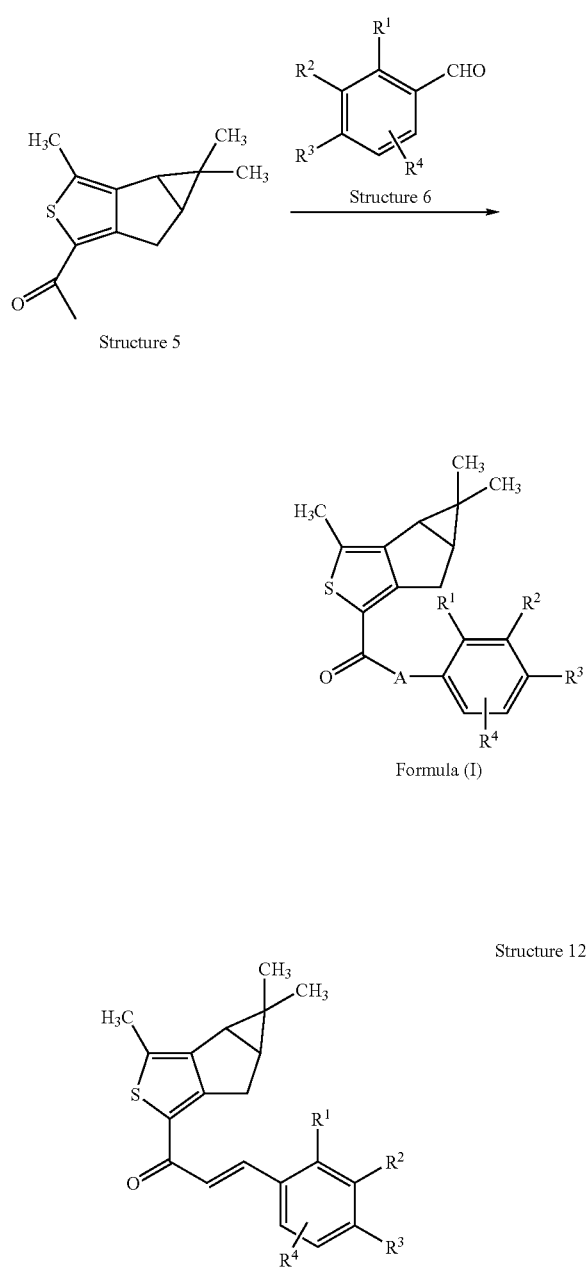

Formula (I)

Structure 12

Compounds of the Formula (I) wherein A represents —CH₂—O— or —CH₂—NH— may be prepared by reacting a compound of Structure 7 with a compound of Structure 8 in the presence or absence of a base such as K₂CO₃, Na₂CO₃, K-tert.butoxide, NaOH, NaH, triethylamine, DIPEA, etc. in a solvent such as acetone, DMF, THF, dioxane, etc. or mixtures thereof. The compound of Structure 7 can be prepared by reacting the compound of Structure 5 with a brominating agent such as phenyltrimethylammoniumbromid dibromide, benzyltrimethylammonium-tribromid, triphenylphosphine dibromide, etc. in a solvent such as DCM, chloroform, THF, diethyl ether, methanol, ethanol, etc, and mixtures thereof.

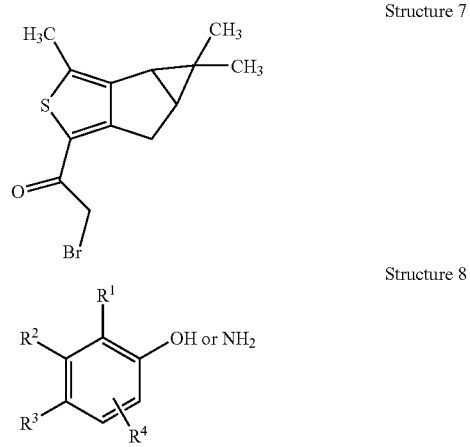

The compound of Structure 5 may be prepared by treating the compound of Structure 1 with MeLi in a solvent such as diethyl ether, THF, dioxane, at temperatures between −20 and 50° C. Alternatively, the compound of Structure 5 may be prepared by reacting the compound of Structure 3 with methylmagnesium bromide.

Depending on the nature of the functionalities present in the residues $R^1$ to $R^4$ in Structures 2, 4, 6 and 8, these functionalities may require temporary protection. Appropriate protecting groups are known to a person skilled in the art and include e.g. a benzyl or a trialkylsilyl group to protect an alcohol, a ketal to protect a diol, etc. These protecting groups may be employed according to standard methodology (e.g. T. W. Greene, P. G. M. Wuts, Protective Groups in Organic Synthesis, 3$^{rd}$ Edition, Wiley New York, 1991; P. J. Kocienski, Protecting Groups, Thieme Stuttgart, 1994). Alternatively, the desired residues $R^1$ to $R^4$ may also be introduced in later steps that follow the reaction of a compound of Structure 1, 3, 5 or 7 with a suitable precursor of a compound of Structure 2, 4, 6 or 8, respectively. The compounds of Structure 2, 4, 6 and 8 or their precursors are either commercially available or are prepared according to procedures known to a person skilled in the art.

The compound of Structure 1 may be prepared by reacting a compound of Structure 9 with an aqueous base such as aqueous (aq.) NaOH, aq. LiOH, aq. KOH, etc. or an acid such as aq. HCl, trifluoroacetic acid, etc. in a solvent such as water, ethanol, methanol, THF, etc. or mixtures thereof.

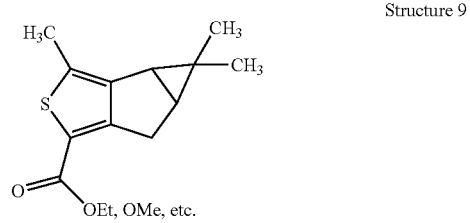

The compounds of Structure 9 are prepared by treating a compound of Structure 10 with a non-aqueous base such as NaOMe, NaOEt, KO-tert.-Bu, DBU, etc. in a solvent such as methanol, ethanol, THF, DMF, etc., or mixtures thereof, preferably at elevated temperatures.

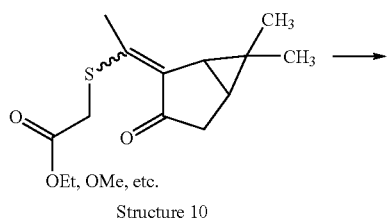

Structure 10

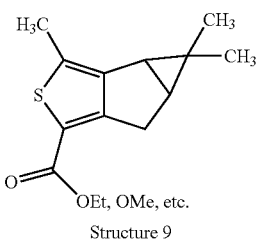

Structure 9

The compounds of Structure 10 are prepared by treating a compound of Structure 11 with a 2-mercaptoacetic acid ester in the presence of a base such a NaH, NaOEt, NaOMe, K tert.-butoxide, etc. in THF, dioxane, DMF, ethanol, methanol, etc. or mixtures thereof. In addition, the compound of Structure 1 may also be prepared in a one-pot three step procedure starting from the compound of Structure 11 following the above reaction sequence.

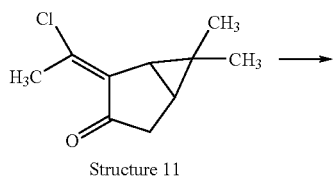

Structure 11

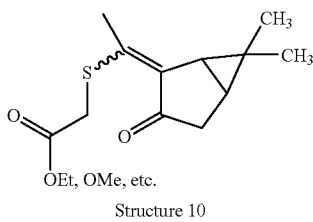

Structure 10

The (1S,5R)-isomer of 2-[1-chloro-ethylidene]-6,6-dimethyl-bicyclo[3.1.0]hexan-3-one ((1S,5R)-isomer of compound of Structure 11) may be prepared starting from commercially available (+)-3-carene according to the procedures given in the literature (e.g. S. A. Popov, A. Yu. Denisov, Yu. V. Gatilov, I. Yu. Bagryanskaya and A. V. Tkachev, *Tetrahedron Asymmetry* 5 (1994), 479-489; S. A. Popov, A. V. Tkachev; *Synthetic Commun.* 31 (2001), 233-243).

The racemic form of Structure 11 may be prepared starting from (+)-3-carene following the procedures given in the literature (W. Cocker, D. H. Grayson, *Tetrahedron Lett.* 51 (1969), 4451-4452; S. Lochynski; B. Jarosz, M. Walkowicz, K. Piatkowski, *J. Prakt. Chem.* (Leipzig) 330 (1988), 284-288; M. Walkowicz, H. Kuczynsky, C. Walkowicz, *Roczniki Chemii Ann. Soc. Chim. Polonorum* 41 (1967), 927-937; H. Kuczynski, M. Walkowicz, C. Walkowicz, K. Nowak, I. Z. Siemion, *Roczniki Chemii Ann. Soc. Chim. Polonorum,* 38 (1964), 1625-1633; A. V. Pol, V. G. Naik, H. R. Sonawane, *Ind. J. Chem. Sect B,* 19 (1980) 603-604; S. A. Popov, A. Yu. Denisov, Yu. V. Gatilov, I. Yu. Bagryanskaya and A. V. Tkachev, *Tetrahedron Asymmetry* 5 (1994), 479-489; S. A. Popov, A. V. Tkachev; *Synthetic Commun.* 31 (2001), 233-243) and is exemplified below.

The compounds of the Formula (I) that base on the (1R, 5S)-isomer of 2-[1-chloro-ethylidene]-6,6-dimethyl-bicyclo[3.1.0]hexan-3-one ((1R,5S)-isomer of compound of Structure 11) may be obtained by resolving the racemic mixture of a compound of Formula (I), or one of its precursors, into its pure enantiomers by a method known per se to a person skilled in the art, preferably by chromatography or crystallisation.

EXAMPLES

The following examples illustrate the invention but do not at all limit the scope thereof.

All temperatures are stated in degrees Celsius. Compounds are characterized by $^1$H-NMR (300 MHz) or $^{13}$C-NMR (75 MHz) (Varian Oxford; chemical shifts are given in ppm relative to the solvent used; multiplicities: s=singlet, d=doublet, t=triplet; p=pentuplet, hex=hexet, hept=heptet, m=multiplet, br=broad, coupling constants are given in Hz); by LC-MS (Finnigan Navigator with HP 1100 Binary Pump and DAD, column: 4.6×50 mm, Zorbax SB-AQ, 5 μm, 120 Å, gradient: 5-95% acetonitrile in water, 1 min, with 0.04% trifluoroacetic acid, flow: 4.5 mL/min), $t_R$ is given in min; by TLC (TLC-plates from Merck, Silica gel 60 $F_{254}$); or by melting point. Compounds are purified by preparative HPLC (column: X-terra RP18, 50×19 mm, 5 μm, gradient: 10-95% acetonitrile in water containing 0.5% of formic acid) or by MPLC (Labomatic MD-80-100 pump, Linear UVIS-201 detector, column: 350×18 mm, Labogel-RP-18-5s-100, gradient: 10% methanol in water to 100% methanol).

Abbreviations (as used herein)
abs. absolute
approx. approximately
aq. aqueous
atm atmosphere
BOC-anhydride di-tert. butyl dicarbonate
BOP (benzotriazol-1-yloxy)-tris-(dimethylamino)-phosphonium hexafluorophosphate
BOP—Cl bis-(2-oxo-3-oxazolidinyl)-phosphinic acid chloride
BSA bovine serum albumin
Bu butyl
CC column chromatography
conc. Concentrated
DBU 1,8-diazabicylo[5.4.0]undec-7-en
DCC dicyclohexyl carbodiimide
DCM dichloromethane
DEAD diethylazodicarboxylate
DIPEA diisopropyl-ethylamine, Hünig's base, ethyl-diisopropylamine
DMF dimethylformamide
DMSO dimethylsulfoxide
DPPP 1,3-bis-(diphenylphosphino)-propane
EA ethyl acetate
EDC N-(3-dimethylaminopropyl)-N'-ethyl-carbodiimide
eq. equivalent(s)
Et ethyl
h hour(s)
Hex hexane
HMDS hexamethyldisilazane
HOBt 1-hydroxybenzotriazole
HPLC high performance liquid chromatography
HV high vacuum conditions
LC-MS liquid chromatography—mass spectrometry Me methyl
min minute(s)
MPLC medium pressure liquid chromatography
NMO N-methylmorpholine-N-oxide
OAc acetate
prep. preparative
PyBOP benzotriazol-1-yl-oxy-tris-pyrolidino-phosphonium-hexafluoro-phosphat
rt room temperature
sat. saturated
S1P sphingosine 1-phosphate
TBTU 2-(1H-benzotriazole-1-yl)-1,2,3,3-tetramethyluronium tetrafluoroborate
TFA trifluoroacetic acid
THF tetrahydrofuran
TLC thin layer chromatography
$t_R$ retention time (1aS,5aR)-1,1,2-Trimethyl-1,1a,5,5a-tetrahydro-3-thia-cyclopropa[a]pentalene-4-carboxylic acid ethyl ester (Compound of Structure 9)

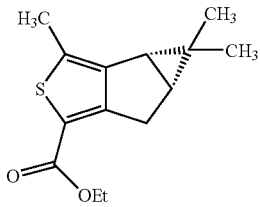

a) NaH (7.0 g, 60% dispersion in mineral oil, 175 mmol) is washed with pentane (100 mL) before it is suspended in THF (400 mL). The suspension is cooled to 0° C. and a solution of ethyl 2-mercaptoacetate (12.62 g, 105 mmol) in THF (50 mL) is added over a period of 20 min. The temperature of the reaction is maintained at 5-10° C. Upon completion of the addition, the cooling is removed and stirring is continued for 30 min. A solution of (1S,5R)-2-(1-chloro-(E)-ethylidene)-6,6-dimethyl-bicyclo[3.1.0]hexan-3-one (S. A. Popov, A. Yu. Denisov, Yu. V. Gatilov, I. Yu. Bagryanskaya and A. V. Tkachev, *Tetrahedron Asymmetry* 5 (1994), 479-489; S. A. Popov, A. V. Tkachev; *Synthetic Commun.* 31 (2001), 233-243) (12.93 g, 70 mmol) in THF (50 mL) is added to the suspension and the resulting mixture is stirred for 1.5 h at rt. The mixture is filtered, the filtrate is concentrated to about 100 mL, diluted with 1 M aq. NaOH (100 mL) and extracted twice with DCM (150 mL). The extracts are dried over $Na_2SO_4$ and evaporated to furnish a crude E/Z mixture of {1-[(1S,5R)-6,6-dimethyl-3-oxo-bicyclo[3.1.0]hexylidene]-ethylsulfanyl}-acetic acid ethyl ester (18.2 g) as a brown oil. LC-MS: $t_R$=1.00 min, [M+1]+=269.13. $^1$H NMR ($CDCl_3$): δ 4.22 (q, J=7.0 Hz, 2H both isomers), 3.67 (d, J=15.8 Hz, 1H major isomer), 3.63 (d, J=15.8 Hz, 1H minor isomer), 3.58 (d, J=15.8 Hz, 1H major isomer), 3.54 (d, J=15.8 Hz, 1H, minor isomer), 2.67 (dd, J=6.4, 19.4 Hz, 1H minor isomer), 2.60 (dd, J=7.0, 19.4 Hz, 1H major isomer), 2.58 (s, 3H minor isomer), 2.52 (s, 3H major isomer), 2.36-2.32 (m, 1H major isomer), 2.30-2.26 (m, 1H major isomer, 1H minor isomer), 2.18 (d, J=7.0 Hz, 1 H minor isomer), 2.00 (d, J=7.0 Hz, 1 H major isomer), 1.95 (d, J=7.6 Hz, 1H minor isomer), 1.30 (t, J=7.0 Hz, 3H major isomer), 1.28 (t, J=7.0 Hz, 3H minor isomer), 1.18 (s, 3H major isomer), 1.15 (s, 3H minor isomer), 0.89 (s, 3H minor isomer), 0.85 (s, 3H major isomer).

b) A solution of Na (1.70 g, 74.8 mmol) in abs. ethanol (75 mL) is heated to 60° C. before it is treated with a solution of crude {1-[(1S,5R)-6,6-dimethyl-3-oxo-bicyclo[3.1.0]hex-(2Z)-ylidene]-ethylsulfanyl}-acetic acid ethyl ester (18.2 g, 68.0 mmol) in abs. ethanol (200 mL). The mixture is stirred at 75° C. for 20 min, then cooled to rt, diluted with 0.5 M aq. NaOH (500 mL) and extracted with DCM (450+200 mL). The combined extracts are dried over $Na_2SO_4$, filtered and the solvent is removed in vacuo. This yields crude (1aS,5aR)-1,1,2-trimethyl-1,1a,5,5a-tetrahydro-3-thia-cyclopropa[a]pentalene-4-carboxylic acid ethyl ester (10.5 g) as a yellow oil of 87% puritiy (LC-MS, UV 280 nm). LC-MS: $t_R$=1.11 min, [M+1]+=251.14; $^1$H NMR ($CDCl_3$): δ 4.26 (q, J=7.0 Hz, 2H), 2.95 (dp, $J_d$=18.8 Hz, $J_p$=3.5 Hz, 1H), 2.79 (d, J=19.3, 1H), 2.37 (s, 3H), 1.89-1.84 (m, 2H), 1.34 (t, J=7.0 Hz, 3H), 1.12 (s, 3H), 0.72 (s, 3H).

(1aS,5aR)-1,1,2-Trimethyl-1,1a,5,5a-tetrahydro-3-thia-cyclopropa[a]pentalene-4-carboxylic acid (Compound of Structure 1)

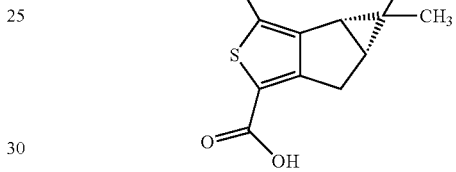

To a solution of crude (1aS,5aR)-1,1,2-trimethyl-1,1a,5,5a-tetrahydro-3-thia-cyclopropa[a]pentalene-4-carboxylic acid ethyl ester (10.3 g, 41.2 mmol) in ethanol (200 mL) a solution of 2N aq. LiOH (300 mL) is added. The resulting mixture is stirred at 70° C. for 1 h, cooled to rt and diluted with water (250 mL). The aq. solution is extracted three times with DCM (125 mL) before it is acidified to pH 3 by adding citric acid. The acidified solution is extracted twice with DCM (2×250 mL). These second extracts are combinded, dried over $Na_2SO_4$, filtered and evaporated to leave (1aS,5aR)-1,1,2-trimethyl-1,1a,5,5a-tetrahydro-3-thia-cyclopropa[a]pentalene-4-carboxylic acid (7.0 g) as a yellow solid. LC-MS: $t_R$=0.95 min, [M+1]+=223.00. $^1$H NMR ($CDCl_3$): δ 3.04-2.92 (m, 1H), 2.83 (d, J=19.3 Hz, 1H), 2.39 (s, 3H), 1.91-1.87 (m, 2H), 1.13 (s, 3H), 0.73 (s, 3H).

Alternatively, (1aS,5aR)-1,1,2-trimethyl-1,1a,5,5a-tetrahydro-3-thia-cyclopropa[a]pentalene-4-carboxylic acid is also obtained by the following procedure: To a solution of sodium (2.80 g, 122 mmol) in ethanol (400 mL) a solution of mercaptoacetic acid ethyl ester (14.64 g, 122 mmol) in ethanol (40 mL) is added. The solution is stirred for 5 min before (1S,5R)-2-(1-chloro-(E)-ethylidene)-6,6-dimethyl-bicyclo[3.1.0]hexan-3-one (15.0 g, 81.2 mmol) in ethanol (40 mL) is added dropwise. The solution becomes slightly warm (approx. 30° C.) and turns orange to brown. A fine precipitate forms. Stirring is continued at rt for 1 h. Then, a solution of sodium (2.24 g, 97.5 mmol) in ethanol (75 mL) is added rapidly and the mixture is heated to 75° C. for 1 h. A 2N aq. solution of LiOH (75 mL) is added and stirring is continued at 75° C. for 2h, then at rt for 16 h. About ⅔ of the solvent is removed in vacuo, the remaining mixture is diluted with water (250 mL) and extracted with DCM (200 mL). The organic extract is washed twice with 1 N aq. (100 mL). The combined aqueous layers are acidified by adding 2N aq. HCl and extracted three times with diethyl ether (3×300 mL). The organic extracts are dried over MgSO₄ and evaporated. The remaining residue is suspended in acetonitrile, filtered, washed with additional acetonitrile and dried under high vacuum to give the title compound (12.02 g) as a pale yellow to beige crystalline powder.

(1aS,5aR)-1,1,2-Trimethyl-1,1a,5,5a-tetrahydro-3-thia-cyclopropa[a]pentalene-4-carboxylic acid methoxy-methyl-amide (Compound of Structure 3)

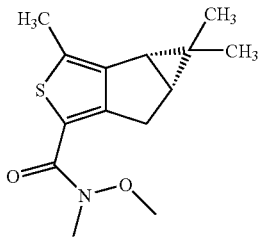

A mixture of N,O-dimehtylhydroxylamine hydrochloride (158 mg, 1.62 mmol) and (1aS,5aR)-1,1,2-trimethyl-1,1a,5,5a-tetrahydro-3-thia-cyclopropa[a]pentalene-4-carboxylic acid (300 mg, 1.35 mmol) in DCM (30 mL) and acetonitrile (10 mL) is treated with diisopropylethylamine (209 mg, 1.62 mmol). To the resulting clear solution EDC.HCl (311 mg, 1.62 mmol) is added and the mixture is stirred at rt for 18 h before it is diluted with DCM (50 mL) and washed with 1 N aq. HCl (2×50 mL) and 1 N aq. NaOH (50 mL). The organic layer is dried over Na₂SO₄ and evaporated. The crude product is purified by prep. HPLC (Phenomenex AQUA 30×75 mm, gradient of 20-95% acetonitril in water containing 0.5% formic acid) to furnish (1aS,5aR)-1,1,2-trimethyl-1,1a,5,5a-tetrahydro-3-thia-cyclopropa[a]pentalene-4-carboxylic acid methoxy-methyl-amide (200 mg) as a pale yellow solid. LC-MS: $t_R$=1.02 min, [M+1]⁺=266.04. ¹H NMR (CDCl₃): δ 3.75 (s, 3H), 3.29 (s, 3H), 3.12-3.01 (m, 1H), 2.93 (d, J=19.0 Hz, 1H), 2.38 (s, 3H), 1.90-1.82 (m, 2H), 1.12 (s, 3H), 0.71 (s, 3H).

(1aS,5aR)-1-(1,1,2-Trimethyl-1,1a,5,5a-tetrahydro-3-thia-cyclopropa[a]pentalen-4-yl)-ethanone (Compound of Structure 5)

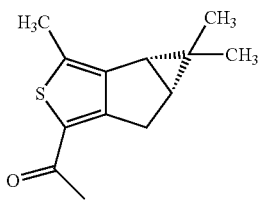

To a solution of (1aS,5aR)-1,1,2-trimethyl-1,1a,5,5a-tetrahydro-3-thia-cyclopropa[a]pentalene-4-carboxylic acid (220 mg, 1.00 mmol) in diethyl ether (10 mL) is added a solution of MeLi (1.6 M, 1.4 mL, 2.10 mmol) in diethyl ether at such a pace that the reaction mixture is refluxing gently. Upon completion of the addition stirring is continued at rt for 30 min. The reaction is quenched by adding sat. aq. NH₄Cl (3 mL). The organic layer is separated, dried over Na₂SO₄ and the solvent is evaporated to give the title compound (165 mg) as a pale yellow oil. LC-MS: $t_R$=1.03 min, [M+1]⁺=221.20; ¹H NMR (CDCl₃): δ 3.00 (ddd, J=1.8, 4.7, 18.8 Hz, 1H), 2.80 (d, J=18.8 Hz, 1H), 2.38 (s, 6H), 1.93-1.90 (m, 2H), 1.14 (s, 3H), 0.74 (s, 3H).

2-Bromo-1-((1aS,5aR)-1,1,2-trimethyl-1,1a,5,5a-tetrahydro-3-thia-cyclopropa[a]pentalen-4-yl)-ethanone (Compound of Structure 7)

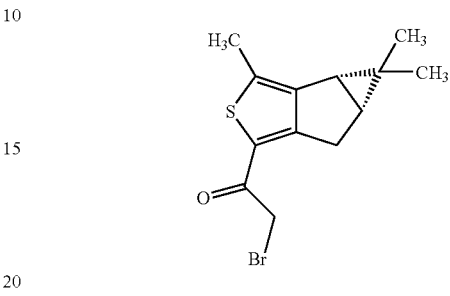

To a solution of (1aS,5aR)-1-(1,1,2-trimethyl-1,1a,5,5a-tetrahydro-3-thia-cyclopropa[a]pentalen-4-yl)-ethanone (275 mg, 1.25 mmol) in DCM (7 mL) and methanol (3.5 mL) is added phenyltrimethyl-ammoniumbromid-dibromid (570 mg, 1.5 mmol) and the reaction mixture is stirred at rt for 30 min. Another portion of phenyltrimethyl-ammoniumbromid-dibromid (600 mg, 1.6 mmol) is added and stirring is continued for 1 h before the mixture is diluted with sat. aq. NaHCO₃ (5 mL) and water (25 mL) and extracted twice with DCM (2×20 mL). The organic extracts are dried over Na₂SO₄ and evaporated to give crude 2-bromo-1-((1aS,5aR)-1,1,2-trimethyl-1,1a,5,5a-tetrahydro-3-thia-cyclopropa[a]pentalen-4-yl)-ethanone (250 mg) as a brownish oil; LC-MS: $t_R$=1.06 min, [M+3]⁺=300.99.

rac-(1S,5R)-2-[1-Chloro-eth-(E)-ylidene]-6,6-dimethyl-bicyclo[3.1.0]hexan-3-one (Compound of Structure 11)

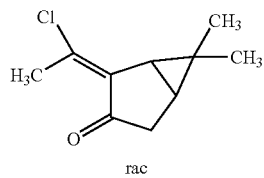

a) To a suspension of (+)-3-carene (82 g, 0.6 mol) and CaCO₃ (80 g, 0.8 mol) in water (300 mL) and dioxan (600 mL) is added N-bromosuccinimide (142 g, 0.8 mol). The mixture is stirred at rt for 1 h, diluted with water (1500 mL) and extracted with diethyl ether (500 mL). The organic extract is washed with water (3×1000 mL) and 5% aq. Na₂S₂O₃ (2×500 mL), and dried over Na₂SO₄. The solvent is removed under reduced pressure and the crude product is purified by column chromatography on silica gel eluting with hexane/EA 4:1 to yield (1S,3R,4R,6R)-4-bromo-3,7,7-trimethyl-bicyclo[4.1.0]heptan-3-ol (48.3 g) as a beige solid. ¹H NMR(CDCl₃): δ 4.05 (dd, J=7.6, 10.6 Hz, 1H), 2.48-2.36 (m, 2H), 2.20 (dd, J=10.0, 14.7 Hz, 1H), 1.42-1.38 (m, 1H), 1.36 (s, 3H), 1.02 (s, 3H), 0.98 (s, 3H), 0.90-0.80 (m, 1H), 0.72-0.66 (m, 1H).

b) To a solution of (1S,3R,4R,6R)-4-bromo-3,7,7-trimethyl-bicyclo[4.1.0]heptan-3-ol (58.0 g, 0.25 mol) in water (120 mL) and dioxane (1600 mL) is added Ag$_2$O (156.4 g, 0.675 mol). The resulting suspension is stirred at rt for 18 h before it is filtered over celite. The filtrate is evaporated under reduced pressure. The remaining solid is dissolved in diethyl ether (650 mL) and washed with water (2×1000 mL). The organic extract is dried over Na$_2$SO$_4$ and the solvent is removed in vacuo to furnish 1-((1S,3S,5R)-6,6-dimethyl-bicyclo[3.1.0]hex-3-yl)-ethanone (36.6 g) as a pale yellow oil. $^1$H NMR (CDCl$_3$: δ 2.83-2.70 (m, 1H), 2.14-2.03 (m, 5H), 1.82 (dd, J=10.0, 14.1 Hz, 2H), 1.16-1.13 (m, 2H), 0.95 (s, 6H).

c) To a solution of 1-((1S,3S,5R)-6,6-dimethyl-bicyclo[3.1.0]hex-3-yl)-ethanone (36.5 g, 0.24 mol) in DCM (700 mL) is added 70% m-chloroperbenzoic acid (77 g, 0.312 mol) in portions. The reaction mixture is stirred at rt for 36 h before it is washed with 0.2 N aq. NaOH (1000 mL). The wash solution is extracted back with DCM (2×300 mL). The combined organic extracts are dried over MgSO$_4$ and the solvent is removed in vacuo to furnish acetic acid (1S,3S,5R)-6,6-dimethyl-bicyclo[3.1.0]hex-3-yl ester (37.8 g) as a pale yellow oil. $^1$H NMR (CDCl$_3$): δ 4.94 (hept. J=3.5 Hz, 1H), 2.02-1.93 (m, 5H), 1.87-1.78 (m, 2H), 1.22-1.15 (m, 2H), 0.95 (s, 3H), 0.83 (s, 3H).

d) A solution of acetic acid (1S,3S,5R)-6,6-dimethyl-bicyclo[3.1.0]hex-3-yl ester (37.85 g, 225 mmol) in ethanol (700 mL) is treated with 2 N aq. LiOH (700 mL). The mixture is stirred at rt for 1 h, diluted with water (600 mL) and extracted with EA (2×150 mL). The combined organic extracts are dried over MgSO$_4$ and evaporated to give (1S,3S,5R)-6,6-dimethyl-bicyclo[3.1.0]hexan-3-ol (23.9 g) as a pale yellow oil. $^1$H NMR (CDCl$_3$): δ 4.23 (hept, J=2.9 Hz, 1H), 1.87-1.70 (m, 4H), 1.23-1.20 (m, 2H), 0.96 (s, 3H), 0.81 (s, 3H).

e) To a mixture of pyridine (80 mL) and DCM (720 mL) is added CrO$_3$ (50 g, 0.5 mol). The mixture is stirred for 5 min before (1S,3S,5R)-6,6-dimethyl-bicyclo[3.1.0]hexan-3-ol (11.5 g, 0.08 mol) is added. Stirring is continued at rt for 2.5 h. The mixture is decanted from an oily residue, diluted with DCM (100 mL) and washed with 2 N aq. HCl (3×80 mL) followed by sat. aq. NaHCO$_3$ solution (80 mL). The separated organic phase is dried over NaSO$_4$ and the solvent is removed in vacuo to give (1S,5R)-6,6-dimethyl-bicyclo[3.1.0]hexan-3-one as a pale yellow oil. $^1$H NMR (CDCl$_3$): δ 2.58-2.46 (m, 2H), 2.19-2.11 (m, 2H), 1.34-1.26 (m, 2H), 1.09 (s, 3H), 0.87 (s, 3H).

f) To a suspension of NaH (873 mg 55% dispersion in mineral oil, 20 mmol, washed with dioxane prior to use) in dioxane (15 mL) is added methyl acetate (2.22 g, 30 mmol). The suspension is stirred for 5 min at rt and a solution of (1S,5R)-6,6-dimethyl-bicyclo[3.1.0]hexan-3-one (1.24 g, 10 mmol) in dioxane (5 mL) is added. The reaction mixture is stirred at 65° C. overnight. The mixture is poured onto cold 10% aq. citric acid solution (75 mL), extracted with DCM (3×75 mL). The organic extracts are washed with water, dried over MgSO$_4$ and evaporated to give crude racemic (1R, 2R, 5R)-2-acetyl-6,6-dimethyl-bicyclo[3.1.0]hexan-3-one (2.45 g, contains dioxane) as a dark yellow liquid. $^1$H NMR (CDCl$_3$): δ 2.61 (dd, J=7.3, 19.6 Hz, 1H), 2.34-2.20 (m, 1H), 2.01 (s, 3H), 1.72 (d, J=8.2 HZ, 1H), 1.40-1.20 (m, 2H), 1.09 (s, 3H), 0.81 (s, 3H).

g) A mixture of the above yellow liquid (1.66 g, 10 mmol), triphenylphosphine (4.53 g, 17 mmol), CCl$_4$ (5 mL) in chloroform (15 mL) is heated to 65° C. for 1 h. The mixture is concentrated and the remaining residue is stirred with pentane. The pentane is decanted, the remaining residue is once more treated with pentane. The pentane fractions are combined and concentrated to leave rac-(1S,5R)-2-[1-chloro-eth-(E)-ylidene]-6,6-dimethyl-bicyclo[3.1.0]hexan-3-one (1.9 g)

as brownish oil. This material is used in the next step without further purification. LC-MS: $t_R$=1.02 min.

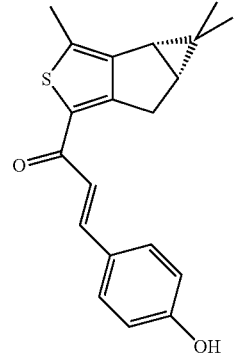

Intermediate 1

A solution of 4-hydroxybenzaldehyde (346 mg, 2.84 mmol) and (1aS,5aR)-1-(1,1,2-trimethyl-1,1a,5,5a-tetrahydro-3-thia-cyclopropa[a]pentalen-4-yl)-ethanone (500 mg, 2.27 mmol) in ethanol (20 mL) and approx. 6 N HCl in isopropanol (4 mL) is stirred at rt for 20 h. The dark brown solution is diluted with diethyl ether and washed with sat. aq. NaHCO$_3$ solution and water. The aq. phases are extracted with diethyl ether. The combined organic extracts are dried over MgSO$_4$ and evaporated. The crude product is purified by crystallisation from methanol to give 3-(4-hydroxy-phenyl)-1-((1aS,5aR)-1,1,2-trimethyl-1,1a,5,5a-tetrahydro-3-thia-cyclopropa[a]pentalen-4-yl)-propenone (694 mg) as an olive powder; LC-MS: $t_R$=1.05 min, [M+1]$^+$=325.22; $^1$H NMR (CDCl$_3$): δ 7.70 (d, J=15.8 Hz, 1H), 7.51 8d, J=8.8 Hz, 2H), 7.10 (d, J=15.2 Hz, 1H), 6.89 (d, J=8.2 Hz, 2H), 5.72 (s, 1H), 3.13 (dd, J=5.9, 18.8 Hz, 1H), 2.94 (d, J=18.8 Hz, 1H), 2.42 (s, 3H), 1.98-1.89 (m, 2H), 1.13 (s, 3H), 0.74 (s, 3H).

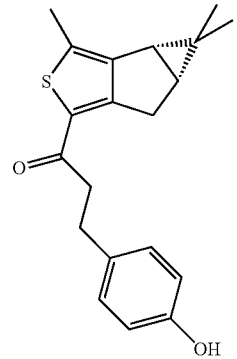

Intermediate 2

A mixture of 3-(4-hydroxy-phenyl)-1-((1aS,5aR)-1,1,2-trimethyl-1,1a,5,5a-tetrahydro-3-thia-cyclopropa[a]pentalen-4-yl)-propenone (690 mg, 2.13 mmol) and Pd/C (200 mg, 10% Pd) in ethanol (25 mL) and THF (25 mL) is stirred at rt for 3 h under H$_2$ (1.5 bar). The mixture is filtered, the filtrate is evaporated and the crude product is purified by CC on silica gel eluting with heptane:EA 7:3 to give 3-(4-hydroxy-phenyl)-1-((1aS,5aR)-1,1,2-trimethyl-1,1a,5,5a-tetrahydro-3-thia-cyclopropa[a]pentalen-4-yl)-propan-1-one (616 mg) as a colourless foam; LC-MS: $t_R$=1.05 min, [M+1]$^+$= 327.24; $^1$H NMR (CDCl$_3$): δ 7.11-7.05 (m, 2H), 6.78-6.70 (m, 2H), 4.75 (s, 1H), 3.04-2.90 (m, 5H), 2.78 (d, J=18.8 Hz, 1H), 2.37 (s, 3H), 1.91-1.85 (m, 2H), 1.11 (s, 3H), 0.70 (s, 3H).

(s, 1H), 6.90-6.87 (m, 1H), 6.83-6.78 (m, 1H), 6.63 (d, J=8.2 Hz, 1H), 3.03-2.86 (m, 3H), 2.77-2.66 (m, 3H), 2.32 (s, 3H), 2.05 (s, 3H), 1.97-1.85 (m, 2H), 1.06 (s, 3H), 0.64 (s, 3H).

Intermediate 3

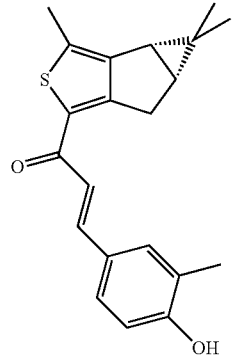

A solution of 4-hydroxy-3-methyl-benzaldehyde (772 mg, 5.67 mmol) and (1aS,5aR)-1-(1,1,2-trimethyl-1,1a,5,5a-tetrahydro-3-thia-cyclopropa[a]pentalen-4-yl)-ethanone (1.0 g, 4.54 mmol) in ethanol (20 mL) and approx. 6 N HCl in isopropanol (5 mL) is stirred at rt for 2 h. The dark brown solution is diluted with diethyl ether and washed with sat. aq. NaHCO$_3$ solution and water. The aq. phases are extracted with diethyl ether. The combined organic extracts are dried over MgSO$_4$ and evaporated. The crude product is suspended in methanol, filtered, washed with additional methanol and dried to give 3-(4-hydroxy-3-methyl-phenyl)-1-((1aS,5aR)-1,1,2-trimethyl-1,1a,5,5a-tetrahydro-3-thia-cyclopropa[a]pentalen-4-yl)-propenone (1.27 g) as an olive-green powder; LC-MS: $t_R$=1.09 min, [M+1]$^+$=339.23; $^1$H NMR (D$_6$-DMSO): δ 9.98 (s, 1H), 7.54-7.47 (m, 2H), 7.44-7.39 (m, 1H), 7.10 (d, J=15.8 Hz, 1H), 6.82 (d, J=8.2 Hz, 1H), 3.15 (dd, J=6.4, 18.8 Hz, 1H), 2.93 (d, J=18.8 Hz, 1H), 2.36 (s, 3H), 2.14 (s, 3H), 2.02-1.92 (m, 2H), 1.09 (s, 3H), 0.70 (s, 3H).

Intermediate 5

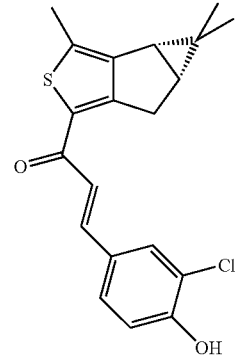

A solution of 3-chloro-4-hydroxy-benzaldehyde (888 mg, 5.67 mmol) and (1aS,5aR)-1-(1,1,2-trimethyl-1,1a,5,5a-tetrahydro-3-thia-cyclopropa[a]pentalen-4-yl)-ethanone (1.0 g, 4.54 mmol) in ethanol (50 mL) and approx. 6 N HCl in isopropanol (8 mL) is stirred at rt for 48 h. The dark blue solution is diluted with diethyl ether and washed with sat. aq. NaHCO$_3$ solution and water. The aq. phases are extracted with diethyl ether. The combined organic extracts are dried over MgSO$_4$ and evaporated. The crude product is suspended in methanol, filtered, washed with additional methanol and dried to give 3-(3-chloro-4-hydroxy-phenyl)-1-((1aS,5aR)-1,1,2-trimethyl-1,1a,5,5a-tetrahydro-3-thia-cyclopropa[a]pentalen-4-yl)-propenone (1.15 g) as a yellow powder; LC-MS: $t_R$=1.09 min, [M+1]$^+$=359.21; $^1$H NMR (D$_6$-DMSO): δ 10.82 (s, 1H), 7.82 (d, J=1.2 Hz, 1H), 7.56 (dd, J=1.2, 8.8 Hz, 1H), 7.50 (d, J=15.2 Hz, 1H), 7.17 (d, J=15.2 Hz, 1H), 7.00 (d, J=8.2 Hz, 1H), 3.15 (dd, J=7.0, 18.8 Hz, 1H), 2.95 (d, J=18.8 Hz, 1H), 2.37 (s, 3H), 2.03-1.92 (m, 2H), 1.10 (s, 3H), 0.69 (s, 3H).

Intermediate 4

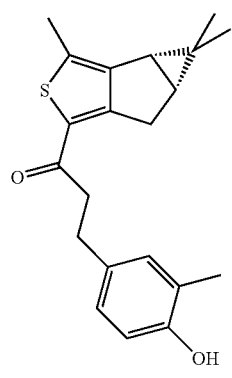

A mixture of 3-(4-hydroxy-3-methyl-phenyl)-1-((1aS,5aR)-1,1,2-trimethyl-1,1a,5,5a-tetrahydro-3-thia-cyclopropa[a]pentalen-4-yl)-propenone (1.27 g, 3.75 mmol) and Pd/C (400 mg, 10% Pd) in ethanol (50 mL) and THF (50 mL) is stirred at rt for 2 h under H$_2$ (1.5 bar). The mixture is filtered, the filtrate is evaporated and the crude product is purified by CC on silica gel eluting with heptane:EA 3:2 to give 3-(4-hydroxy-3-methyl-phenyl)-1-((1aS,5aR)-1,1,2-trimethyl-1,1a,5,5a-tetrahydro-3-thia-cyclopropa[a]pentalen-4-yl)-propan-1-one (1.13 g) as a yellow solid; LC-MS: $t_R$=1.07 min, [M+1]$^+$=341.26; $^1$H NMR (D$_6$-DMSO): δ 8.98

Intermediate 6

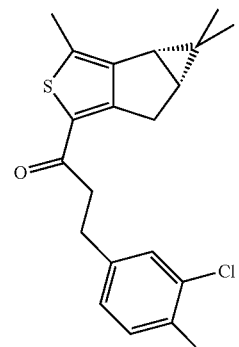

A mixture of 3-(3-chloro-4-hydroxy-phenyl)-1-((1aS,5aR)-1,1,2-trimethyl-1,1a,5,5a-tetrahydro-3-thia-cyclopropa[a]pentalen-4-yl)-propenone (1.11 g, 3.10 mmol) and Pd/C (400 mg, 10% Pd) in ethanol (50 mL) and THF (50 mL) is stirred at rt for 2.5 h under H$_2$ (1.5 bar). The mixture is filtered, the filtrate is evaporated and the crude product is purified by CC on silica gel eluting with heptane:EA 7:3 to give 3-(3-chloro-4-hydroxyphenyl)-1-((1aS,5aR)-1,1,2-trimethyl-1,1a,5,5a-tetrahydro-3-thia-cyclopropa[a]pentalen-4-yl)-propan-1-one (0.97 g) as a colourless solid; LC-MS:

$t_R$=1.08 min, [M+1]$^+$=361.22; $^1$H NMR (CDCl$_3$): δ 7.18 (d, J=1.8 Hz, 1H), 7.03 (dd, J=1.8, 8.2 Hz, 1H), 6.90 (d, J=8.2 Hz, 1H), 5.42 (s, 1H), 3.01-2.85 (m, 5H), 2.78 (d, J=18.8 Hz, 1H), 2.38 (s, 3H), 1.92-1.90 (m, 2H), 1.11 8s, 3H), 0.70 (s, 3H).

Intermediate 7

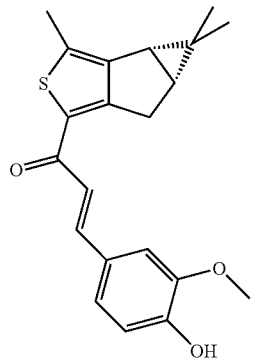

A solution of vanilline (432 mg, 2.84 mmol) and (1aS,5aR)-1-(1,1,2-trimethyl-1,1a,5,5a-tetrahydro-3-thia-cyclopropa[a]pentalen-4-yl)-ethanone (500 mg, 2.27 mmol) in ethanol (10 mL) and approx. 6 N HCl in isopropanol (3 mL) is stirred at rt for 18 h. The dark green solution is diluted with diethyl ether and washed with sat. aq. NaHCO$_3$ solution and water. The aq. phases are extracted with diethyl ether. The combined organic extracts are dried over MgSO$_4$ and evaporated. The crude product is purified by CC on silica gel eluting with heptane:EA 7:3 to give 3-(4-hydroxy-3-methoxy-phenyl)-1-((1aS,5aR)-1,1,2-trimethyl-1,1a,5,5a-tetrahydro-3-thia-cyclopropa[a]pentalen-4-yl)-propenone (0.775 g) as an olive foam; LC-MS: $t_R$=1.07 min, [M+1]$^+$=355.10; $^1$H NMR (CDCl$_3$): δ 7.68 (d, J=15.8 Hz, 1H), 7.21-7.16 (m, 1H), 7.10-7.02 (m, 2H), 6.94 (d, J=8.2 Hz, 1H), 5.86 (s, 1H), 3.94 (s, 3H), 3.12 (dd, J=5.3, 18.8 Hz, 1H), 2.93 (d, J=18.8 Hz, 1H), 2.42 (s, 3H), 1.96-1.88 (m, 2H), 1.12 (s, 3H), 0.74 (s, 3H).

Intermediate 8

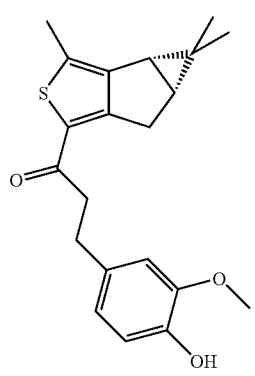

A mixture of 3-(4-hydroxy-3-methoxy-phenyl)-1-((1aS,5aR)-1,1,2-trimethyl-1,1a,5,5a-tetrahydro-3-thia-cyclopropa[a]pentalen-4-yl)-propenone (750 mg, 2.11 mmol) and Pd/C (200 mg, 10% Pd) in ethanol (30 mL) and THF (30 mL) is stirred at rt for 2.5 h under H$_2$ (1.5 bar). The mixture is filtered, the filtrate is evaporated and the crude product is purified by CC on silica gel eluting with heptane:EA 7:3 to give 3-(4-hydroxy-3-methoxy-phenyl)-1-((1aS,5aR)-1,1,2-trimethyl-1,1a,5,5a-tetrahydro-3-thia-cyclopropa[a]pentalen-4-yl)-propan-1-one (596 mg) as a colourless resin; LC-MS: $t_R$=1.05 min, [M+1]$^+$=357.30; $^1$H NMR (CDCl$_3$): δ 6.83 (d, J=7.6 Hz, 1H), 6.75-6.68 (m, 2H), 5.46 (s, 1H), 3.86 8s, 3H), 3.01-2.90 (m, 5H), 2.77 (d, J=18.8 Hz, 1H), 2.37 (s, 3H), 1.91-1.85 (m, 2H), 1.11 (s, 3H), 0.69 (s, 3H).

Intermediate 9

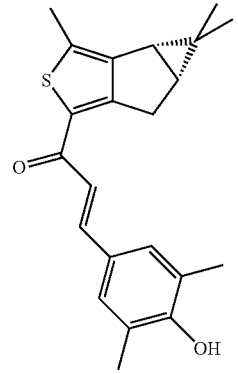

A solution of 3,5-dimethyl-4-hydroxybenzaldehyde (2.21 g, 14.7 mmol) and (1aS,5aR)-1-(1,1,2-trimethyl-1,1a,5,5a-tetrahydro-3-thia-cyclopropa[a]pentalen-4-yl)-ethanone (2.70 g, 12.3 mmol) in ethanol (50 mL) and approx. 6 N HCl in isopropanol (25 mL) is stirred at rt for 90 min. The dark brown solution is diluted with diethyl ether and washed with a 1:1 mixture of 1 N aq. NaOH and sat. aq. NaHCO$_3$ solution, and water. The aq. phases are extracted with diethyl ether. The combined organic extracts are dried over MgSO$_4$ and evaporated. The crude product is purified by CC on silica gel eluting with heptane:EA 7:3 to give 3-(3,5-dimethyl-4-hydroxy-phenyl)-1-((1aS,5aR)-1,1,2-trimethyl-1,1a,5,5a-tetrahydro-3-thia-cyclopropa[a]pentalen-4-yl)-propenone (3.28 g) as a yellow powder; LC-MS: $t_R$=1.12 min, [M+1]$^+$=353.31; $^1$H NMR (CDCl$_3$): δ 7.65 (d, J=15.8 Hz, 1H), (s, 2H), 7.06 (d, J=15.8 Hz, 1H), 5.08 (s, 1H), 3.12 (dd, J=5.9, 18.8, 1H), 2.95 (d, J=18.8 Hz, 1H), 2.41 (s, 3H), 2.28 (s, 6H), 1.96-1.89 (m, 2H), 1.13 (s, 3H), 0.75 (s, 3H).

Intermediate 10

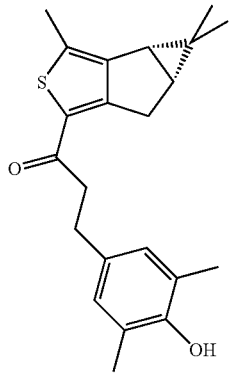

A mixture of 3-(3,5-dimethyl-4-hydroxy-phenyl)-1-((1aS,5aR)-1,1,2-trimethyl-1,1a,5,5a-tetrahydro-3-thia-cyclopropa[a]pentalen-4-yl)-propenone (3.0 g, 8.51 mmol) and Pd/C (500 mg, 10% Pd) in ethanol (50 mL) and THF (50 mL) is stirred at rt for 4 h under H$_2$ (1.5 bar). The mixture is filtered, the filtrate is evaporated and the crude product is purified by CC on silica gel eluting with heptane:EA 1:1 to give 3-(3,5-dimethyl-4-hydroxy-phenyl)-1-((1aS,5aR)-1,1,2-trimethyl-1,1a,5,5a-tetrahydro-3-thia-cyclopropa[a]pentalen-4-yl)-propan-1-one (3.0 g) as a yellow foam; LC-MS: $t_R$=1.11 min, [M+1]$^+$=355.33; $^1$H NMR (CDCl$_3$): δ 6.84 (s, 2H), 4.62 (s, 1H), 3.05-2.76 (m, 5H), 2.39 (s, 3H), 2.23 (s, 6H), 1.94-1.87 (m, 2H), 1.13 (s, 3H), 0.72 (s, 3H).

Intermediate 11

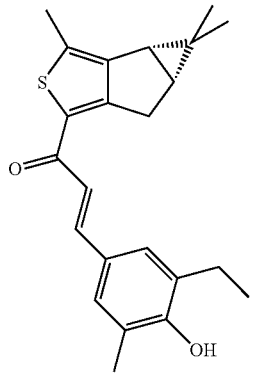

a) To an ice-cold solution of H$_2$SO$_4$ (150 mL) in water (250 mL) 2-ethyl-6-methylaniline (15.0 g, 111 mmol) is added. The solution is treated with ice (150 g) before a solution of NaNO$_2$ (10.7 g, 155 mmol) in water (150 mL) and ice (50 g) is added dropwise. The mixture is stirred at 0° C. for 1 h. 50% aq. H$_2$SO$_4$ (200 mL) is added and stirring is continued at rt for 18 h. The mixture is extracted with DCM, the organic extracts are dried over MgSO$_4$ and evaporated. The crude product is purified by CC on silica gel eluting with heptane:EA 9:1 to give 2-ethyl-6-methyl-phenol (8.6 g) as a crimson oil; LC-MS: $t_R$=0.89 min; $^1$H NMR (CDCl$_3$): δ 7.03-6.95 (m, 2H), 6.80 (t, J=7.6 Hz, 1H), 4.60 (s, 1H), 2.64 (q, J=7.6 Hz, 2H), 2.25 (s, 3H), 1.24 (t, J=7.6 Hz, 3H).

b) A solution of 2-ethyl-6-methyl-phenol (8.40 g, 61.7 mmol) and hexamethylene tetraamine (12.97 g, 92.5 mmol) in acetic acid (60 mL) and water (14 mL) is heated to 115° C. The water is distilled off at 117° C. and collected with a Dean-Stark apparatus. Then the water separator is replaced by a reflux condensor and the mixture is refluxed for 3 h. The mixture is cooled to rt, diluted with water (100 mL) and extracted with EA. The organic extract is washed with sat. aq. NaHCO$_3$, dried over MgSO$_4$ and evaporated. The remaining solid is dissolved in EA and treated with heptane to initialize crystallisation. The solid material is collected and dried to give 3-ethyl-4-hydroxy-5-methyl-benzaldehyde (3.13 g) as a colourless crystalline powder, $^1$H NMR (CDCl$_3$): δ 9.83 (s, 1H), 7.58-7.53 (m, 2H), 5.30 (s br, 1H), 2.69 (q, J=7.6 Hz, 2H), 2.32 (s, 3H), 1.28 (t, J=7.6 Hz, 3H).

c) A solution of 3-ethyl-4-hydroxy-5-methyl-benzaldehyde (2.00 g, 12.2 mmol) and (1aS,5aR)-1-(1,1,2-trimethyl-1,1a,5,5a-tetrahydro-3-thia-cyclopropa[a]pentalen-4-yl)-ethanone (2.15 g, 9.75 mmol) in ethanol (13 mL) and approx. 6 N HCl in isopropanol (6 mL) is stirred at rt for 16 h. The precipitate that forms is collected, washed with a small amount of methanol and dried to give 3-(3-ethyl-4-hydroxy-5-methylphenyl)-1-((1aS,5aR)-1,1,2-trimethyl-1,1a,5,5a-tetrahydro-3-thia-cyclopropa[a]pentalen-4-yl)-propenone (2.55 g) as a green powder; LC-MS: $t_R$=1.15 min, [M+1]$^+$=367.25; $^1$H NMR (CDCl$_3$): δ 7.69 (d, J=15.2 Hz, 1H), 7.28 (s, 2H), 7.06 (d, J=15.2 Hz, 1H), 4.94 (s, 1H), 3.12 (dd, J=5.9, 18.8 Hz, 1H), 2.94 (d, J=18.8 Hz, 1H), 2.66 (q, J=7.6 Hz, 2H), 2.42 (s, 3H), 2.29 (s, 3H), 1.96-1.89 (m, 2H), 1.30-1.20 (m, 3H), 1.13 (s, 3H), 0.75 (s, 3H).

Intermediate 12

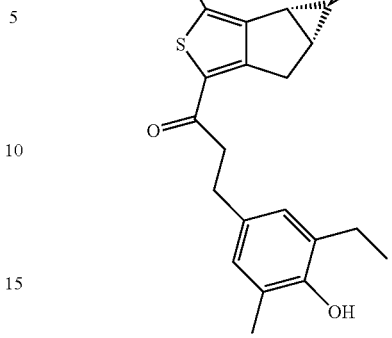

A mixture of 3-(3-ethyl-4-hydroxy-5-methylphenyl)-1-((1aS,5aR)-1,1,2-trimethyl-1,1a,5,5a-tetrahydro-3-thia-cyclopropa[a]pentalen-4-yl)-propenone (2.50 g, 6.82 mmol) and Pd/C (600 mg, 10% Pd) in methanol (10 mL) and THF (20 mL) is stirred at rt for 10 h under H$_2$ (approx. 2 bar). The mixture is filtered, the filtrate is evaporated and the crude product is purified by CC on silica gel eluting with heptane:EA 4:1 to give 3-(3-ethyl-4-hydroxy-5-methylphenyl)-1-((1aS,5aR)-1,1,2-trimethyl-1,1a,5,5a-tetrahydro-3-thia-cyclopropa[a]pentalen-4-yl)-propan-1-one (2.20 g) as a yellow oil; LC-MS: $t_R$=1.13 min, [M+1]$^+$=369.25; $^1$H NMR (CDCl$_3$): δ 6.84 (s, 2H), 4.52 (s, 1H), 3.01-2.84 (m, 5H), 2.78 (d, J=18.8 HZ, 1H), 2.59 (q, J=7.6 Hz, 2H), 2.37 (s, 3H), 2.22 (s, 3H), 1.91-1.85 (m, 2H), 1.22 (t, J=7.6 Hz, 3H), 1.11 (s, 3H), 0.70 (s, 3H).

Intermediate 13

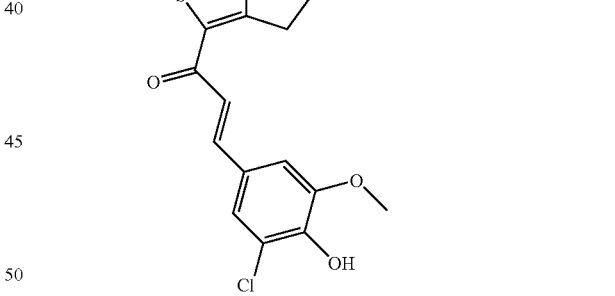

A solution of 3-chloro-4-hydroxy-5-methoxy-benzaldehyde (3.05 g, 16.3 mmol) and (1aS,5aR)-1-(1,1,2-trimethyl-1,1a,5,5a-tetrahydro-3-thia-cyclopropa[a]pentalen-4-yl)-ethanone (3.0 g, 13.6 mmol) in ethanol (50 mL) and approx. 6 N HCl in isopropanol (25 mL) is stirred at 55° C. for 2 h. The dark brown solution is diluted with diethyl ether and washed with a 1:1 mixture of 1 N aq. NaOH and sat. aq. NaHCO$_3$ solution, and water. The aq. phases are extracted with diethyl ether. The combined organic extracts are dried over MgSO$_4$ and evaporated. The crude product is purified by CC on silica gel eluting with heptane:EA 7:3 to give 3-(3-chloro-4-hydroxy-5-methoxyphenyl)-1-((1aS,5aR)-1,1,2-trimethyl-1,1a,5,5a-tetrahydro-3-thia-cyclopropa[a]pentalen-4-yl)-propenone (4.24 g) as a green-yellow foam; LC-MS: $t_R$=1.12 min, [M+1]$^+$=389.07.

Intermediate 14

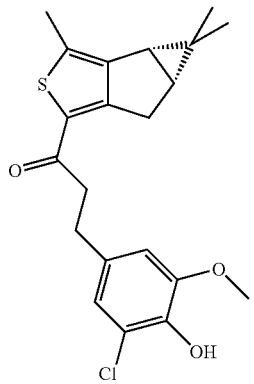

A mixture of 3-(3-chloro-4-hydroxy-5-methoxy-phenyl)-1-((1aS,5aR)-1,1,2-trimethyl-1,1a,5,5a-tetrahydro-3-thia-cyclopropa[a]pentalen-4-yl)-propenone (4.24 g, 10.9 mmol) and Pd/C (800 mg, 10% Pd) in ethanol (50 mL) and THF (50 mL) is stirred at rt for 7 h under $H_2$ (1.5 bar). The mixture is filtered, the filtrate is evaporated and the crude product is purified by CC on silica gel eluting with heptane:EA 1:1 to give 3-(3-chloro-4-hydroxy-5-methoxy-phenyl)-1-((1aS,5aR)-1,1,2-trimethyl-1,1a,5,5a-tetrahydro-3-thia-cyclopropa[a]pentalen-4-yl)-propan-1-one (3.15 g) as a yellow foam; LC-MS: $t_R$=1.10 min, [M+1]$^+$=391.14; $^1$H NMR (CDCl$_3$): δ 6.80 (d, J=1.8 Hz, 1H), 6.65 (d, J=1.8 Hz, 1H), 5.68 (s, 1H), 3.87 (s, 3H), 3.05-2.85 (m, 5H), 2.77 (d, J=18.8 Hz, 1H), 2.38 8s, 3H), 1.92-1.85 (m, 2H), 1.11 (s, 3H), 0.70 (s, 3H).

Intermediate 15

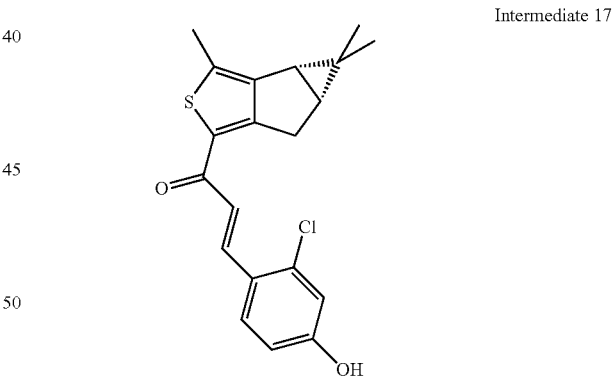

A solution of 3,5-dimethoxy-4-hydroxybenzaldehyde (517 mg, 2.84 mmol) and (1aS,5aR)-1-(1,1,2-trimethyl-1,1a,5,5a-tetrahydro-3-thia-cyclopropa[a]pentalen-4-yl)-ethanone (500 mg, 2.27 mmol) in ethanol (25 mL) and approx. 6 N HCl in isopropanol (4 mL) is stirred at rt for 24 h. The dark brown solution is diluted with diethyl ether and washed with a 1:1 mixture of 1 N aq. NaOH and sat. aq. NaHCO$_3$ solution, and water. The aq. phases are extracted with diethyl ether. The combined organic extracts are dried over MgSO$_4$ and evaporated. The crude product is purified by CC on silica gel eluting with heptane:EA 7:3 to give 3-(3,5-dimethoxy-4-hydroxy-phenyl)-1-((1aS,5aR)-1,1,2-trimethyl-1,1a,5,5a-tetrahydro-3-thia-cyclopropa[a]pentalen-4-yl)-propenone (890 mg) as a dark orange foam; LC-MS: $t_R$=1.06 min, [M+1]$^+$=385.28; $^1$H NMR (CDCl$_3$): δ 7.66 (d, J=15.2 Hz, 1H), 7.04 (d, J=15.2 Hz, 1H), 6.84 (s, 2H), 5.78 (s, 1H), 3.95 (s, 6H), 3.12 (dd, J=5.9, 18.8, 1H), 2.93 (d, J=18.8 Hz, 1H), 2.42 (s, 3H), 1.98-1.89 (m, 2H), 1.14 (s, 3H), 0.75 (s, 3H).

Intermediate 16

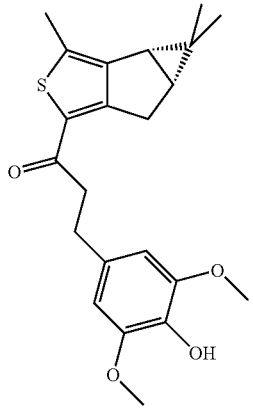

A mixture of 3-(3,5-dimethoxy-4-hydroxy-phenyl)-1-((1aS,5aR)-1,1,2-trimethyl-1,1a,5,5a-tetrahydro-3-thia-cyclopropa[a]pentalen-4-yl)-propenone (890 mg, 2.32 mmol) and Pd/C (200 mg, 10% Pd) in ethanol (30 mL) and THF (30 mL) is stirred at rt for 3.5 h under $H_2$ (1.5 bar). The mixture is filtered, the filtrate is evaporated and the crude product is purified by CC on silica gel eluting with heptane:EA 1:1 to give 3-(3,5-dimethoxy-4-hydroxy-phenyl)-1-((1aS,5aR)-1,1,2-trimethyl-1,1a,5,5a-tetrahydro-3-thia-cyclopropa[a]pentalen-4-yl)-propan-1-one (700 mg) as a pale yellow foam; LC-MS: $t_R$=1.04 min, [M+1]$^+$=387.29; $^1$H NMR (CDCl$_3$): δ 6.44 (s, 2H), 5.36 (s, 1H), 3.86 (s, 6H), 3.01-2.90 (m, 5H), 2.37 (s, 3H), 1.91-1.85 (m, 2H), 1.10 (s, 3H), 0.69 (s, 3H).

Intermediate 17

A solution of 2-chloro-4-hydroxybenzaldehyde (1000 mg, 6.39 mmol) and (1aS,5aR)-1-(1,1,2-trimethyl-1,1a,5,5a-tetrahydro-3-thia-cyclopropa[a]pentalen-4-yl)-ethanone (938 mg, 4.26 mmol) in ethanol (10 mL) and approx. 6 N HCl in isopropanol (6 mL) is stirred at rt for 28 h. The dark yellow-brown solution is diluted with diethyl ether and washed with sat. aq. NaHCO$_3$ solution and water. The aq. phases are extracted with diethyl ether. The combined organic extracts are dried over MgSO$_4$ and evaporated. The crude product is suspended in methanol, stirred at rt for 15 min, filtered, washed with additional methanol and dried to give 3-(2-chloro-4-hydroxy-phenyl)-1-((1aS,5aR)-1,1,2-trimethyl-1,1a,5,5a-tetrahydro-3-thia-cyclopropa[a]pentalen-4-yl)-propenone (968 mg) as a yellow powder; LC-MS: $t_R$=1.11 min, $[M+1]^+$=359.84; $^1$H NMR (CDCl$_3$): δ 8.09 (d, J=15.8 Hz, 1H), 7.61 (d, J=8.8 Hz, 1H), 7.12 (d, J=15.8 Hz, 1H), 6.95 (d, J=2.3 Hz, 1H), 6.80 (dd, J=2.3, 8.2 Hz, 1H), 5.63 (s, 1H), 3.12 (dd, J=5.2, 18.8 Hz, 1H), 2.93 (d, J=18.8 Hz, 1H), 2.42 (s, 3H), 1.97-1.89 (m, 2H), 1.13 (s, 3H), 0.74 (s, 3H).

Intermediate 18

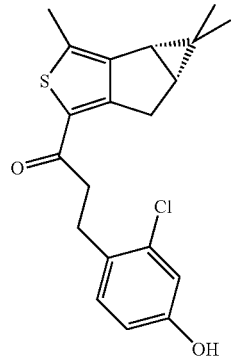

A mixture of 3-(2-chloro-4-hydroxy-phenyl)-1-((1aS, 5aR)-1,1,2-trimethyl-1,1a,5,5a-tetrahydro-3-thia-cyclopropa[a]pentalen-4-yl)-propenone (965 mg, 2.69 mmol) and Pd/C (400 mg, 10% Pd) in ethanol (40 mL) and THF (40 mL) is stirred at rt for 4 h under H$_2$ (1.5 bar). The mixture is filtered, the filtrate is evaporated and the crude product is purified by CC on silica gel eluting with heptane:EA 3:1 to give 3-(2-chloro-4-hydroxy-phenyl)-1-((1aS,5aR)-1,1,2-trimethyl-1,1a,5,5a-tetrahydro-3-thia-cyclopropa[a]pentalen-4-yl)-propan-1-one (858 mg) as a pale yellow solid; LC-MS: $t_R$=1.10 min, $[M+1]^+$=361.19; $^1$H NMR (CDCl$_3$): δ 7.13 (d, J=8.2 Hz, 1H), 6.86 (d, J=2.3 Hz, 1H), 6.66 (dd, J=2.3, 8.2 Hz, 1H), 4.80 (s, 1H), 3.08-2.90 (m, 2H), 2.78 (d, J=18.8 Hz, 1H), 2.37 (s, 3H), 1.92-1.84 (m, 2H), 1.10 (s, 3H), 0.70 (s, 3H).

Intermediate 19

A solution of 4-hydroxy-2-methoxybenzaldehyd (1.55 g, 10.2 mmol), (1aS,5aR)-1-(1,1,2-trimethyl-1,1a,5,5a-tetrahydro-3-thia-cyclopropa[a]pentalen-4-yl)-ethanone (1.50 g, 6.81 mmol), NaOH (10.4 g, 259 mmol) in methanol (50 mL) is stirred at 75° C. for 3 h. The reaction mixture is diluted with water and the pH is adjusted to pH 8 with 1 N aq. HCl and sat. aq. NaHCO$_3$ solution. The mixture is extracted with diethyl ether (3×200 mL). The organic extracts are washed with water (2×150 mL), dried over MgSO$_4$ and evaporated. The crude product is purified by CC on silica gel eluting with heptane:EA 7:3 to give 3-(4-hydroxy-2-methoxy-phenyl)-1-((1aS,5aR)-1,1,2-trimethyl-1,1a,5,5a-tetrahydro-3-thia-cyclopropa[a]pentalen-4-yl)-propenone (2.23 g) as a yellow foam; LC-MS: $t_R$=1.06 min, $[M+1]^+$=355.26.

Intermediate 20

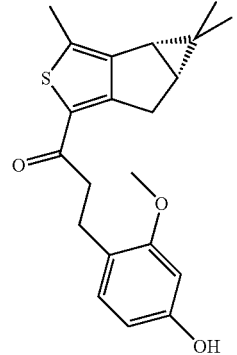

A mixture of 3-(4-hydroxy-2-methoxy-phenyl)-1-((1aS, 5aR)-1,1,2-trimethyl-1,1a,5,5a-tetrahydro-3-thia-cyclopropa[a]pentalen-4-yl)-propenone (2.58 g, 7.28 mmol) and Pd/C (500 mg, 10% Pd) in ethanol (50 mL) and THF (50 mL) is stirred at rt for 3 h under H$_2$ (1.5 bar). The mixture is filtered, the filtrate is evaporated and the crude product is purified by CC on silica gel eluting with heptane:EA 4:1 to give 3-(4-hydroxy-2-methoxy-phenyl)-1-((1aS,5aR)-1,1,2-trimethyl-1,1a,5,5a-tetrahydro-3-thia-cyclopropa[a]pentalen-4-yl)-propan-1-one (1.31 g) as a very pale orange foam; LC-MS: $t_R$=1.05 min, $[M+1]^+$=357.27; $^1$H NMR (CDCl$_3$): δ 7.00 (d, J=8.2 Hz, 1H), 6.40 (d, J=1.8 Hz, 1H), 6.32 (dd, J=1.8, 8.2 Hz, 1H), 4.82 (s, 1H), 3.78 (s, 3H), 3.04-2.88 (m, 5H), 2.78 (d, J=18.8 Hz, 1H), 2.37 (s, 3H), 190-1.84 (m, 2H), 1.11 (s, 3H), 0.70 (s, 3H).

Intermediate 21

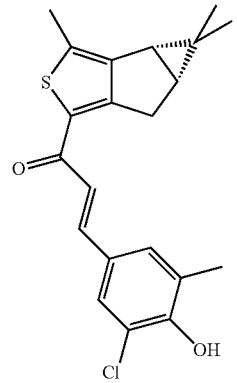

A solution of 3-chloro-4-hydroxy-5-methyl-benzaldehyde (341 mg, 2.00 mmol) and (1aS,5aR)-1-(1,1,2-trimethyl-1,1a, 5,5a-tetrahydro-3-thia-cyclopropa[a]pen-talen-4-yl)-ethanone (220 mg, 1.00 mmol) in ethanol (6 mL) and 0.8 mL conc. H$_2$SO$_4$ is stirred at rt for 35 min, then at 50° C. for 1 h. The dark brown solution is diluted with acetonitrile (1 mL) and separated by prep. HPLC (Phenomenex Aqua, 75×30 mm ID, 10 μm, 10 to 95% acetonitrile in water containing 0.5% formic acid) to give 3-(3-chloro-4-hydroxy-5-methyl-phenyl)-1-((1aS,5aR)-1,1,2-trimethyl-1,1a,5,5a-tetrahydro-3-thia-cyclopropa[a]pentalen-4-yl)-propenone (180 mg) as a yellow solid; LC-MS: $t_R$=1.14 min, $[M+1]^+$=373.25.

Intermediate 22

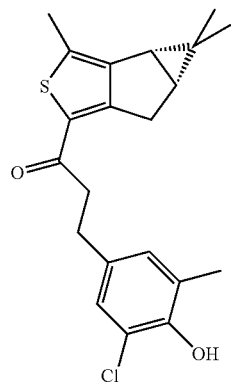

A mixture of 3-(3-chloro-4-hydroxy-5-methyl-phenyl)-1-((1aS,5aR)-1,1,2-trimethyl-1,1a,5,5a-tetrahydro-3-thia-cyclopropa[a]pentalen-4-yl)-propenone (177 mg, 0.475 mmol) and Pd/C (150 mg, 10% Pd) in ethanol (5 mL) is stirred at rt for 24 h under $H_2$ (1.0 bar). The mixture is filtered, the filtrate is evaporated and the crude product is purified by prep. HPLC (Phenomenex Aqua, 75×30 mm ID, 10 μm, 10 to 95% acetonitrile in water containing 0.5% formic acid) to give 3-(3-chloro-4-hydroxy-5-methyl-phenyl)-1-((1aS,5aR)-1,1,2-trimethyl-1,1a,5,5a-tetrahydro-3-thia-cyclopropa[a]pentalen-4-yl)-propan-1-one (170 g) as brownish resin; LC-MS: $t_R$=1.12 min, [M+1]$^+$=375.24; $^1$H NMR (CDCl$_3$): δ 7.01 (d, J=2.3 Hz, 1H), 6.89 8d, J=2.3 Hz, 1H), 5.45 (s, 1H), 3.02-2.85 (m, 5H), 2.77 (d, J=18.8 Hz, 1H), 2.38 (s, 3H), 2.24 (s, 3H), 1.91-1.87 (m, 2H), 0.70 (s, 6H).

Intermediate 23

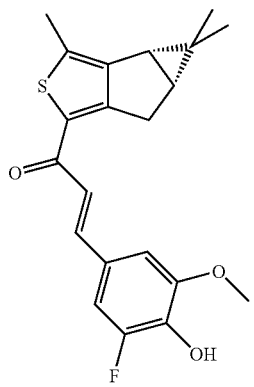

A solution of (1aS,5aR)-1-(1,1,2-trimethyl-1,1a,5,5a-tetrahydro-3-thia-cyclopropa[a]pen-talen-4-yl)-ethanone (440 mg, 2.0 mmol) and 3-fluoro-4-hydroxy-5-methoxybenzaldehyde (680 mg, 4.0 mmol) in ethanol (5 mL) and 5 N HCl in isopropanol (2.5 mL) is stirred at rt for 95 min and then at 45° C. for 30 min. The mixture is diluted with ice/water (100 mL) and sat. aq. NaHCO$_3$ (40 mL), the pH is adjusted to pH 10 by adding 2 N aq. NaOH, and extracted with diethyl ether. The organic extract is dried over Na$_2$SO$_4$ and the solvent is removed in vacuo. The crude product is purified by prep. HPLC (Phenomenex Aqua, 75×30 mm ID, 10 μm, 10 to 95% acetonitrile in water containing 0.5% formic acid) to give 3-(3-fluoro-4-hydroxy-5-methoxy-phenyl)-1-((1aS,5aR)-1,1,2-trimethyl-1,1a,5,5a-tetrahydro-3-thia-cyclopropa[a]pentalen-4-yl)-propenone (480 mg) as a yellow resin; LC-MS: $t_R$=1.08 min, [M+1]$^+$=373.29.

Intermediate 24

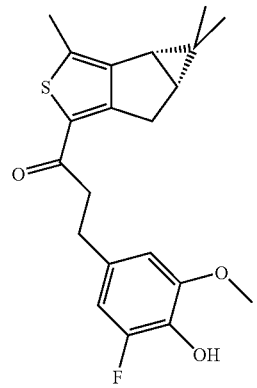

A solution of 3-(3-fluoro-4-hydroxy-5-methoxy-phenyl)-1-((1aS,5aR)-1,1,2-trimethyl-1,1a,5,5a-tetrahydro-3-thia-cyclopropa[a]pentalen-4-yl)-propenone (465 mg, 1.25 mmol) in ethanol (12 mL) is treated with Pd/C (400 mg, 10% Pd) and the mixture is stirred at rt for 36 h under 1 bar H$_2$. The mixture is filtered, the filtrate is evaporated and the crude product is purified by prep. HPLC (Phenomenex Aqua, 75×30 mm ID, 10 μm, 10 to 95% acetonitrile in water containing 0.5% formic acid) to give 3-(3-fluoro-4-hydroxy-5-methoxy-phenyl)-1-((1aS,5aR)-1,1,2-trimethyl-1,1a,5,5a-tetrahydro-3-thia-cyclopropa[a]pentalen-4-yl)-propan-1-one (210 mg) as a beige resin; LC-MS: $t_R$=1.06 min, [M+1]$^+$=375.22.

Intermediate 25

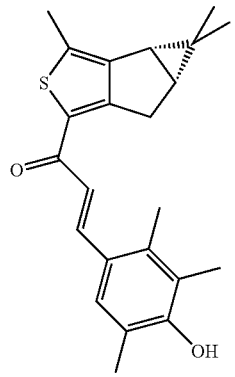

A solution of (1aS,5aR)-1-(1,1,2-trimethyl-1,1a,5,5a-tetrahydro-3-thia-cyclopropa[a]pen-talen-4-yl)-ethanone (440 mg, 2.0 mmol) and 4-hydroxy-2,3,5-trimethylbenzaldehyde (660 mg, 4.0 mmol) in ethanol (5 mL) and 5 N HCl in isopropanol (2.5 mL) is stirred at rt for 35 min. The mixture is diluted with ice/water (60 mL) and sat. aq. NaHCO$_3$ (20 mL), the pH is adjusted to pH 12 by adding 2 N aq. NaOH, and extracted with diethyl ether. The organic extract is dried over Na$_2$SO$_4$ and the solvent is removed in vacuo. The crude product is purified by prep. HPLC (Phenomenex Aqua, 75×30 mm ID, 10 μm, 10 to 95% acetonitrile in water containing 0.5% formic acid) to give 3-(4-hydroxy-2,3,5-trimethyl-phenyl)-1-((1aS,5aR)-1,1,2-trimethyl-1,1a,5,5a-tetrahydro-3-thia-cyclopropa[a]pentalen-4-yl)-propenone (710 mg) as a brown solid; LC-MS: $t_R$=1.14 min, [M+1]$^+$=367.31.

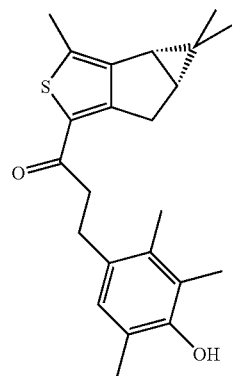

Intermediate 26

A solution of 3-(4-hydroxy-2,3,5-trimethyl-phenyl)-1-((1aS,5aR)-1,1,2-trimethyl-1,1a,5,5a-tetrahydro-3-thia-cyclopropa[a]pentalen-4-yl)-propenone (372 mg, 1.01 mmol) in ethanol (15 mL) is treated with Pd/C (250 mg, 10% Pd) and the mixture is stirred at rt for 36 h under 1 bar $H_2$. The mixture is filtered, the filtrate is evaporated to give 3-(4-hydroxy-2,3,5-trimethyl-phenyl)-1-((1aS,5aR)-1,1,2-trimethyl-1,1a,5,5a-tetrahydro-3-thia-cyclopropa[a]pentalen-4-yl)-propan-1-one (370 mg) as a brown resin; LC-MS: $t_R$=1.13 min, [M+1]$^+$= 369.29.

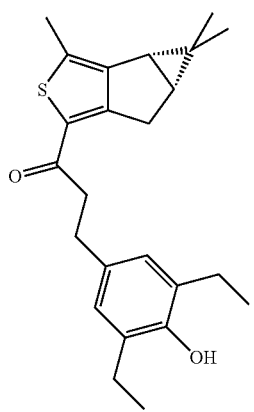

Intermediate 27

A solution of (1aS,5aR)-1-(1,1,2-trimethyl-1,1a,5,5a-tetrahydro-3-thia-cyclopropa[a]pen-talen-4-yl)-ethanone (890 mg, 4.04 mmol) and 3,5-diethyl-4-hydroxy-benzaldehyde (900 mg, 5.05 mmol, Lit: G. Trapani, A. Latrofa, M. Franco, C. Altomare, E. Sanna, M. Usal, G. Biggio, G. Liso *J. Med. Chem.* 41 (1998) 1846-1854; G. G. Ecke, J. P. Napolitano, A. H. Bilbey, A. J. Kolka, *J. Org. Chem.* 22 (1957) 639-642) in ethanol (7.5 mL) and 5 N HCl in isopropanol (2.5 mL) is stirred at rt for 72 h. The mixture is diluted with EA and is washed with water. The sovent of the organic layer is evaporated, the residue is dissolved in ethanol, treated with Pd/C (200 mg, 10% Pd) and stirred at rt for 18 h under 1.8 bar $H_2$. The mixture is filtered, the filtrate is concentrated and the crude product is purified by CC on silica gel eluting with heptane:EA 8:2 to give 3-(3,5-diethyl-4-hydroxy-phenyl)-1-((1aS,5aR)-1,1,2-trimethyl-1,1a,5,5a-tetrahydro-3-thia-cyclopropa[a]pentalen-4-yl)-propan-1-one (1.05 g) as a yellow oil; LC-MS: $t_R$=1.15 min, [M+1]$^+$=383.25.

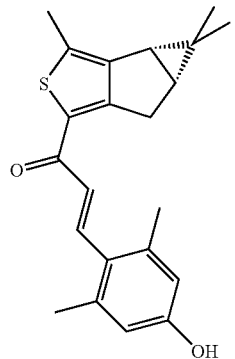

Intermediate 28

A solution of (1aS,5aR)-1-(1,1,2-trimethyl-1,1a,5,5a-tetrahydro-3-thia-cyclopropa[a]pen-talen-4-yl)-ethanone (606 mg, 2.75 mmol) and 2,6-diemthyl-4-hydroxybenzaldehyde (680 mg, 4.5 mmol) in ethanol (9 mL) and 5 N HCl in isopropanol (9 mL) is stirred at rt for 60 min. The mixture is diluted with ice/water (100 mL) and sat. aq. $NaHCO_3$ (40 mL), the pH is adjusted to pH 10 by adding 2 N aq. NaOH, and extracted with diethyl ether. The organic extract is dried over $Na_2SO_4$ and the solvent is removed in vacuo to give crude 3-(4-hydroxy-2,6-dimethyl-phenyl)-1-((1aS,5aR)-1,1,2-trimethyl-1,1a,5,5a-tetrahydro-3-thia-cyclopropa[a]pentalen-4-yl)-propenone (930 mg) as a dark green solid; LC-MS: $t_R$=1.09 min, [M+1]$^+$=353.26.

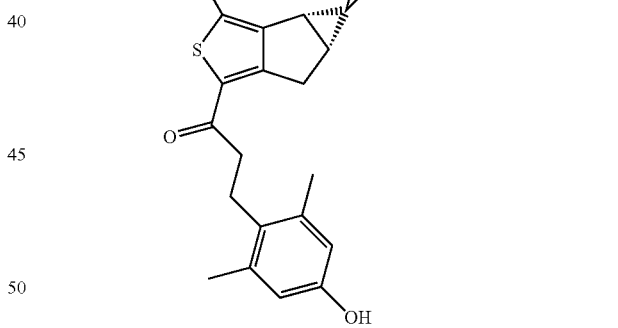

Intermediate 29

A solution of 3-(4-hydroxy-2,6-dimethyl-phenyl)-1-((1aS,5aR)-1,1,2-trimethyl-1,1a,5,5a-tetrahydro-3-thia-cyclopropa[a]pentalen-4-yl)-propenone (880 mg, 2.50 mmol) in ethanol (10 mL) is treated with Pd/C (400 mg, 10% Pd) and the mixture is stirred at rt for 4 days under 1 bar $H_2$. The mixture is filtered over celite, the filtrate is evaporated and the crude product is purified by prep. HPLC (Phenomenex Aqua, 75×30 mm ID, 10 µm, 10 to 95% acetonitrile in water containing 0.5% formic acid) to give 3-(4-hydroxy-2,6-dimethyl-phenyl)-1-((1aS,5aR)-1,1,2-trimethyl-1,1a,5,5a-tetrahydro-3-thia-cyclopropa[a]pentalen-4-yl)-propan-1-one (500 mg) as a beige resin; LC-MS: $t_R$=1.08 min, [M+1]$^+$= 355.24; $^1$H NMR (CDCl$_3$): δ 6.52 (s, 2H), 4.57 (s br, 1H), 3.00-2.90 (m, 3H), 2.81-2.73 (m, 3H), 2.38 (s, 3H), 2.28 (s, 6H), 1.90-1.86 (m, 2H), 1.11 (s, 3H), 0.70 (s, 3H).

Example 1

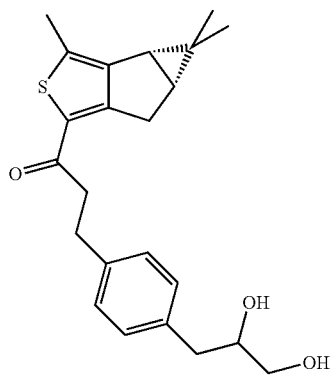

a) At 5° C., a solution of allylbromide (5.64 g, 46.6 mmol) in THF (40 mL) is slowly added to the Grignard reagent freshly prepared from 1,4-dibromobenzene (10.0 g, 42.4 mmol) and Mg-turnings (1.13 g, 46.6 mmol) in THF. The reaction mixture becomes slightly warm and a fine precipitate forms. Upon completion of the addition, the suspension is stirred at rt for 1 h before it is diluted with diethyl ether and washed with two portions of 1 N aq. HCl and one portion of water. The wash solutions are extracted twice with diethyl ether. The organic extracts are combined, dried over $MgSO_4$ and evaporated. The crude product is purified by CC on silica gel eluting with heptane:EA 9:1 to give 1-allyl-4-bromo-benzene (5.50 g) as a colourless oil.

b) A solution of 1-allyl-4-bromo-benzene (2.0 g, 10.2 mmol) in acetone (60 mL) is treated with $OsO_4$ (52 mg, 0.20 mmol), NMO (1.44 g, 12.2 mmol) and water (approx. 0.3 mL). The clear solution is stirred at rt for 2 h, diluted with DCM (150 mL) and washed twice with 10% aq. citric acid (2×75 mL). The aqueous phase is extracted twice with DCM. The organic extracts are combined, dried over $MgSO_4$ and evaporated. The crude product is purified by CC on silica gel eluting with EA to give 3-(4-bromo-phenyl)-propane-1,2-diol (1.41 g) as an almost colourless oil; LC-MS: $t_R$=0.72 min; $^1$H NMR ($CDCl_3$): δ 7.46-7.40 (m, 2H), 7.14-7.08 (m, 2H), 3.96-3.87 (m, 1H), 3.73-3.67 (m, 1H), 3.55-3.47 (m, 1H), 2.81-2.67 (m, 2H), 1.90 (s br, 2H).

c) A solution of 3-(4-bromo-phenyl)-propane-1,2-diol (1.41 g, 6.10 mmol) and p-toluenesulfonic acid (50 mg) in DMF (10 mL), 2,2-dimethoxypropane (10 mL) is stirred at rt for 2 h. The reaction mixture is diluted with sat. aq. $NaHCO_3$ (150 mL) and extracted with diethyl ether (2×200 mL). The organic extracts are washed with water (200 mL), dried over $MgSO_4$ and evaporated to give 4-(4-bromo-benzyl)-2,2-dimethyl-[1,3]dioxolane (1.57 g) as a pale brownish oil; LC-MS: $t_R$=1.00 min.

d) At −78° C. buthyllithium (3.98 mL, 6.37 mmol, 1.6 M solution in hexanes) is added to a solution of 4-(4-bromo-benzyl)-2,2-dimethyl-[1,3]dioxolane (1.57 g, 5.79 mmol) in THF (50 mL). The reaction mixture is stirred at −78° C. for 2 h before DMF is slowly added (2.12 g, 28.95 mmol). Stirring is continued for 30 min at −78° C., then at rt for 1 h. The mixture is diluted with diethyl ether (200 mL) and washed with sat. aq. $NaHCO_3$ and water. The organic layer is dried over $MgSO_4$ and evaporated to leave 4-(2,2-dimethyl-[1,3] dioxolan-4-ylmethyl)-benzaldehyde (1.29 g) as a pale brownish oil; LC-MS: $t_R$=0.87 min; $^1$H NMR ($CDCl_3$): δ 9.98 (s, 1H), 7.84-7.79 (m, 2H), 7.47-7.37 (m, 2H), 4.35 (p, J=6.4 Hz, 1H), 4.02 (dd, J=5.9, 8.2 Hz, 1H), 3.65 (dd, J=7.0, 8.2 Hz, 1H), 3.04 (dd, J=7.0, 14.1 Hz, 1H), 2.90 (dd, J=5.9, 13.5 Hz, 1H9, 1.44 8s, 3H), 1.36 (s, 3H).

e) A solution of 4-(2,2-dimethyl-[1,3]dioxolan-4-ylmethyl)-benzaldehyde (264 mg, 1.2 mmol) and (1aS,5aR)-1-(1,1,2-trimethyl-1,1a,5,5a-tetrahydro-3-thia-cyclopropa[a] pentalen-4-yl)-ethanone (220 mg, 1.0 mmol) in ethanol (5 mL) and approx. 6 N HCl in isopropanol is stirred at rt for 18 h, then at 50° C. for 4 h. The dark green solution is diluted with water and extracted three times with EA. The organic extracts are washed with brine, dried over $MgSO_4$ and evaporated. The crude product is purified by CC on silica gel eluting with heptane:EA 1:4 to give 3-[4-((2S/R)-2,3-dihydroxy-propyl)-phenyl]-1-((1aS,5aR)-1,1,2-trimethyl-1,1a,5,5a-tetrahydro-3-thia-cyclopropa[a]pentalen-4-yl)-propenone (230 mg) as a yellow oil; LC-MS: $t_R$=0.99 min, $[M+1]^+$=383.31.

f) A mixture of 3-[4-((2S/R)-2,3-dihydroxy-propyl)-phenyl]-1-((1aS,5aR)-1,1,2-trimethyl-1,1a,5,5a-tetrahydro-3-thia-cyclopropa[a]pentalen-4-yl)-propenone (230 mg, 0.60 mmol) and Pd/C (40 mg, 10% Pd) in ethanol (5 mL) and THF (5 mL) is stirred at rt for 5 h under $H_2$ (1.5 bar). The mixture is filtered, the filtrate is evaporated and the crude product is purified by CC on silica gel eluting with heptane:EA 1:4 followed by prep. HPLC to give 3-[4-((2S/R)-2,3-dihydroxy-propyl)-phenyl]-1-((1aS,5aR)-1,1,2-trimethyl-1,1a,5,5a-tetrahydro-3-thia-cyclopropa[a]pentalen-4-yl)-propan-1-one (60 mg) as a pale yellow resin; LC-MS: $t_R$=0.99 min, $[M+1]^+$= 385.29; $^1$H NMR ($CDCl_3$): δ 7.22-7.10 (m, 4H), 3.97-3.88 (m, 1H), 3.70 (dd, J=2.9, 10.6 Hz, 1H), 3.53 (dd, J=7.0, 11.1 Hz, 1H), 3.05-2.90 (m, 6H), 2.82-2.67 (m, 2H), 2.37 (s, 3H), 2.00 (s br, 1H), 1.92-1.85 (m, 2H), 1.10 (s, 3H), 0.70 (s, 3H).

Examples 2 to 11

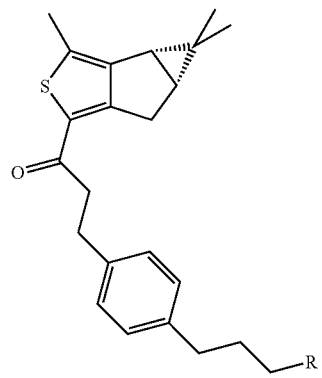

a) A mixture of 4-formyl cinnamic acid (2.82 g, 16.0 mmol) and Pd/C (350 mg, 10% Pd) in ethanol (120 mL) and DIPEA (3 mL) is stirred at rt for 2 h under 1.0 bar $H_2$. The reaction mixture is filtered and the filtrate is evaporated to give 3-(4-hydroxymethyl-phenyl)-propionic acid (2.18 g) as a colourless oil; LC-MS: $t_R$=0.62 min.

b) To a suspension of $LiAlH_4$ (155 mg, 4.0 mmol) in THF (25 mL) a solution of 3-(4-hydroxymethyl-phenyl)-propionic acid (720 mg, 4.0 mmol) in THF (20 mL) is added within 2 min. The resulting mixture is stirred at 70° C. for 80 min before it is treated with sat. aq. $NH_4Cl$ solution (10 mL). The suspension is filtered over celite, the filtrate is diluted with water (200 mL) and extracted with diethyl ether (2×75 mL) followed by EA (2×75 mL). The organic extracts are combined, dried over $Na_2SO_4$ and evaporated to leave 3-(4-hydroxymethyl-phenyl)-propan-1-ol (0.51 g) as a colourless oil; $t_R$=0.61 min.

c) A solution of 3-(4-hydroxymethyl-phenyl)-propan-1-ol (500 mg, 3 mmol) in ethanol (40 mL) is treated with $MnO_2$. The suspension is stirred at 80° C. for 5 h before it is filtered and evaporated to give 4-(3-hydroxy-propyl)-benzaldehyde (470 mg) as a brownish oil; LC-MS: $t_R$=0.71 min; $^1$H NMR ($CDCl_3$): δ 9.97 (s, 1H), 7.81 (d, J=7.6 Hz, 2H), 7.36 (d, J=7.6 Hz, 2H), 3.69 (t, J=6.1 Hz, 2H), 2.80 (t, J=7.6 Hz, 2H), 1.97-1.85 (m, 2H).

d) A solution of 4-(3-hydroxy-propyl)-benzaldehyde (713 mg, 4.0 mmol), (1aS,5aR)-1-(1,1,2-trimethyl-1,1a,5,5a-tetrahydro-3-thia-cyclopropa[a]pentalen-4-yl)-ethanone (440 mg, 2.0 mmol), KOH (2.8 g, 50 mmol) in methanol (35 mL) is stirred at 70° C. for 1 h. The reaction mixture is diluted with water and acidified by adding 2 N aq. HCl. The mixture is extracted twice with DCM, the organic extracts are combined, dried over $Na_2SO_4$ and evaporated. The crude product is purified by prep. HPLC (Waters Xterra MS18 30×75 mm, 10 to 95% acetonitrile in water containing 0.5% formic acid) to give 3-[4-(3-hydroxy-propyl)-phenyl]-1-((1aS,5aR)-1,1,2-trimethyl-1,1a,5,5a-tetrahydro-3-thia-cyclopropa[a]pentalen-4-yl)-propenone (250 mg) as a pale yellow oil; LC-MS: $t_R$=1.10 min, $[M+1]^+$=367.21.

e) A mixture of 3-[4-(3-hydroxy-propyl)-phenyl]-1-((1aS,5aR)-1,1,2-trimethyl-1,1a,5,5a-tetrahydro-3-thia-cyclopropa[a]pentalen-4-yl)-propenone (183 mg, 0.50 mmol), Pd/C (200 mg, 10% Pd) in ethanol is stirred at rt under 1 atm $H_2$. The reaction mixture is filtered and the filtrate is evaporated to give 3-[4-(3-hydroxy-propyl)-phenyl]-1-((1aS,5aR)-1,1,2-trimethyl-1,1a,5,5a-tetrahydro-3-thia-cyclopropa[a]pentalen-4-yl)-propan-1-one (150 mg) as a pale yellow oil; LC-MS: $t_R$=1.09 min, $[M+1]^+$=369.10.

f) A solution of 3-[4-(3-hydroxy-propyl)-phenyl]-1-((1aS,5aR)-1,1,2-trimethyl-1,1a,5,5a-tetrahydro-3-thia-cyclopropa[a]pentalen-4-yl)-propan-1-one (147 mg, 0.40 mmol), DIPEA (0.11 mL, 0.642 mmol) in DCM (5 mL) is treated with methane sulfonylchloride (40 μL, 0.481 mmol) at 0° C. The solution is stirred at 0° C. for 30 min, then at rt for 1 h before it is diluted with DCM and washed with 0.1 N aq. NaOH solution, followed by 10% aq. citric acid solution. The organic layer is separated, dried over $Na_2SO_4$ and evaporated to give methanesulfonic acid 3-{4-[3-oxo-3-((1aS,5aR)-1,1,2-trimethyl-1,1a,5,5a-tetrahydro-3-thia-cyclopropa[a]pentalen-4-yl)-propyl]-phenyl}-propyl ester (176 mg) as a colourless oil; LC-MS: $t_R$=1.14 min, $[M+1]^+$=447.25.

g) A solution of 3-{4-[3-oxo-3-((1aS,5aR)-1,1,2-trimethyl-1,1a,5,5a-tetrahydro-3-thia-cyclopropa[a]pentalen-4-yl)-propyl]-phenyl}-propyl ester (5 mg, 11 μmol), DIPEA (12 μL, 11 μmol) and the appropriate amine (56 μmol) in DMF (0.5 mL) is shaken at 75° C. for 7 h. In the case of Examples 10 and 11 water (0.25 mL) and DMSO (0.5 mL) is added to the reaction mixture. The reaction mixture is diluted with acetic acid (0.2 mL) and then purified by prep. HPLC (Waters Symmetry C18 19×50 mm 5 μm, 10 to 95% acetonitrile in water containing 0.5% formic acid) to give the desired products as colourless lyophilisates.

| Example | R | Scale (μmol) | LC-MS $t_R$ (min) | $[M + H]^+$ |
|---|---|---|---|---|
| 2 | $NH_2$ | 11 | 0.89 | 368.30 |
| 3 | $NH-CH_3$ | 11 | 0.90 | 382.29 |
| 4 | $NH-CH_2CH_3$ | 11 | 0.92 | 396.38 |
| 5 | $N(CH_3)_2$ | 11 | 0.91 | 396.36 |
| 6 | HN~~~OH | 11 | 0.89 | 412.40 |
| 7 | HN~~~CH(OH)CH$_2$OH | 11 | 0.87 | 442.43 |
| 8 | HN~~~NH$_2$ | 11 | 0.79 | 411.33 |
| 9 | HN~~~O-Et | 11 | 0.96 | 454.43 |
| 10 | (S)-pyrrolidine-2-COOH | 11 | 0.95 | 466.40 |
| 11 | pyrrolidine-3-COOH | 11 | 0.91 | 466.38 |

Example 12

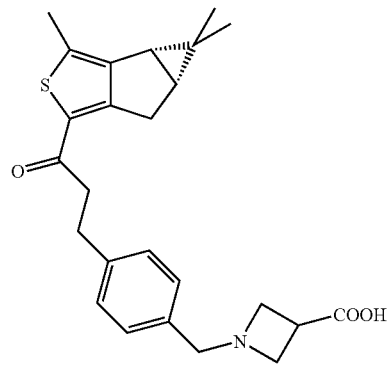

a) A solution of (1aS,5aR)-1-(1,1,2-trimethyl-1,1a,5,5a-tetrahydro-3-thia-cyclopropa[a]pentalen-4-yl)-ethanone (600 mg, 2.72 mmol) and terephthalaldehyde (913 mg, 6.81 mmol) in ethanol (10 mL) and approx. 6 N HCl in isopropanol (6 mL) is stirred at rt for 16 h. Further 6 N HCl in isopropanol (5 mL) is added and stirring of the dark solution is continued at rt for 24 h. The reaction mixture is diluted with diethyl ether (150 mL) and washed with sat. aq. $NaHCO_3$ solution followed by water. The organic phase is dried over $MgSO_4$ and evaporated. The crude product is purified by CC on silica gel eluting with heptane:EA 4:1 to give 4-[3-oxo-3-((1aS,5aR)-1,1,2-trimethyl-1,1a,5,5a-tetrahydro-3-thia-cyclopropa[a]pentalen-4-yl)-propenyl]-benzaldehyde (336 mg) as a yellow powder; LC-MS: $t_R$=1.14 min, $[M+1]^+$=337.29; $^1$H NMR (CDCl$_3$): δ 10.04 (s, 1H), 7.94-7.89 (m, 2H), 7.80-7.71 (m, 3H), 7.30 (d, J=15.8 Hz, 1H), 3.14 (dd, J=5.9, 18.8 Hz, 1H), 2.95 (d, J=18.8 Hz, 1H), 2.44 (s, 3H), 2.00-1.91 (m, 2H), 1.15 (s, 3H), 0.75 (s, 3H).

b) A suspension of 4-[3-oxo-3-((1aS,5aR)-1,1,2-trimethyl-1,1a,5,5a-tetrahydro-3-thia-cyclopropa[a]pentalen-4-yl)-propenyl]-benzaldehyde (50 mg, 0.15 mmol), azetidine-3-carboxylic acid (19 mg, 0.19 mmol) and NaHB(OAc)$_3$ (94 mg, 0.45 mmol) in acetonitrile (3 mL) is stirred at rt for 4 h before methanol (1 mL) is added. The clear solution is stirred for 5 min, diluted with water and extracted four times with DCM. The combined organic extracts are dried over MgSO$_4$ and evaporated. The obtained resin is dissolved in ethanol (5 mL) and THF (5 mL) and treated with a suspension of Pd/C (20 mg, 10% Pd) in ethanol (2 mL). The mixture is stirred at rt for 22 h under 1.5 bar H$_2$. The reaction mixture is filtered and the filtrate is evaporated. The crude product is purified by chromatography on prep. TLC-plates (DCM containing 20% of methanol) to give 1-{4-[3-oxo-3-((1aS,5aR)-1,1,2-trimethyl-1,1a,5,5a-tetrahydro-3-thia-cyclopropa[a]pentalen-4-yl)-propyl]-benzyl}-azetidine-3-carboxylic acid (24 mg) as a beige foam; LC-MS: $t_R$=0.87 min, [M+1]$^+$=424.24; $^1$H NMR (CDCl$_3$): δ 7.30-7.16 (m, 4H), 4.02-3.70 (m br, 7H), 3.28-3.18 (m, 1H), 3.04-2.90 (m, 3H), 2.76 (d, J=18.8 Hz, 1H), 2.36 (s, 3H), 1.90-1.84 (m, 2H), 1.10 8s, 3H), 0.68 (s, 3H).

Examples 13 to 23

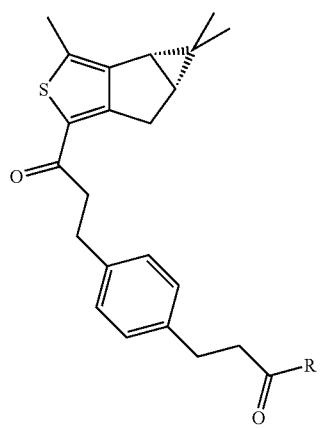

a) A solution of 3-(4-hydroxymethyl-phenyl)-propionic acid (720 mg, 4.0 mmol, Example 2a) in ethanol (20 mL) is treated with MnO$_2$ (350 mg, 4.0 mmol) and the resulting suspension is stirred at 80° C. for 18 h. Another portion of MnO$_2$ (500 mg, 5.7 mmol) is added and stirring is continued at 80° C. for 2 days. The mixture is filtered and the filtrate is evaporated to give 3-(4-formyl-phenyl)-propionic acid (500 mg) as a brown solid; LC-MS: $t_R$=0.72 min.

b) A solution of 3-(4-formyl-phenyl)-propionic acid (142 mg, 0.80 mmol), (1aS,5aR)-1-(1,1,2-trimethyl-1,1a,5,5a-tetrahydro-3-thia-cyclopropa[a]pentalen-4-yl)-ethanone (176 mg, 0.80 mmol), KOH (2.8 g, 50 mmol) in methanol (25 mL) is stirred at 70° C. for 1 h. The reaction mixture is diluted with water (400 mL) and acidified by adding 2 N aq. HCl. The mixture is extracted twice with DCM, the organic extracts are combined, dried over Na$_2$SO$_4$ and evaporated. The crude product is purified by prep. HPLC (Waters Xterra MS18 30×75 mm, 10 to 95% acetonitrile in water containing 0.5% formic acid) to give 3-{4-[3-oxo-3-((1aS,5aR)-1,1,2-trimethyl-ethyl-1,1a,5,5a-tetrahydro-3-thia-cyclopropa[a]pentalen-4-yl)-propenyl]-phenyl}-propionic acid (125 mg) as yellow resin; LC-MS: $t_R$=1.07 min, [M+1]$^+$=381.18.

c) A mixture of 3-{4-[3-oxo-3-((1aS,5aR)-1,1,2-trimethyl-1,1a,5,5a-tetrahydro-3-thia-cyclopropa[a]pentalen-4-yl)-propenyl]-phenyl}-propionic acid (121 mg, 0.32 mmol), Pd/C (40 mg, 10% Pd) in ethanol (8 mL) is stirred at rt under 1 bar H$_2$. The reaction mixture is filtered, the filtrate is evaporated to give 3-{4-[3-oxo-3-((1aS,5aR)-1,1,2-trimethyl-1,1a,5,5a-tetrahydro-3-thia-cyclopropa[a]pentalen-4-yl)-propyl]-phenyl}-propionic acid (120 mg) as a pale yellow oil; LC-MS: $t_R$=1.07 min, [M+1]$^+$=383.17.

d) A solution of 3-{4-[3-oxo-3-((1aS,5aR)-1,1,2-trimethyl-1,1a,5,5a-tetrahydro-3-thia-cyclopropa[a]pentalen-4-yl)-propyl]-phenyl}-propionic acid (5 mg, 12 μmol), TBTU (4 mg, 12 μmol) and DIPEA (8 μL, 60 μmol) in DMF (0.5 mL) is treated with the appropriate amine (30 μmol). The reaction mixture is stirred at rt for 7 h before it is diluted with acetic acid (0.2 mL) and then purified by prep. HPLC (Waters Xterra MS18, 50×20 mm ID, 5 μm, 10 to 95% acetonitrile in water containing 0.5% formic acid) to give the desired products as colourless lyophilisates.

| | | | LC-MS | |
|---|---|---|---|---|
| Example | R | Scale (μmol) | $t_R$ (min) | [M + H]$^+$ |
| 13 | NH$_2$ | 12 | 1.05 | 382.32 |
| 14 | NH—CH$_3$ | 12 | 1.08 | 396.31 |
| 15 | NH—CH$_2$CH$_3$ | 12 | 1.10 | 410.32 |
| 16 | N(CH$_3$)$_2$ | 12 | 1.12 | 410.25 |
| 17 | HN～OH | 12 | 1.00 | 426.30 |
| 18 | HN(CH$_2$OH)$_2$ | 12 | 0.94 | 458.38 |
| 19 | HN～O～ | 12 | 1.11 | 468.35 |
| 20 | HN—CH$_2$COOH | 12 | 1.00 | 440.37 |
| 21 | azetidine-COOH | 12 | 1.01 | 466.32 |
| 22 | (S)-pyrrolidine-COOH | 12 | 1.04 | 480.37 |
| 23 | pyrrolidine-COOH | 12 | 1.03 | 480.37 |

Examples 24 to 33

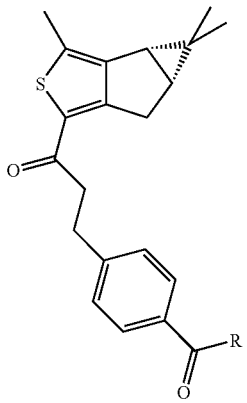

a) A solution of 4-formyl-benzoic acid (1.04 g mg, 6.93 mmol), (1aS,5aR)-1-(1,1,2-trimethyl-1,1a,5,5a-tetrahydro-3-thia-cyclopropa[a]pentalen-4-yl)-ethanone (850 mg, 3.86 mmol), NaOMe (4.17 g, 77.2 mmol) in methanol (30 mL) is stirred at 65° C. for 2 h. Another portion of 4-formyl-benzoic acid (400 mg, 2.66 mmol) is added and stirring is continued at 65° C. for 2 h. The reaction mixture is diluted with diethyl ether (200 mL) and washed with 5% aq. citric acid solution followed by water. The organic phase is dried over $MgSO_4$ and evaporated. The crude product is purified by CC on silica gel eluting with DCM containing 2-7% methanol, followed by crystallisation from methanol:water 1:1 to give 4-[3-oxo-3-((1aS,5aR)-1,1,2-trimethyl-1,1a,5,5a-tetrahydro-3-thia-cyclopropa[a]pentalen-4-yl)-propenyl]-benzoic acid (780 mg) as beige yellow powder; LC-MS: $t_R$=1.06 min, $[M+1]^+$=353.03; $^1$H NMR ($CDCl_3$): δ 8.13 (d, J=8.2 Hz, 2H), 7.76 (d, J=15.2 Hz, 1H), 7.68 (d, J=8.2 Hz, 2H), 7.29 8d, J=15.8 Hz, 1H), 3.14 (dd, J=5.9, 18.8 Hz, 1H), 2.96 (d, J=18.8 Hz, 1H), 2.44 (s, 3H), 2.00-1.91 (m, 2H), 1.15 (s, 3H), 0.75 (s, 3H).

b) A mixture of 4-[3-oxo-3-((1aS,5aR)-1,1,2-trimethyl-1,1a,5,5a-tetrahydro-3-thia-cyclopropa[a]pentalen-4-yl)-propenyl]-benzoic acid (780 mg, 2.21 mmol), Pd/C (250 mg, 10% Pd) in ethanol (50 mL) and THF (10 mL) is stirred at rt for 2 h under 1.5 bar $H_2$. The reaction mixture is filtered, the filtrate is evaporated and the crude product is purified by CC on silica gel eluting with EA to give 4-[3-oxo-3-((1aS,5aR)-1,1,2-trimethyl-1,1a,5,5a-tetrahydro-3-thia-cyclopropa[a]pentalen-4-yl)-propyl]-benzoic acid (751 mg) as a colourless foam; LC-MS: $t_R$=1.04 min, $[M+1]^+$=355.08; $^1$H NMR ($CDCl_3$): δ 8.02 (d, J=7.6 Hz, 2H), 7.32 8d, J=7.6 Hz, 2H), 3.12-2.90 (m, 5H), 2.77 (d, J=18.8 Hz, 1H), 2.37 (s, 3H), 1.92-1.86 (m, 2H), 1.11 (s, 3H), 0.69 (s, 3H).

c) A solution of 4-[3-oxo-3-((1aS,5aR)-1,1,2-trimethyl-1,1a,5,5a-tetrahydro-3-thia-cyclopropa[a]pentalen-4-yl)-propyl]-benzoic acid (5 mg, 15 µmol), TBTU (5 mg, 15 µmol) and DIPEA (6 µL, 45 µmol) is treated with the appropriate amine (30 µmol). The reaction mixture is stirred at rt for 7 h before it is diluted with acetic acid (0.2 mL) and then purified by prep. HPLC (Waters Xterra MS18, 50×20 mm ID, 5 µm, to 95% acetonitrile in water containing 0.5% formic acid) to give the desired products as colourless lyophilisates.

|         |                                  |                | LC-MS       |             |
|---------|----------------------------------|----------------|-------------|-------------|
| Example | R                                | Scale (µmol)   | $t_R$ (min) | $[M + H]^+$ |
| 24      | $NH_2$                           | 15             | 1.03        | 354.22      |
| 25      | NH—$CH_3$                        | 15             | 1.06        | 368.15      |
| 26      | NH—$CH_2CH_3$                    | 15             | 1.07        | 382.14      |
| 27      | NH—$CH_2CH_2CH_3$                | 15             | 1.10        | 396.12      |
| 28      | NH—$CH(CH_3)_2$                  | 15             | 1.09        | 396.18      |
| 29      | HN—CH$_2$CH$_2$—OH               | 15             | 0.97        | 398.13      |
| 30      | HN—CH(CH$_2$OH)$_2$              | 15             | 0.92        | 428.23      |
| 31      | HN—CH$_2$CH$_2$—NH$_2$           | 15             | 0.83        | 397.14      |
| 32      | HN—CH$_2$CH$_2$CH$_2$—O—CH$_2$CH$_3$ | 15         | 1.09        | 440.25      |
| 33      | HN—CH$_2$—C(O)OH                 | 15             | 0.97        | 412.16      |

Examples 34 to 36

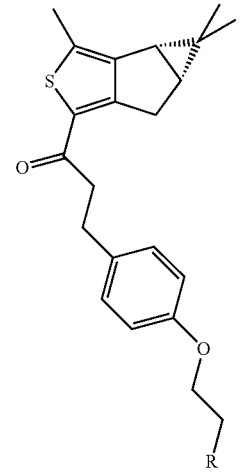

A solution of 3-(4-hydroxy-phenyl)-1-((1aS,5aR)-1,1,2-trimethyl-1,1a,5,5a-tetrahydro-3-thia-cyclopropa[a]pentalen-4-yl)-propan-1-one (6.5 mg, 20 µmol, Intermediate 2) in isopropanol (0.8 mL) and 2 N aq. NaOH (0.25 mL) is treated with the appropriate alkylating agent (4 eq. as chloride, bromide or methane sulfonate). The reaction mixture is shaken at 70° C. for 5 h before it is purified by prep. HPLC (Waters Xterra MS18 19×50 mm 5µm, 10 to 95% acetonitrile in water containing 0.5% formic acid) to give the desired product as colourless lyophilisate in the form of a formic acid salt.

| Example | R | Scale (μmol) | LC-MS t$_R$ (min) | [M + H]$^+$ |
|---|---|---|---|---|
| 34 | N(CH$_3$)$_2$ | 20 | 0.90 | 398.22 |
| 35 |  | 20 | 0.92 | 424.22 |
| 36 |  | 20 | 0.90 | 440.29 |

Examples 37 to 39

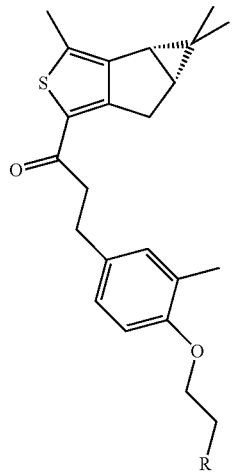

A solution of 3-(4-hydroxy-3-methyl-phenyl)-1-((1aS,5aR)-1,1,2-trimethyl-1,1a,5,5a-tetrahydro-3-thia-cyclopropa[a]pentalen-4-yl)-propan-1-one (6.8 mg, 20 μmol, Intermediate 4) in isopropanol (0.8 mL) and 2 N aq. NaOH (0.25 mL) is treated with the appropriate alkylating agent (4 eq. as chloride, bromide or methane sulfonate). The reaction mixture is shaken at 70° C. for 5 h before it is purified by prep. HPLC (Waters Xterra MS18 19×50 mm 5 μm, 10 to 95% acetonitrile in water containing 0.5% formic acid) to give the desired product as colourless lyophilisate in the form of a formic acid salt.

| Example | R | Scale (μmol) | LC-MS t$_R$ (min) | [M + H]$^+$ |
|---|---|---|---|---|
| 37 | N(CH$_3$)$_2$ | 20 | 0.92 | 412.18 |
| 38 |  | 20 | 0.94 | 438.25 |

| Example | R | Scale (μmol) | LC-MS t$_R$ (min) | [M + H]$^+$ |
|---|---|---|---|---|
| 39 |  | 20 | 0.92 | 454.33 |

Examples 40 to 48

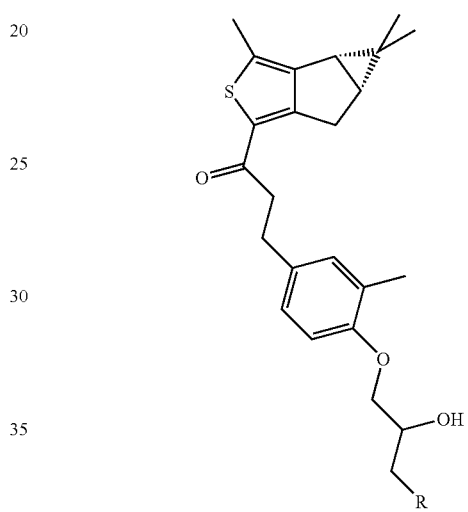

a) A solution of 3-(4-hydroxy-3-methyl-phenyl)-1-((1aS,5aR)-1,1,2-trimethyl-1,1a,5,5a-tetrahydro-3-thia-cyclopropa[a]pentalen-4-yl)-propan-1-one (179 mg, 0.525 mmol, Intermediate 4) in isopropanol (10 mL) and 3 N aq. NaOH (4 mL) is treated with epichlorohydrine (197 mg, 1.58 mmol). The reaction mixture is stirred at 70 for 1.5 h. The mixture is diluted with acetic acid (0.3 mL) and the solvent is removed under reduced pressure. The residue is purified by prep. HPLC (Waters Xterra MS18, 75×30 mm ID, 10 μm, 10 to 95% acetonitrile in water containing 0.5% formic acid) to give 3-(3-methyl-4-oxiranylmethoxy-phenyl)-1-((1aS,5aR) 1,1,2-trimethyl-1,1a,5,5a-tetrahydro-3-thia-cyclopropa[a]pentalen-4-yl)-propan-1-one (68 mg) as a pale brown oil; LC-MS: t$_R$=1.15 min, [M+1]$^+$=397.27.

b) A solution of 3-(3-methyl-4-oxiranylmethoxy-phenyl)-1-((1aS,5aR)1,1,2-trimethyl-1,1a,5,5a-tetrahydro-3-thia-cyclopropa[a]pentalen-4-yl)-propan-1-one (6 mg, 15 μmol) in ethanol (1 mL) is treated with the appropriate amine (≧4 eq.). If the amine in addition contains a carboxylic acid functionality, water (500 μL) and DIPEA (20 μL) is added to the reaction mixture. The reaction mixture is stirred at 85° C. for 5 h before it is purified by prep. HPLC (Waters Xterra MS18 19×50 mm 5 μm, 10 to 95% acetonitrile in water containing 0.5% formic acid) to give the desired products as colourless to pale yellow resins.

Examples 49 to 51

| Example | R | Scale (μmol) | LC-MS $t_R$ (min) | [M + H]$^+$ |
|---|---|---|---|---|
| 40 | NH$_2$ | 15 | 0.88 | 414.31 |
| 41 | NHCH$_3$ | 15 | 0.90 | 428.33 |
| 42 | NHCH$_2$CH$_3$ | 15 | 0.92 | 442.47 |
| 43 | NHCH(CH$_3$)$_2$ | 15 | 0.93 | 456.39 |
| 44 | HN–CH$_2$CH$_2$–OH | 15 | 0.89 | 458.25 |
| 45 | HN–CH$_2$CH(OH)CH$_2$OH | 15 | 0.88 | 488.43 |
| 46 | HN–CH$_2$CH$_2$–O–Et | 15 | 0.96 | 500.45 |
| 47 | HN–CH$_2$CH$_2$–NH$_2$ | 15 | 0.81 | 457.41 |
| 48 | HN–CH$_2$CH$_2$–C(O)OH | 15 | 0.90 | 486.41 |

| Example | R | Scale (μmol) | LC-MS $t_R$ (min) | [M + H]$^+$ |
|---|---|---|---|---|
| 49 | N(CH$_3$)$_2$ | 20 | 0.92 | 432.20 |
| 50 | pyrrolidinyl | 20 | 0.94 | 458.15 |
| 51 | morpholinyl | 20 | 0.92 | 474.15 |

Examples 49 to 51

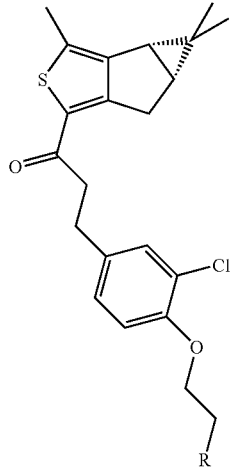

A solution of 3-(3-chloro-4-hydroxy-phenyl)-1-((1aS,5aR)-1,1,2-trimethyl-1,1a,5,5a-tetrahydro-3-thia-cyclopropa[a]pentalen-4-yl)-propan-1-one (7.2 mg, 20 μmol, Intermediate 6) in isopropanol (0.8 mL) and 2 N aq. NaOH (0.25 mL) is treated with the appropriate alkylating agent (4 eq. as chloride, bromide or methane sulfonate). The reaction mixture is shaken at 70° C. for 5 h before it is purified by prep. HPLC (Waters Xterra MS18 19×50 mm 5 μm, 10 to 95% acetonitrile in water 0.5% formic acid) to give the desired product as colourless lyophilisate in the form of a formic acid salt.

Examples 52 to 60

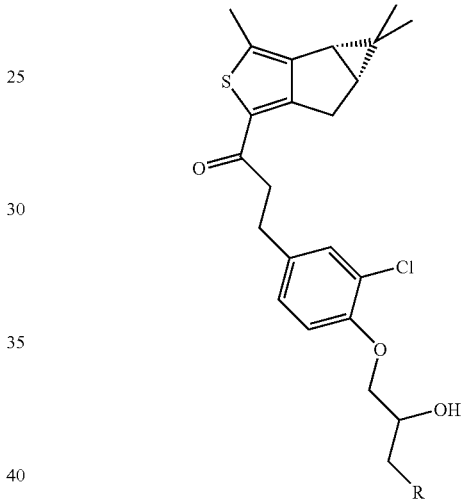

a) A solution of 3-(3-chloro-4-hydroxy-phenyl)-1-((1aS,5aR)-1,1,2-trimethyl-1,1a,5,5a-tetrahydro-3-thia-cyclopropa[a]pentalen-4-yl)-propan-1-one (139 mg, 0.385 mmol, Intermediate 6) in isopropanol (4 mL) and 3 N aq. NaOH (1.7 mL) is treated with epichlorohydrine (110 mg, 1.16 mmol). The reaction mixture is stirred at rt for 18 h. The mixture is diluted with acetic acid (0.3 mL) and the solvent is removed under reduced pressure. The residue is purified by prep. HPLC (Waters Xterra MS18, 75×30 mm ID, 10 μm, 10 to 95% acetonitrile in water containing 0.5% formic acid) to give 3-(3-chloro-4-oxiranylmethoxy-phenyl)-1-((1aS,5aR)1,1,2-trimethyl-1,1a,5,5a-tetrahydro-3-thia-cyclopropa[a]pentalen-4-yl)-propan-1-one (39 mg) as a pale yellow oil; LC-MS: $t_R$=1.15 min, [M+1]$^+$=417.21.

b) A solution of 3-(3-chloro-4-oxiranylmethoxy-phenyl)-1-((1aS,5aR)1,1,2-trimethyl-1,1a,5,5a-tetrahydro-3-thia-cyclopropa[a]pentalen-4-yl)-propan-1-one (6 mg, 15 μmol) in ethanol (1 mL) is treated with the appropriate amine (≧4 eq.). If the amine in addition contains a carboxylic acid functionality, water (500 μL) and DIPEA (20 μL) is added to the reaction mixture. The reaction mixture is stirred at 85° C. for 5 h before it is purified by prep. HPLC (Waters Xterra MS18 19×50 mm 5 μm, 10 to 95% acetonitrile in water containing 0.5% formic acid) to give the desired products as colourless to pale yellow resins.

|  |  |  | LC-MS | |
|---|---|---|---|---|
| Example | R | Scale (μmol) | $t_R$ (min) | $[M + H]^+$ |
| 52 | NH$_2$ | 15 | 0.89 | 434.23 |
| 53 | NHCH$_3$ | 15 | 0.90 | 448.29 |
| 54 | NHCH$_2$CH$_3$ | 15 | 0.92 | 462.39 |
| 55 | NHCH(CH$_3$)$_2$ | 15 | 0.93 | 476.43 |
| 56 | HN⌒OH | 15 | 0.89 | 478.35 |
| 57 | HN-CH(CH$_2$OH)$_2$ | 15 | 0.88 | 508.46 |
| 58 | HN⌒O⌒ | 15 | 0.96 | 520.44 |
| 59 | HN⌒NH$_2$ | 15 | 0.81 | 477.39 |
| 60 | HN-CH$_2$CH$_2$COOH | 15 | 0.90 | 506.30 |

Examples 61 to 63

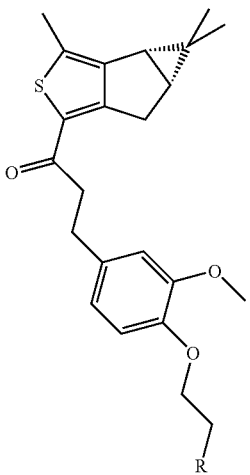

A solution of 3-(4-hydroxy-3-methoxy-phenyl)-1-((1aS, 5aR)-1,1,2-trimethyl-1,1a,5,5a-tetrahydro-3-thia-cyclopropa[a]pentalen-4-yl)-propan-1-one (7.1 mg, 20 μmol, Intermediate 8) in isopropanol (0.8 mL) and 2 N aq. NaOH (0.25 mL) is treated with the appropriate alkylating agent (4 eq. as chloride, bromide or methane sulfonate). The reaction mixture is shaken at 70° C. for 5 h before it is purified by prep. HPLC (Waters Xterra MS18 19×50 mm 5 μm, 10 to 95% acetonitrile in water containing 0.5% formic acid) to give the desired product as colourless lyophilisate in the form of a formic acid salt.

|  |  |  | LC-MS | |
|---|---|---|---|---|
| Example | R | Scale (μmol) | $t_R$ (min) | $[M + H]^+$ |
| 61 | N(CH$_3$)$_2$ | 20 | 0.90 | 428.28 |
| 62 | pyrrolidinyl | 20 | 0.92 | 454.38 |
| 63 | morpholinyl | 20 | 0.90 | 470.25 |

Examples 64 to 80

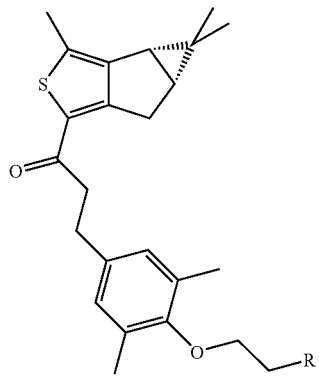

a) A solution of 3-(3,5-dimethyl-4-hydroxy-phenyl)-1-((1aS,5aR)-1,1,2-trimethyl-1,1a,5,5a-tetrahydro-3-thia-cyclopropa[a]pentalen-4-yl)-propan-1-one (3.00 g, 8.46 mmol, Intermediate 10) in isopropanol (80 mL) and 2 N aq. NaOH (30 mL) is treated with 2-bromoethanol (2.11 g, 16.9 mmol). The dark red reaction mixture is stirred at 70° C. for 5.5 h. The solvent is removed under reduced pressure and the residue is dissolved in EA and washed twice with water. The organic layer is dried over MgSO$_4$ and evaporated. The crude product is purified by CC on silica gel eluting with heptane:EA 1:1 to give 3-[4-(2-hydroxy-ethoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one (1.57 g) as an orange oil; LC-MS: $t_R$=1.09 min, $[M+1]^+$=399.35.

b) To a solution of 3-[4-(2-hydroxy-ethoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one (1.55 g, 3.89 mmol) in DCM (60 mL) and DIPEA (1.07 mL, 6.22 mmol) is added methane sulfonylchloride (0.362 mL, 4.67 mmol) at 0° C. The reaction mixture is stirred at 0° C. for 30 min. Another portion of methane sulfonylchloride (0.362 mL, 4.67 mmol) is added and stirring is continued for 30 min. The reaction mixture is diluted with DCM, washed with 0.1 N aq. NaOH followed by 10% aq. citric acid solution, dried over MgSO$_4$ and evaporated to give methanesulfonic acid 2-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-ethyl ester (1.57 g) as an orange resin; LC-MS: $t_R$=1.14 min, $[M+1]^+$=477.35; $^1$H NMR (CDCl$_3$): δ 6.86 (s, 2H), 4.57-4.50 (m, 2H), 4.05-4.00 (m, 2H), 3.10 8s, 3H), 3.03-2.85 (m, 5H), 2.79 (d, J=18.8 Hz, 1H), 2.37 8s, 3H), 2.25 (s, 6H), 1.92-1.85 (m, 2H), 1.11 (s, 3H), 0.70 (s, 3H).

c) A solution of methanesulfonic acid 2-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-ethyl ester in DMF, ethanol, or isopropanol is treated with the appropriate amine (≧4 eq.). If the amine in addition contains a carboxylic acid functionality, water and DIPEA is added to the reaction mixture. The reaction mixture is stirred at 65 to 75° C. for 4 to 48 h before it is purified by prep. HPLC (Waters Xterra MS18 19×50 mm 5µm, 10 to 95% acetonitrile in water containing 0.5% sat. aq. ammonia, or Zorbax SB-AQ, 10 to 95% acetonitrile in water containing 0.5% formic acid). Compounds purified under acidic HPLC-conditions are extracted with EA from the respective HPLC fractions, evaporated and dried under high vacuum.

| Example | R | Scale (µmol) | Aspect | LC-MS $t_R$ (min) | $[M + H]^+$ |
|---|---|---|---|---|---|
| 64 | $NH_2$ | 525 | yellow oil | 0.89 | 398.14 |
| 65 | $NHCH_3$ | 525 | pale yellow oil | 0.91 | 412.29 |
| 66 | $NHCH_2CH_3$ | 14 | colourless lyophilisate | 0.93 | 426.19 |
| 67 | $NHCH_2CH_2CH_3$ | 14 | colourless lyophilisate | 0.95 | 440.22 |
| 68 | $NHCH(CH_3)_2$ | 14 | colourless lyophilisate | 0.95 | 440.22 |
| 69 | $N(CH_3)_2$ | 14 | colourless lyophilisate | 0.93 | 426.18 |
| 70 | HN–CH₂CH₂–OH | 525 | colourless foam | 0.90 | 442.19 |
| 71 | HN–CH(CH₂OH)₂ | 525 | beige foam | 0.89 | 472.23 |
| 72 | HN–CH₂CH₂–O–CH₂CH₃ | 14 | colourless lyophilisate | 0.97 | 484.27 |
| 73 | (CH₃)N(CH₂CH₂OH)– | 50 | colourless lyophilisate | 0.91 | 456.34 |
| 74 | (CH₃CH₂)N(CH₂CH₂OH)– | 50 | colourless lyophilisate | 0.93 | 470.40 |
| 75 | pyrrolidinyl | 225 | beige oil | 0.95 | 452.23 |
| 76 | morpholinyl | 50 | colourless lyophilisate | 0.93 | 468.37 |
| 77 | piperazinyl | 50 | colourless lyophilisate | 0.83 | 467.34 |

-continued

| Example | R | Scale (μmol) | Aspect | LC-MS $t_R$ (min) | $[M + H]^+$ |
|---|---|---|---|---|---|
| 78 | piperazine-CH2CH2-OH | 14 | colourless lyophilisate | 0.86 | 511.30 |
| 79 | azetidine-COOH | 14 | colourless lyophilisate | 0.92 | 482.20 |
| 80 | (S)-pyrrolidine-COOH | 14 | colourless lyophilisate | 0.96 | 496.25 |

Example 64

$^1$H NMR (CDCl$_3$): δ 6.85 (s, 2H), 3.80-3.75 (m, 2H), 3.07 (s br, 1H), 3.03-2.84 (m, 7H), 2.79 (d, J=18.8 Hz, 1H), 2.37 (s, 3H), 2.25 8s, 6H), 1.92-1.85 (m, 2H), 1.11 (s, 3H), 0.70 (s, 3H).

Example 65

As Formate Salt $^1$H NMR (CDCl$_3$): δ 8.46 (s 1H), 6.85 (s, 2H), 4.25 (s br, 3H), 4.04-3.97 (m, 2H), 3.24-3.16 (m, 2H), 3.03-2.84 (m, 5H), 2.78 (d, J=18.8 Hz, 1H), 2.73 (s, 3H), 2.37 8s, 3H), 2.25 (s, 6H), 1.92-1.85 (m, 2H), 1.11 (s, 3H), 0.70 (s, 3H).

Example 70

As Formate Salt $^1$H NMR (CDCl$_3$): δ 8.49 (s, 1H), 6.84 (s, 2H), 5.58 (s br, 3H), 4.05-3.98 (m, 2H), 3.94-3.86 (m, 2H), 3.34-3.25 (m, 2H), 3.22-3.15 (m, 2H), 3.03-2.84 (m, 5H), 2.78 (d, J=18.8 Hz, 1H), 2.37 (s, 3H), 2.24 (s, 6H), 1.92-1.86 (m, 2H), 1.11 (s, 3H), 0.70 (s, 3H).

Example 71

$^1$H NMR (CDCl$_3$): δ 6.84 (s, 2H), 4.87 (s br, 3H), 4.00-3.95 (m, 2H), 3.92-3.75 (m, 4H), 3.33-3.27 (m, 2H), 3.18-3.10 (m, 1H), 3.03-2.84 (m, 5H), 2.78 (J=18.8 Hz, 1H), 2.37 (s, 3H), 2.24 (s, 6H), 1.92-1.85 (m, 2H), 1.11 (s, 3H), 0.70 (s, 3H).

Example 75

$^1$H NMR (CDCl$_3$): δ 6.84 (s, 2H), 3.87 (t, J=6.4 Hz, 2H), 3.04-2.85 (m, 7H), 2.79 (d, J=18.8 Hz, 1H), 2.66-2.59 (m, 4H), 2.37 (s, 3H), 2.25 (s, 6H), 1.91-1.86 (m, 2H), 1.84-1.79 (m, 4H), 1.10 (s, 3H), 0.70 (s, 3H).

Examples 81 to 98

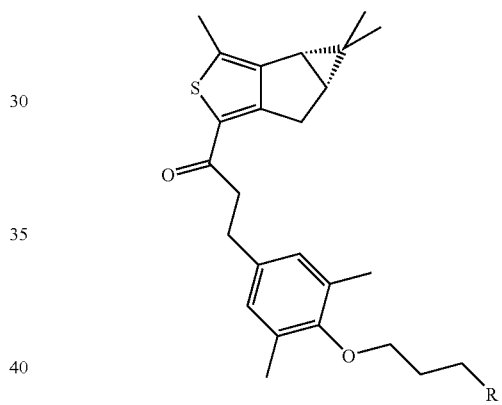

a) A solution of 3-(3,5-dimethyl-4-hydroxy-phenyl)-1-((1aS,5aR)-1,1,2-trimethyl-1,1a,5,5a-tetrahydro-3-thia-cyclopropa[a]pentalen-4-yl)-propan-1-one (3.00 g, 8.46 mmol, Intermediate 10) in isopropanol (80 mL) and 2 N aq. NaOH (30 mL) is treated with 3-bromopropanol (2.35 g, 16.9 mmol). The dark red reaction mixture is stirred at 70° C. for 5 h. The solvent is removed under reduced pressure and the residue is dissolved in EA and washed twice with water. The organic layer is dried over MgSO$_4$ and evaporated. The crude product is purified by CC on silica gel eluting with heptane: EA 1:1 to give 3-[4-(3-hydroxy-propoxy)-3,5-dimethyl-phenyl]-1-((1aS,5aR)-1,1,2-tri methyl-1,1a,5,5a-tetrahydro-3-thia-cyclopropa[a]pentalen-4-yl)-propan-1-one (2.55 g) as a yellow oil; LC-MS: $t_R$=1.10 min, $[M+1]^+$=413.33; $^1$H NMR (CDCl$_3$): δ 6.87 (s, 2H), 3.99-3.90 (m, 4H), 3.04-2.85 (m, 5H), 2.81 (d, J=18.8 Hz, 1H), 2.39 (s, 3H), 2.27 (s, 6H), 2.10-2.01 (m, 2H), 1.93-1.88 (m, 2H), 1.13 (s, 3H), 0.72 (s, 3H).

b) To a solution of 3-[4-(3-hydroxy-propoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one (2.00 g, 4.85 mmol) in DCM (60 mL) and DIPEA (1.33 mL, 7.76 mmol) is added methane sulfonylchloride (0.452 mL, 582 μmol) at 0° C. The reaction mixture is stirred at 0° C. for 30 min. Another portion of methane sulfonylchloride (0.452 mL, 5.82 mmol) is added and stirring is continued for 30 min. The reaction mixture is diluted with DCM, washed with 0.1 N aq. NaOH followed by 10% aq. citric acid solution, dried over $MgSO_4$ and evaporated to give methanesulfonic acid 3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-propyl ester (2.38 g) as a brown oil; LC-MS: $t_R$=1.15 min, $[M+1]^+$=491.34.

c) A solution of methanesulfonic acid 3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-propyl ester in DMF, methanol, ethanol, or isopropanol is treated with the appropriate amine ($\geqq$4 eq.). If the amine in addition contains a carboxylic acid functionality, water and DIPEA is added to the reaction mixture. The reaction mixture is stirred at 65 to 75° C. for 4 to 48 h before it is purified by prep. HPLC (Waters Xterra MS18 19×50 mm 5 μm, 10 to 95% acetonitrile in water containing 0.5% sat. aq. ammonia, or Zorbax SB-AQ, 10 to 95% acetonitrile in water containing 0.5% formic acid) or by CC on silica gel eluting with DCM containing 10-25% methanol. To avoid salt formation, some of the compounds purified under acidic HPLC-conditions are extracted with EA from the respective HPLC fractions, evaporated and dried under high vacuum.

| Example | R | Scale (μmol) | Aspect | LC-MS $t_R$ (min) | $[M + H]^+$ |
|---|---|---|---|---|---|
| 81 | $NH_2$ | 500 | yellow oil | 0.90 | 412.39 |
| 82 | $NHCH_3$ | 500 | pale yellow oil | 0.93 | 426.25 |
| 83 | $NHCH_2CH_3$ | 13 | colourless lyophilisate | 0.94 | 440.33 |
| 84 | $NHCH_2CH_2CH_3$ | 13 | colourless lyophilisate | 0.96 | 454.32 |
| 85 | $NHCH(CH_3)_2$ | 13 | colourless lyophilisate | 0.95 | 454.28 |
| 86 | $N(CH_3)_2$ | 13 | colourless lyophilisate | 0.93 | 440.29 |
| 87 | HN−CH₂CH₂−OH | 1223 | pale yellow oil | 0.90 | 456.31 |
| 88 | HN−CH(CH₂OH)−CH₂OH | 20 | colourless lyophilisate | 0.90 | 486.36 |
| 89 | HN−CH₂CH₂−O−CH₂CH₃ | 13 | colourless lyophilisate | 0.97 | 498.33 |
| 90 | (CH₃)N−CH₂CH₂−OH | 50 | colourless lyophilisate | 0.92 | 470.39 |
| 91 | (cyclopropyl)N−CH₂CH₂−OH | 50 | colourless lyophilisate | 0.93 | 484.40 |
| 92 | HN−CH₂CH₂−NH₂ | 13 | colourless lyophilisate | 0.81 | 455.29 |
| 93 | pyrrolidin-1-yl | 13 | colourless lyophilisate | 0.96 | 466.34 |

-continued

| Example | R | Scale (μmol) | Aspect | LC-MS $t_R$ (min) | $[M + H]^+$ |
|---|---|---|---|---|---|
| 94 | morpholine | 50 | colourless lyophilisate | 0.95 | 482.40 |
| 95 | piperazine | 50 | colourless lyophilisate | 0.83 | 481.40 |
| 96 | HN-CH2-COOH | 13 | colourless lyophilisate | 0.91 | 470.29 |
| 97 | azetidine-COOH | 20 | colourless lyophilisate | 0.93 | 496.30 |
| 98 | pyrrolidine-COOH | 13 | colourless lyophilisate | 0.93 | 510.19 |

Example 81

$^1$H NMR (CDCl$_3$): δ 7.01 (s br, 2H), 6.84 (s, 2H), 3.86 (t, J=5.2 Hz, 2H), 3.28 (t, J=6.7 Hz, 2H), 3.02-2.84 (m, 5H), 2.78 (d, J=18.8 Hz, 1H), 2.37 (s, 3H), 2.20 (s, 6H), 2.19-2.11 (m, 2H), 1.92-1.85 (m, 2H), 1.11 (s, 3H), 0.70 (s, 3H).

Example 82

$^1$H NMR (CDCl$_3$): δ 6.84 (s, 2H), 3.81 (t, J=5.9 Hz, 2H), 3.03-2.84 (m, 7H), 2.79 (d, J=18.8 Hz, 1H), 2.55 8s, 3H), 2.37 (s, 3H), 2.22 8s, 6H), 2.12-2.04 (m, 2H), 1.92-1.85 (m, 2H), 1.11 8s, 3H), 0.70 (s, 3H).

Example 87

$^1$H NMR (CDCl$_3$): δ 6.85 (s, 2H), 3.81 (t, J=6.4 Hz, 2H), 3.65 (t, J=5.3 Hz, 2H), 3.04-2.75 (m, 10 H), 2.37 (s, 3H), 2.24 (s, 6H), 1.98 (p, J=6.4 Hz, 2H), 1.92-1.87 (m, 2H), 1.82 (s br, 2H), 1.11 (s, 3H), 0.70 (s, 3H).

Example 92

As 2-Fold Formate Salt $^1$H NMR (CDCl$_3$): δ 8.37 (s, 2H), 7.60 (s br, 5H), 6.80 (s, 2H), 3.80-3.70 (m, 2H), 3.50-3.35 (m, 2H), 3.04-2.74 (m, 6H), 2.36 (s, 3H), 2.24-2.14 (m, 5H), 1.9-1.85 (m, 2H), 1.10 (s, 3H), 0.69 (s, 3H).

Examples 99 to 117

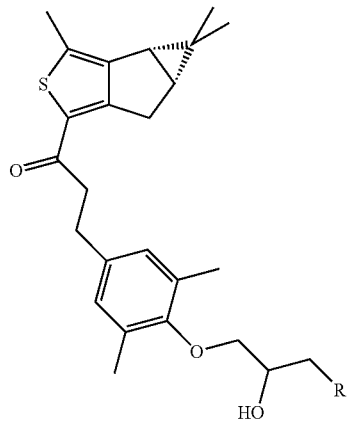

a) A solution of 3-(3,5-dimethyl-4-hydroxy-phenyl)-1-((1aS,5aR)-1,1,2-trimethyl-1,1a,5,5a-tetrahydro-3-thia-cyclopropa[a]pentalen-4-yl)-propan-1-one (2.00 g, 5.64 mmol, Intermediate 10) in isopropanol (20 mL) and 3 N aq. NaOH (12 mL) is treated with epichlorohydrine (2.12 g, 16.92 mmol). The dark red reaction mixture is stirred at rt for 18 h. The mixture is diluted with diethyl ether (250 mL) and washed with sat. aq. NaHCO₃ followed by water. The organic layer is dried over MgSO₄ and evaporated. The crude product is purified by CC on silica gel eluting with heptane:EA 4:1 to give 3-(3,5-dimethyl-4-oxiranylmethoxy-phenyl)-1-((1aS,5aR)-1,1,2-trimethyl-1,1a,5,5a-tetrahydro-3-thia-cyclopropa[a]pentalen-4-yl)-propan-1-one (1.72 g, mixture of diastereoisomers) as a pale yellow oil; LC-MS: $t_R$=1.16 min, $[M+1]^+$=411.17; ¹H NMR (CDCl₃): δ 6.85 (s, 2H), 4.04-3.97 (m, 1H), 3.77-3.69 (s, 1H), 3.52-3.44 and 3.38-3.32 (2m, 1H), 3.05-2.84 (m, 6H), 2.79 (d, J=18.8 Hz, 1H), 2.72-2.68 (m, 1H), 2.38 (s, 3H), 2.26 (s, 6H), 1.92-1.86 (m, 2H), 1.11 (s, 3H), 0.71 (s, 3H).

b) A solution of 3-(3,5-dimethyl-4-oxiranylmethoxy-phenyl)-1-((1aS,5aR)-1,1,2-trimethyl-1,1a,5,5a-tetrahydro-3-thia-cyclopropa[a]pentalen-4-yl)-propan-1-one in DMF, methanol, ethanol, or isopropanol is treated with the appropriate amine (≧4 eq.). If the amine in addition contains a carboxylic acid functionality, water and DIPEA is added to the reaction mixture. The reaction mixture is stirred at 65 to 75° C. for 2 to 24 h before it is purified by prep. HPLC (Waters Xterra MS18 19×50 mm 5 μm, 10 to 95% acetonitrile in water containing 0.5% sat. aq. ammonia, or Zorbax SB-AQ, 10 to 95% acetonitrile in water containing 0.5% formic acid) or by CC on silica gel eluting with DCM containing 10-25% methanol. To avoid salt formation, some of the compounds purified under acidic HPLC-conditions are extracted with EA from the respective HPLC fractions, evaporated and dried under high vacuum.

| Example | R | Scale (μmol) | Aspect | LC-MS $t_R$ (min) | $[M + H]^+$ |
|---|---|---|---|---|---|
| 99 | NH₂ | 731 | pale yellow foam | 0.88 | 428.18 |
| 100 | NHCH₃ | 488 | pale yellow foam | 0.89 | 442.21 |
| 101 | NHCH₂CH₃ | 10 | colourless lyophilisate | 0.91 | 456.31 |
| 102 | NHCH₂CH₂CH₃ | 10 | colourless lyophilisate | 0.93 | 470.34 |
| 103 | NHCH(CH₃)₂ | 10 | colourless lyophilisate | 0.93 | 470.31 |
| 104 | N(CH₃)₂ | 10 | colourless lyophilisate | 0.91 | 456.29 |
| 105 | N(CH₂CH₃)₂ | 15 | colourless lyophilisate | 0.94 | 484.41 |
| 106 | 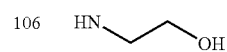 | 488 | colourless sticky foam | 0.87 | 472.21 |
| 107 | 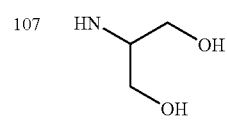 | 585 | white powder | 0.87 | 502.32 |
| 108 | 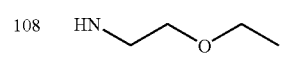 | 10 | colourless lyophilisate | 0.95 | 514.25 |
| 109 | 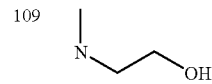 | 50 | colourless lyophilisate | 0.88 | 486.39 |

-continued
| Example | R | Scale (μmol) | Aspect | LC-MS t_R (min) | [M + H]+ |
|---|---|---|---|---|---|
| 110 | 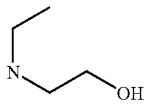 | 50 | colourless lyophilisate | 0.91 | 500.14 |
| 111 | 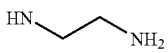 | 585 | pale yellow foam | 0.80 | 471.35 |
| 112 |  | 10 | colourless lyophilisate | 0.93 | 482.27 |
| 113 |  | 50 | colourless lyophilisate | 0.91 | 498.38 |
| 114 |  | 50 | colourless lyophilisate | 0.82 | 497.41 |
| 115 | 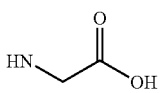 | 600 | white powder | 0.89 | 486.32 |
| 116 | 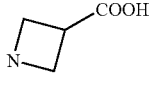 | 731 | colourless foam | 0.90 | 512.25 |
| 117 |  | 10 | colourless lyophilisate | 0.90 | 526.35 |

Example 99

¹H NMR (CDCl₃): δ 6.85 (s, 2H), 3.99-3.92 (m, 1H), 3.80-3.72(m, 2H), 3.05-2.85 (m, 2H), 2.79 (d, J=18.8 Hz, 1H), 2.38 (s, 3H), 2.25 (s, 6H), 1.95 (s br, 3H), 1.92-1.86 (m, 2H), 1.11 (s, 3H), 0.70 (s, 3H).

Example 100

¹H NMR (CDCl₃): δ 6.85 (s, 2H), 4.14-4.06 (m, 1H), 3.77 (d, J=5.3 Hz, 2H), 3.02-2.75 (m, 8H), 2.54 (s br, 2H), 2.52 (s, 3H), 2.37 8s, 3H), 2.25 (s, 6H), 1.91-1.86 (m, 2H), 1.11 (s, 3H), 0.70 (s, 3H).

Example 106

¹H NMR (CDCl₃): δ 6.85 (s, 2H), 4.14-4.06 (m, 1H), 3.80-3.75 (m, 2H), 3.72-3.67 (m, 2H), 3.03-2.80 (m, 10 H), 2.37 8s, 3H), 2.25 (s, 6H), 2.16 (s br, 3H), 1.91-1.87 (m, 2H), 1.11 (s, 3H), 0.70 (s, 3H).

Example 107

¹H NMR (CDCl₃): δ 6.85 (s, 2H), 4.15-4.07 (m, 1H), 3.80-3.72 (m, 4H), 3.68-3.60 (m, 2H), 3.04-2.75 (m, 9H), 2.55 (s br, 4H), 2.37 (s, 3H), 2.24 (s, 6H), 1.92-1.86 (m, 2H), 1.11 (s, 3H), 0.70 (s, 3H).

Example 111

¹H NMR (CDCl₃): δ 6.85 (s, 2H), 4.10-4.02 (m, 1H), 3.80-3.75 (m, 2H), 3.02-2.71 (m, 12H), 2.37 (s, 3H), 2.25 (s, 6H), 1.95 (s br, 4H), 1.91-1.86 (m, 2H), 1.11 (s, 3H), 0.70 (s, 3H).

Example 115

¹H NMR (CDCl₃): δ 6.78 (s, 2H), 4.48-4.42 (m, 1H), 3.80-3.63 (m, 4H), 3.36-3.25 (m, 2H), 3.00-2.74 (m, 6H), 2.35 (s, 3H), 2.15 (s, 6H), 1.90-1.85 (m, 2H), 1.10 (s, 3H), 0.69 (s, 3H).

Example 116

¹H NMR (CDCl₃): δ 6.84 (s, 2H), 4.64 (s br, 1H), 4.50 (s br, 2H), 4.15-3.95 (m, 2H), 3.86-3.79 (m, 1H), 3.77-3.70 (m, 1H), 3.45-3.35 (m, 1H), 3.30-3.15 (m, 2H), 3.02-2.84 (m, 7H), 2.79 (d, J=18.8 Hz, 1H), 2.37 (s, 3H), 2.22 (s, 6H), 1.92-1.85 (m, 2H), 1.11 (s, 3H), 0.70 (s, 3H).

Examples 118 to 127

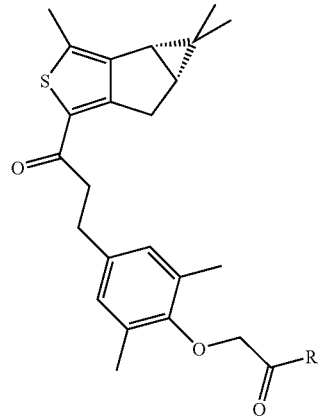

a) A solution of 3-(3,5-dimethyl-4-hydroxy-phenyl)-1-((1aS,5aR)-1,1,2-trimethyl-1,1a,5,5a-tetrahydro-3-thia-cyclopropa[a]pentalen-4-yl)-propan-1-one (350 mg, 0.988 mmol, Intermediate 10) in isopropanol (5 mL) and 3 N aq. NaOH (1.5 mL) is treated with bromoacetic acid (274 mg, 1.98 mmol). The dark red reaction mixture is stirred at 70° C. After 1, 2, 3 and 18 h an additional portion of bromoacetic acid (274 mg, 1.98 mmol) and 3N aq. NaOH (1.5 mL) is added and stirring is continued for 2 h after the last addition. The reaction mixture is diluted with EA, and washed with 1 N aq. HCl. The aq. phase is extracted with EA. The combined organic extracts are dried over MgSO₄ and evaporated. The crude product is purified by chromatography on prep. TLC plates with DCM containing 10% of methanol to give {2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-acetic acid (60 mg) as a pale yellow oil; LC-MS: $t_R$=1.07 min, [M+1]⁺=413.23.

b) A solution of {2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-acetic acid in DMF is treated with TBTU (1 eq.), DIPEA (4 eq.) and the appropriate amine (2.5 eq.). The reaction mixture is stirred at rt for 2 h before it is separated by prep. HPLC (Waters Xterra MS18, 50×20 mm ID, 10 to 95% acetonitrile in water containing 0.5% formic acid).

| Example | R | Scale (μmol) | Aspect | LC-MS $t_R$ (min) | [M + H]⁺ |
|---|---|---|---|---|---|
| 118 | NH₂ | 170 | yellow resin | 1.09 | 412.24 |
| 119 | NHCH₃ | 12 | colourless oil | 1.15 | 426.30 |
| 120 | NHCH₂CH₃ | 12 | colourless oil | 1.17 | 440.33 |
| 121 | N(CH₃)₂ | 12 | colourless oil | 1.11 | 440.32 |
| 122 | HN⌒OH | 12 | colourless oil | 1.06 | 456.32 |

-continued

| Example | R | Scale (μmol) | Aspect | LC-MS $t_R$ (min) | $[M + H]^+$ |
|---|---|---|---|---|---|
| 123 | HN–CH(OH)–CH2OH (with two OH) | 12 | colourless oil | 1.00 | 486.31 |
| 124 | HN–CH2CH2–O–ethyl | 12 | colourless oil | 1.19 | 498.40 |
| 125 | HN–CH2CH2–NH2 | 12 | colourless lyophilisate | 0.89 | 455.32 |
| 126 | HOOC-pyrrolidine (2S) | 12 | colourless lyophilisate | 1.05 | 510.24 |
| 127 | 3-COOH-pyrrolidine | 12 | colourless lyophilisate | 1.03 | 510.25 |

Example 118

$^1$H NMR (CDCl$_3$): δ 6.88 8s, 2H), 6.85 (s br, 1H), 5.77 (s br, 1H), 4.26 (s, 2H); 3.04-2.75 (m, 6H), 2.37 (s, 3H), 2.24 (s, 6H), 1.92-1.86 (m, 2H), 1.11 (s, 3H), 0.70 (s, 3H).

Examples 128 to 133

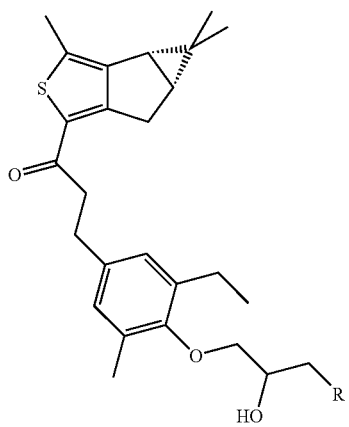

a) A solution of 3-(3-ethyl-4-hydroxy-5-methyl-phenyl)-1-((1aS,5aR)-1,1,2-trimethyl-1,1a,5,5a-tetrahydro-3-thia-cyclopropa[a]pentalen-4-yl)-propan-1-one (600 mg, 1.63 mmol, Intermediate 12) in isopropanol (5 mL) and 3 N aq. NaOH (2 mL) is treated with epichlorohydrine (366 mg, 3.95 mmol). The dark red reaction mixture is stirred at rt for 18 h. The mixture is diluted with EA and washed with water. The organic layer is dried over MgSO$_4$ and evaporated. The crude product is purified by CC on silica gel eluting with heptane: EA 4:1 to give 3-(3-ethyl-5-methoxy-4-oxiranylmethoxy-phenyl)-1-((1aS,5aR)-1,1,2-trimethyl-1,1a,5,5a-tetrahydro-3-thia-cyclopropa[a]pentalen-4-yl)-propan-1-one (524 mg, mixture of diastereoisomers) as a pale yellow oil; LC-MS: $t_R$=1.18 min, [M+1]$^+$=425.26; $^1$H NMR (CDCl$_3$): δ 6.89-6.85 (m, 2H), 4.00 (dd, J=2.9, 11.1 Hz, 1H), 3.73 (dd, J=5.9, 11.1 Hz, 1H), 3.48 (s, 2H), 3.37-3.32 (m, 1H), 3.02-2.85 (m, 5H), 2.78 (d, J=18.8 Hz, 1H), 2.64 (q, J=7.6 Hz, 2H), 2.37 (s, 3H), 2.26 8s, 3H), 1.91-1.85 (m, 2H), 1.20 (t, J=7.6 Hz, 3H), 1.11 (s, 3H), 0.70 (s, 3H).

b) A solution of 3-(3-ethyl-5-methoxy-4-oxiranylmethoxy-phenyl)-1-((1aS,5aR)-1,1,2-trimethyl-1,1a,5,5a-tetrahydro-3-thia-cyclopropa[a]pentalen-4-yl)-propan-1-one in methanol or ethanol is treated with the appropriate amine (≧4 eq.). If the amine in addition contains a carboxylic acid functionality, water and DIPEA (1 eq.) is added to the reaction mixture. The reaction mixture is stirred at 60° C. for 18 h before it is purified by prep. HPLC (Waters Xterra MS18 19×50 mm 5 μm, 10 to 95% acetonitrile in water containing 0.5% sat. aq. ammonia, or Zorbax SB-AQ, 10 to 95% acetonitrile in water containing 0.5% formic acid) or by chromatography on prep. TLC plates with DCM containing 10-25% methanol. To avoid salt formation, some of the compounds purified under acidic HPLC-conditions are extracted with EA from the respective HPLC fractions, evaporated and dried under high vacuum.

| Example | R | Scale (μmol) | Aspect | LC-MS $t_R$ (min) | $[M + H]^+$ |
|---|---|---|---|---|---|
| 128 | NH$_2$ | 118 | colourless oil | 0.89 | 442.31 |
| 129 | NHCH$_3$ | 118 | colourless oil | 0.90 | 456.46 |
| 130 | HN–CH2CH2–OH | 118 | colourless oil | 0.90 | 486.30 |
| 131 | HN–CH2CH2–NH2 | 118 | colourless oil | 0.81 | 485.33 |

-continued

| Example | R | Scale (μmol) | Aspect | LC-MS t_R (min) | [M + H]+ |
|---|---|---|---|---|---|
| 132 | HN-CH2-C(O)-OH | 118 | colourless solid | 0.90 | 500.28 |
| 133 | azetidinyl-COOH | 118 | colourless oil | 0.95 | 526.34 |

Example 133

$^1$H NMR (D$_6$-DMSO): δ 8.32 (s br, 1H), 6.91-6.87 (m, 2H), 4.44-4.35 (m, 1H), 3.69-3.58 (m, 2H), 3.51-3.25 (m, 5H), 3.04-2.93 (m, 3H), 2.80-2.70 (m, 3H), 2.55 (q, J=7.6 Hz, 2H), 2.33 (s, 3H), 2.19 (s, 3H), 1.99-1.87 (m, 2H), 1.12 (t, J=7.6 Hz, 3H), 1.07 (s, 3H), 0.65 (s, 3H).

Examples 134 to 149

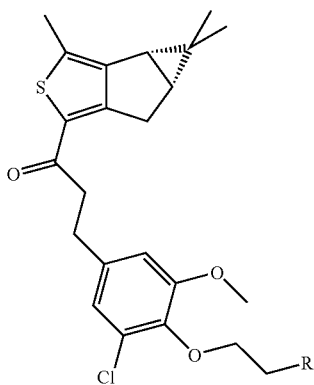

a) A solution of 3-(3-chloro-4-hydroxy-5-methoxy-phenyl)-1-((1aS,5aR)-1,1,2-trimethyl-1,1a,5,5a-tetrahydro-3-thia-cyclopropa[a]pentalen-4-yl)-propan-1-one (1.00 g, 2.56 mmol, Intermediate 14) in isopropanol (30 mL) and 2 N aq. NaOH (10 mL) is treated with 2-bromoethanol (639 mg, 5.12 mmol). The dark red reaction mixture is stirred at 70° C. for 3 h. Another portion of 2-bromoethanol (639 mg, 5.12 mmol) is added after 3, 20 and 22 h. After 26 h at 70° C., the reaction mixture is diluted with EA and washed twice with water. The organic layer is dried over MgSO$_4$ and the solvent is removed under reduced pressure. The crude product is purified by CC on silica gel eluting with heptane:EA 1:1 to give 3-[4-(3-chloro-2-hydroxy-ethoxy-5-methoxy-phenyl]-1-((1aS,5aR)-1,1,2-trimethyl-1,1a,5,5a-tetrahydro-3-thia-cyclopropa[a]pentalen-4-yl)-propan-1-one (0.60 g) as a yellow oil; LC-MS: $t_R$=1.09 min, [M+1]$^+$=435.22; $^1$H NMR (CDCl$_3$): δ 6.86-6.83 (m, 1H), 6.73-6.70 (m, 1H), 4.17-4.12 (m, 2H), 3.85 (s, 3H), 3.83-3.76 (m, 2H), 3.05-2.90 (m, 5H), 2.79 (d, J=18.8 Hz, 1H), 2.38 (s, 3H), 1.92-1.86 (m, 2H), 1.11 (s, 3H), 0.70 (s, 3H).

b) To a solution of 3-[4-(3-chloro-2-hydroxy-ethoxy-5-methoxy-phenyl]-1-((1aS,5aR)-1,1,2-trimethyl-1,1a,5,5a-tetrahydro-3-thia-cyclopropa[a]pentalen-4-yl)-propan-1-one (435 mg, 1.00 mmol) in DCM (20 mL) and DIPEA (0.274 mL, 1.60 mmol) is added methane sulfonylchloride (0.093 mL, 1.20 mmol) at 0° C. The reaction mixture is stirred at 0° C. for 40 min. The reaction mixture is diluted with DCM, washed with 0.1 N aq. NaOH followed by 10% aq. citric acid solution, dried over MgSO$_4$ and evaporated to give methanesulfonic acid 2-{2-chloro-6-methoxy-4-[3-oxo-3-((1aS,5aR)-1,1,2-trimethyl-1,1a,5,5a-tetrahydro-3-thia-cyclopropa[a]pentalen-4-yl)-propyl]-phenoxy}-ethyl ester (490 mg) as a yellow oil; LC-MS: $t_R$=1.13 min, [M+1]$^+$=513.22.

c) A solution of methanesulfonic acid 2-{2-chloro-6-methoxy-4-[3-oxo-3-((1aS,5aR)-1,1,2-trimethyl-1,1a,5,5a-tetrahydro-3-thia-cyclopropa[a]pentalen-4-yl)-propyl]-phenoxy}-ethyl ester in DMF, ethanol, or isopropanol is treated with the appropriate amine (≧4 eq.). If the amine in addition contains a carboxylic acid functionality, water and DIPEA is added to the reaction mixture. The reaction mixture is stirred at 65 to 75° C. for 4 to 48 h before it is purified by prep. HPLC (Waters Symmetry C18 19×50 mm 5 μm, Waters Xterra MS18 19×50 mm 5 μm, 10 to 95% acetonitrile in water containing 0.5% sat. aq. ammonia, or Zorbax SB-AQ, 10 to 95% acetonitrile in water containing 0.5% formic acid). To avoid salt formation, the compounds purified under acidic HPLC-conditions may be extracted with EA from the respective HPLC fractions, evaporated and dried under high vacuum.

| Example | R | Scale (μmol) | Aspect | LC-MS t_R (min) | [M + H]+ |
|---|---|---|---|---|---|
| 134 | NH$_2$ | 12 | colourless oil | 0.90 | 434.28 |
| 135 | NHCH$_3$ | 390 | pale yellow oil | 0.92 | 448.27 |
| 136 | NHCH$_2$CH$_3$ | 12 | colourless oil | 0.93 | 462.32 |
| 137 | N(CH$_3$)$_2$ | 390 | pale yellow oil | 0.93 | 462.43 |
| 138 | HN-CH2CH2-OH | 390 | pale yellow oil | 0.89 | 478.26 |
| 139 | HN-CH2-CH(OH)-CH2OH | 12 | colourless oil | 0.89 | 508.34 |

-continued

| Example | R | Scale (μmol) | Aspect | LC-MS $t_R$ (min) | [M + H]⁺ |
|---|---|---|---|---|---|
| 140 | 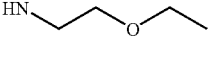 | 12 | colourless oil | 0.98 | 520.35 |
| 141 | 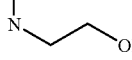 | 50 | pale yellow resin | 0.91 | 492.30 |
| 142 | 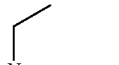 | 50 | colourless oil | 0.93 | 506.30 |
| 143 | 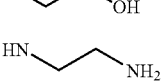 | 12 | colourless resin | 0.80 | 477.29 |
| 144 |  | 12 | colourless oil | 0.95 | 488.22 |
| 145 |  | 50 | colourless resin | 0.93 | 504.28 |
| 146 |  | 50 | colourless resin | 0.82 | 503.30 |
| 147 | 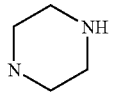 | 12 | colourless lyophilisate | 0.92 | 518.22 |
| 148 | 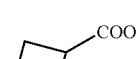 | 12 | colourless lyophilisate | 0.97 | 532.31 |
| 149 | 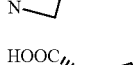 | 12 | colourless lyophilisate | 0.92 | 532.32 |

Example 135

¹H NMR (CDCl₃): δ 6.84-6.81 (m, 1H), 6.70-6.66 (m, 1H), 4.16 (t, J=5.0 Hz, 2H), 3.84 8s, 3H), 3.20 (s br, 1H), 3.10-2.90 (m, 7H), 2.78 (d, J=18.8 Hz, 1H), 2.62 (s, 3H), 2.37 (s, 3H), 1.92-1.86 (m, 2H), 1.10 (s, 3H), 0.70 (s, 3H).

Example 136

¹H NMR (CDCl₃): δ 6.82-6.80 (m, 1H), 6.68-6.66 (m, 1H), 4.14 (t, J=5.3 Hz, 2H), 3.82 8s, 3H), 3.03-2.90 (m, 7H), 2.77 (d, J=18.8 Hz, 1H), 2.58 (s, 6H), 2.37 (s, 3H), 1.91-1.86 (m, 2H), 1.10 (s, 3H), 0.69 (s, 3H).

Example 138

(as formate salt) ¹H NMR (CDCl₃): δ 8.27 (s, 1H), 6.84-6.82 (m, 1H), 6.73-6.71 (m, 1H), 6.12 (s br, 3H), 4.27-4.22 (m, 2H), 4.01-3.95 (m, 2H), 3.87 (s, 3H), 3.38-3.32 (m, 2H), 3.27-3.22 (m, 2H), 3.03-2.89 (m, 5H), 2.77 (d, J=18.8 Hz, 1H), 2.37 (s, 3H), 1.92-1.86 (m, 2H), 1.10 (s, 3H), 0.69 (s, 3H).

(free base) ¹H NMR (CDCl₃): δ 6.83-6.81 (m, 1H), 6.70-6.67 (m, 1H), 4.16-4.10 (m, 2H), 3.83 (s, 3H), 3.71-3.66 (m, 2H), 3.02-2.92 (m, 7H), 2.90-2.85 (m, 2H), 2.78 (d, J=18.8 Hz, 1H), 2.51 (s br, 2H), 2.38 (s, 3H), 1.93-1.87 (m, 2H), 1.11 (s, 3H), 0.70 (s, 3H).

Example 141

¹H NMR (CDCl₃): δ 6.82 (d, J=2.3 Hz, 1H), 6.68 8d, J=2.3 Hz, 1H), 4.10 (t, J=5.5 Hz, 2H), 3.83 8s, 3H), 3.67 (t, J=5.3

Hz, 2H), 3.02-2.92 (m, 7H), 2.83-2.75 (m, 3H), 2.50 (s, 3H), 2.38 (s, 3H), 2.25 (s br, 1H), 1.92-1.87 (m, 2H), 1.12 (s, 3H), 0.70 8s, 3H).

Example 145

$^1$H NMR (CDCl$_3$): δ 6.81 (d, J=1.8 Hz, 1H), 6.67 (d, J=1.8 Hz, 1H), 4.13-4.06 (m, 2H), 3.82 (s, 3H), 3.78-3.74 (m, 4H), 3.03-2.90 (m, 5H), 2.85-2.75 (m, 3H), 2.65-2.55 (m, 4H), 2.38 (s, 3H), 1.93-1.87 (m, 2H), 1.12 (s, 3H), 0.71 (s, 3H).

Example 146

$^1$H NMR (CDCl$_3$): δ 6.82-6.80 (m, 1H), 6.68-6.66 (m, 1H), 4.10 (t, J=5.8 Hz, 2H), 3.81 (s, 3H), 3.02-2.76 (m, 10 H), 2.66-2.54 (m, 4H), 2.38 (s, 3H), 1.92-1.89 (m, 2H), 1.83 (s br, 1H), 1.12 (s, 3H), 0.70 (s, 3H).

Examples 150 to 163

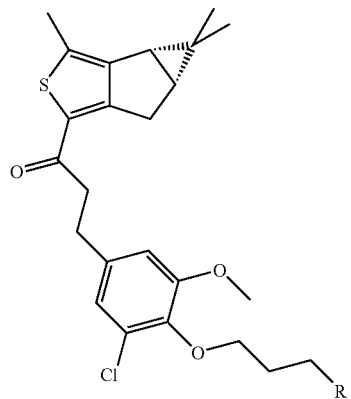

a) A solution of 3-(3-chloro-4-hydroxy-5-methoxy-phenyl)-1-((1aS,5aR)-1,1,2-trimethyl-1,1a,5,5a-tetrahydro-3-thia-cyclopropa[a]pentalen-4-yl)-propan-1-one (800 mg, 2.05 mmol, Intermediate 14) in isopropanol (30 mL) and 2 N aq. NaOH (10 mL) is treated with 3-bromopropanol (569 mg, 4.09 mmol). The dark red reaction mixture is stirred at 70° C. After 4.5 and 22 h another portion of 3-bromopropanol (569 mg, 4.09 mmol) is added. Stirring is continued for further 2 h after the last addition. The solvent is removed under reduced pressure and the residue is dissolved in EA and washed twice with water. The organic layer is dried over MgSO$_4$ and evaporated. The crude product is purified by CC on silica gel eluting with heptane:EA 1:1 to give 3-[3-chloro-4-(3-hydroxy-propoxy)-5-methoxy-phenyl]-1-((1aS,5aR)-1,1,2-trimethyl-1,1a,5,5a-tetrahydro-3-thia-cyclopropa[a]pentalen-4-yl)-propan-1-one (460 mg) as a yellow oil; LC-MS: t$_R$=1.10 min, [M+1]$^+$=449.22; $^1$H NMR (CDCl$_3$): δ 676-674 (m, 1H), 6.64-6.61 (m, 1H), 4.05 (t, J=5.5 Hz, 2H), 3.90-3.85 (m, 2H), 3.77 (s, 3H), 3.01-2.85 (m, 5H), 2.72 (d, J=18.8 Hz, 1H), 2.31 (s, 3H), 1.98-1.90 (m, 2H), 1.85-1.80 (m, 2H), 1.05 (s, 3H), 0.63 (s, 3H).

b) To a solution of 3-[3-chloro-4-(3-hydroxy-propoxy)-5-methoxy-phenyl]-1-((1aS,5aR)-1,1,2-trimethyl-1,1a,5,5a-tetrahydro-3-thia-cyclopropa[a]pentalen-4-yl)-propan-1-one (430 mg, 0.958 mmol) in DCM (20 mL) and DIPEA (0.262 mL, 1.53 mmol) is added methane sulfonylchloride (0.090 mL, 1.15 mmol) at 0° C. The reaction mixture is stirred at 0° C. for 30 min. The reaction mixture is diluted with DCM, washed with 0.1 N aq. NaOH followed by 10% aq. citric acid solution, dried over MgSO$_4$ and evaporated to give methanesulfonic acid 3-{2-chloro-6-methoxy-4-[3-oxo-3-((1aS,5aR)-1,1,2-trimethyl-1,1a,5,5a-tetrahydro-3-thia-cyclopropa[a]pentalen-4-yl)-propyl]-phenoxy}-propyl ester (2.38 g) as a brown oil; LC-MS: t$_R$=1.14 min, [M+1]$^+$=527.23.

c) A solution of methanesulfonic acid 3-{2-chloro-6-methoxy-4-[3-oxo-3-((1aS,5aR)-1,1,2-trimethyl-1,1a,5,5a-tetrahydro-3-thia-cyclopro-pa[a]pentalen-4-yl)-propyl]-phenoxy}-propyl ester in DMF, methanol, ethanol, or isopropanol is treated with the appropriate amine (≧4 eq.). If the amine in addition contains a carboxylic acid functionality, water and DIPEA is added to the reaction mixture. The reaction mixture is stirred at 65 to 75° C. for 2 to 24 h before it is purified by prep. HPLC (Waters Xterra MS18 19×50 mm 5 μm, 10 to 95% acetonitrile in water containing 0.5% sat. aq. ammonia, or Zorbax SB-AQ, 10 to 95% acetonitrile in water containing 0.5% formic acid) or by CC on silica gel eluting with DCM containing 10-25% methanol. To avoid salt formation, some of the compounds purified under acidic HPLC-conditions are extracted with EA from the respective HPLC fractions, evaporated and dried under high vacuum.

| | | | | LC-MS | |
|---|---|---|---|---|---|
| Example | R | Scale (μmol) | Aspect | t$_R$ (min) | [M + H]$^+$ |
| 150 | NH$_2$ | 12 | colourless oil | 0.92 | 448.29 |
| 151 | NHCH$_3$ | 12 | colourless oil | 0.93 | 462.34 |
| 152 | NHCH$_2$CH$_3$ | 12 | colourless oil | 0.94 | 476.32 |
| 153 | N(CH$_3$)$_2$ | 12 | colourless oil | 0.94 | 476.30 |
| 154 | HN⁀OH | 475 | pale yellow oil | 0.91 | 492.33 |
| 155 | HN⁀(OH)(OH) | 12 | colourless oil | 0.90 | 522.31 |

-continued

| Example | R | Scale (μmol) | Aspect | LC-MS t_R (min) | [M + H]+ |
|---|---|---|---|---|---|
| 156 | HN~~O~ (ethoxyethylamine) | 12 | colourless oil | 0.98 | 534.36 |
| 157 | MeN(Me)CH2CH2OH | 50 | pale yellow oil | 0.91 | 506.32 |
| 158 | EtN(Et)CH2CH2OH | 50 | pale yellow oil | 0.93 | 520.33 |
| 159 | HN~NH2 | 475 | pale yellow oil | 0.81 | 491.36 |
| 160 | morpholine | 50 | pale yellow oil | 0.93 | 518.32 |
| 161 | piperazine | 50 | pale yellow resin | 0.82 | 517.33 |
| 162 | HOOC-(2S)-pyrrolidine | 12 | colourless lyophilisate | 0.97 | 546.35 |
| 163 | 3-COOH-pyrrolidine | 12 | colourless lyophilisate | 0.93 | 546.36 |

Example 154

$^1$H NMR (CDCl$_3$): δ 6.83-6.80 (m, 1H), 6.69-6.66 (m, 1H), 4.04 (t, J=6.1 Hz, 2H), 3.82 (s, 3H), 3.64 8t, J=5.3 Hz, 2H), 3.03-2.74 (m, 10 H), 2.38 (s, 3H), 2.16 (s br, 2H), 1.96 (p, J=6.4 Hz, 2H), 1.91-1.89 (m, 2H), 1.12 (s, 3H), 0.70 (s, 3H).

Example 159

$^1$H NMR (CDCl$_3$): δ 6.84-6.80 (m, 1H), 6.69-6.66 (m, 1H), 4.07-4.00 (m, 2H), 3.83 8s, 3H), 3.03-2.70 (m, 12H), 2.38 (s, 3H), 2.04-1.94 (m, 2H), 1.92-1.86 (m, 2H), 1.81 (s br, 3H), 1.12 (s, 3H), 0.71 (s, 3H).

Examples 164 to 176

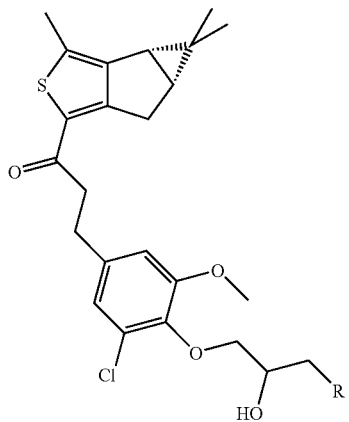

a) A solution of 3-(3-chloro-4-hydroxy-5-methoxy-phenyl)-1-((1aS,5aR)-1,1,2-trimethyl-1,1a,5,5a-tetrahydro-3-thia-cyclopropa[a]pentalen-4-yl)-propan-1-one (550 mg, 1.41 mmol, Intermediate 14) in isopropanol (10 mL) and 3 N aq. NaOH (4 mL) is treated with epichlorohydrine (0.88 g, 7.04 mmol). The dark red reaction mixture is stirred at 60° C. for 1 h. The mixture is diluted with diethyl ether (150 mL) and washed with sat. aq. NaHCO$_3$ followed by water. The organic layer is dried over MgSO$_4$ and evaporated. The crude product is purified by CC on silica gel eluting with heptane:EA 4:1 to give 3-(3-chloro-5-methoxy-4-oxiranylmethoxy-phenyl)-1-((1aS,5aR)-1,1,2-trimethyl-1,1a,5,5a-tetrahydro-3-thia-cyclopropa[a]pentalen-4-yl)-propan-1-one (400 mg) as a pale yellow oil; LC-MS: t$_R$=1.14 min, [M+1]$^+$=447.21; $^1$H NMR (CDCl$_3$): δ 6.85-6.81 (m, 1H), 6.71-6.67 (m, 1H), 4.13 (dd, J=4.1, 11.1 Hz, 1H), 4.01 (dd, J=5.9, 11.1 Hz, 1H), 3.83 (s, 3H), 3.44-3.36 (m, 1H), 3.08-2.75 (m, 8H), 2.37 (s, 3H), 1.92-1.86 (m, 2H), 1.11 (s, 3H), 0.70 (s, 3H).

b) A solution of 3-(3-chloro-5-methoxy-4-oxiranylmethoxy-phenyl)-1-((1aS,5aR)-1,1,2-trimethyl-1,1a,5,5a-tetrahydro-3-thia-cyclopropa[a]pentalen-4-yl)-propan-1-one in DMF, methanol, ethanol, or isopropanol is treated with the appropriate amine (≧4 eq.). If the amine in addition contains a carboxylic acid functionality, water and DIPEA is added to the reaction mixture. The reaction mixture is stirred at 65 to 75° C. for 2 to 24 h before it is purified by prep. HPLC (Waters Xterra MS18 19×50 mm 5 μm, 10 to 95% acetonitrile in water containing 0.5% sat. aq. ammonia, or Zorbax SB-AQ, 10 to 95% acetonitrile in water containing 0.5% formic acid) or by CC on silica gel eluting with DCM containing 10-25% methanol. To avoid salt formation, some of the compounds purified under acidic HPLC-conditions are extracted with EA from the respective HPLC fractions, evaporated and dried under high vacuum.

| Example | R | Scale (μmol) | Aspect | LC-MS t$_R$ (min) | [M + H]$^+$ |
|---|---|---|---|---|---|
| 164 | NH$_2$ | 15 | colourless oil | 0.89 | 464.32 |
| 165 | NHCH$_3$ | 15 | colourless oil | 0.91 | 478.31 |
| 166 | NHCH$_2$CH$_3$ | 15 | colourless oil | 0.92 | 492.37 |
| 167 | NHCH(CH$_3$)$_2$ | 15 | colourless oil | 0.94 | 506.32 |
| 168 | HN~~OH | 15 | colourless oil | 0.89 | 508.40 |
| 169 | HN~~(OH)CH$_2$OH | 15 | colourless oil | 0.88 | 538.35 |
| 170 | HN~~O~ | 15 | colourless oil | 0.96 | 550.40 |

-continued

| Example | R | Scale (μmol) | Aspect | LC-MS $t_R$ (min) | $[M + H]^+$ |
|---|---|---|---|---|---|
| 171 | (N-methyl-N-ethanol amine) | 50 | colourless oil | 0.89 | 522.32 |
| 172 | (N-ethyl-N-ethanol amine) | 50 | colourless oil | 0.91 | 536.33 |
| 173 | HN-CH₂-CH₂-NH₂ | 15 | colourless resin | 0.81 | 507.36 |
| 174 | morpholine | 50 | pale yellow oil | 0.91 | 534.31 |
| 175 | piperazine | 50 | colourless resin | 0.80 | 533.32 |
| 176 | HN-CH₂-COOH | 15 | colourless oil | 0.90 | 536.32 |

Example 171

$^1$H NMR (CDCl$_3$): δ 6.86-6.82 (m, 1H), 6.72-6.68 (m, 1H), 4.25-4.17 (m, 1H), 4.10-3.97 (m, 2H), 3.85 (s, 3H), 3.76 (t, J=5.2 Hz, 2H), 3.04-2.85 (m, 9H), 2.78 (d, J=18.8 Hz, 1H), 2.59 (s, 3H), 2.38 (s, 3H), 1.93-1.88 (m, 2H), 1.12 (s, 3H), 0.71 8s, 3H).

Example 174

$^1$H NMR (CDCl$_3$): δ 6.85-6.81 (m, 1H), 6.71-6.67 (m, 1H), 4.13-4.06 (m, 2H), 3.96-3.90 (m, 1H), 3.84 (s, 3H), 3.74 (t, J=4.7 Hz, 4H), 3.03-2.90 (m, 5H), 2.79 (d, J=18.8 Hz, 1H), 2.70-2.45 (m, 6H), 2.38 (s, 3H), 1.92-1.89 (m, 2H), 1.12 (s, 3H), 0.70 8s, 3H).

Example 175

$^1$H NMR (CDCl$_3$): δ 6.85-6.80 (m, 1H), 6.71-6.66 (m, 1H), 4.13-4.05 (m, 2H), 3.96-3.89 (m, 1H), 3.84 8s, 3H), 3.05-2.89 (m, 7H), 2.79 (d, J=18.8 Hz, 1H), 2.75-2.48 (m, 8H), 2.38 (s, 3H), 1.92-1.88 (m, 2H), 1.12 (s, 3H), 0.70 (s, 3H).

Examples 177 to 179

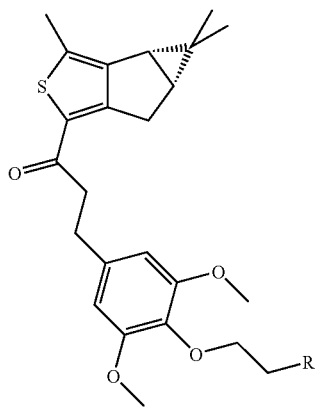

A solution of 3-(3,5-dimethoxy-4-hydroxy-phenyl)-1-((1aS,5aR)-1,1,2-trimethyl-1,1a,5,5a-tetrahydro-3-thia-cyclopropa[a]pentalen-4-yl)-propan-1-one (8 mg, 20 μmol, Intermediate 16) in isopropanol (0.8 mL) and 2 N aq. NaOH (0.25 mL) is treated with the appropriate alkylating agent (4 eq. as chloride, bromide or methane sulfonate). The reaction mixture is shaken at 70° C. for 5 h before it is purified by prep. HPLC (Waters Xterra MS18 19×50 mm 5 μm, 10 to 95% acetonitrile in water containing 0.5% formic acid) to give the desired product as colourless lyophilisate in the form of a formic acid salt.

| Example | R | Scale (μmol) | LC-MS $t_R$ (min) | $[M + H]^+$ |
|---|---|---|---|---|
| 177 | N(CH$_3$)$_2$ | 20 | 0.90 | 458.24 |
| 178 | pyrrolidine | 20 | 0.92 | 484.32 |
| 179 | morpholine | 20 | 0.91 | 500.36 |

Examples 180 to 182

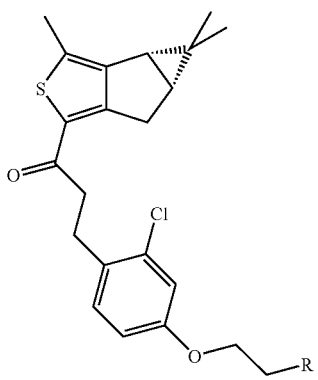

A solution of 3-(2-chloro-4-hydroxy-phenyl)-1-((1aS, 5aR)-1,1,2-trimethyl-1,1a,5,5a-tetrahydro-3-thia-cyclopropa[a]pentalen-4-yl)-propan-1-one (7 mg, 20 μmol, Intermediate 18) in isopropanol (0.8 mL) and 2 N aq. NaOH (0.25 mL) is treated with the appropriate alkylating agent (4 eq. as chloride, bromide or methane sulfonate). The reaction mixture is shaken at 70° C. for 5 h before it is purified by prep. HPLC (Waters Xterra MS18 19×50 mm 5 μm, 10 to 95% acetonitrile in water containing 0.5% formic acid) to give the desired product as colourless lyophilisate in the form of a formic acid salt.

| Example | R | Scale (μmol) | LC-MS $t_R$ (min) | $[M + H]^+$ |
|---|---|---|---|---|
| 180 | N(CH$_3$)$_2$ | 20 | 0.92 | 432.23 |
| 181 | pyrrolidine | 20 | 0.95 | 458.36 |
| 182 | morpholine | 20 | 0.93 | 474.34 |

Examples 183 to 191

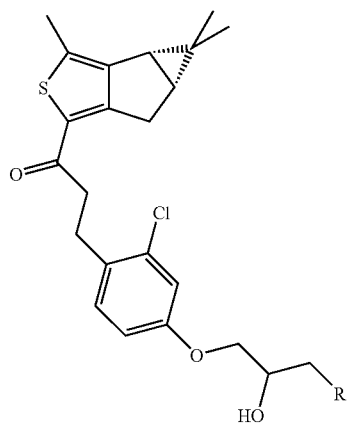

a) A solution of 3-(2-chloro-4-hydroxy-phenyl)-1-((1aS, 5aR)-1,1,2-trimethyl-1,1a,5,5a-tetrahydro-3-thia-cyclopropa[a]pentalen-4-yl)-propan-1-one (400 mg, 1.11 mmol, Intermediate 18) in isopropanol (10 mL) and 3 N aq. NaOH (6 mL) is treated with epichlorohydrine (554 mg, 4.43 mmol). The dark red reaction mixture is stirred at rt for 6 h before another portion of epichlorohydrine (554 mg, 4.43 mmol) is added. Stirring is continued for 18 h. The mixture is diluted with diethyl ether (150 mL) and washed with sat. aq. NaHCO$_3$ followed by water. The organic layer is dried over MgSO$_4$ and evaporated. The crude product is purified by CC on silica gel eluting with heptane:EA 7:3 to give 3-(2-chloro-4-oxiranylmethoxy-phenyl)-1-((1aS,5aR)-1,1,2-trimethyl-1,1a,5,5a-tetrahydro-3-thia-cyclopropa[a]pentalen-4-yl)-propan-1-one (222 mg) as a pale yellow oil; LC-MS: $t_R$=1.16 min, $[M+1]^+$=417.20.

b) A solution of 3-(2-chloro-4-oxiranylmethoxy-phenyl)-1-((1aS,5aR)-1,1,2-trimethyl-1,1a,5,5a-tetrahydro-3-thia-cyclopropa[a]pentalen-4-yl)-propan-1-one in DMF, methanol, ethanol, or isopropanol is treated with the appropriate amine (≧4 eq.). If the amine in addition contains a carboxylic acid functionality, water and DIPEA is added to the reaction mixture. The reaction mixture is stirred at 65 to 75° C. for 4 h. In the case of volatile amines, the solvent is removed under reduced pressure and the residue is purified by chromatography on prep. TLC plates using DCM containing 10-20% methanol. In the case of non-volatile amines, the reaction mixture is diluted with diethyl ether and washed twice with water. The organic layer is dried over MgSO$_4$ and the solvent is evaporated. The crude product is purified by chromatography on prep. TLC plates using DCM containing 10-20% methanol. Small-scale reactions (<50 mg) are separated by prep. HPLC (Waters Xterra MS18, 19×50 mm, 5 μm, 10 to 95% acetonitrile in water containing 0.5% formic acid).

mmol, Intermediate 20) in isopropanol (10 mL) and 3 N aq. NaOH (6 mL) is treated with epichlorohydrine (631 mg, 5.05 mmol). The reaction mixture is stirred at rt for 9 h before it is diluted with diethyl ether (150 mL) and washed with sat. aq. NaHCO$_3$ followed by water. The organic layer is dried over MgSO$_4$ and evaporated. The crude product is purified by CC

| Example | R | Scale (μmol) | Aspect | LC-MS $t_R$ (min) | [M + H]$^+$ |
|---|---|---|---|---|---|
| 183 | NH$_2$ | 168 | colourless foam | 0.88 | 434.21 |
| 184 | NHCH$_3$ | 168 | colourless resin | 0.90 | 448.19 |
| 185 | NHCH$_2$CH$_3$ | 15 | colourless resin | 0.92 | 462.34 |
| 186 | NHCH(CH$_3$)$_2$ | 15 | colourless resin | 0.94 | 476.43 |
| 187 | HN~~OH | 168 | colourless foam | 0.88 | 478.28 |
| 188 | HN~~OH (with OH) | 15 | colourless resin | 0.89 | 508.29 |
| 189 | HN~~O~ | 15 | colourless resin | 0.96 | 520.42 |
| 190 | HN~~NH$_2$ | 15 | colourless resin | 0.81 | 477.37 |
| 191 | HN~~C(O)OH | 15 | colourless resin | 0.91 | 506.24 |

Example 187

$^1$H NMR (CDCl$_3$): δ 7.18 (d, J=8.8 Hz, 1H), 6.93 (d, J=1.8 Hz, 1H), 6.75 (dd, J=1.8, 8.8 Hz, 1H), 4.10-4.02 (m, 1H), 3.98-3.93 (m, 2H), 3.74-3.66 (m, 2H), 3.10-2.74 (m, 10H), 2.37 (s, 3H), 1.94 8s br, 3H), 1.91-1.86 (m, 2H), 1.10 (s, 3H), 0.69 (s, 3H).

Examples 192 to 194

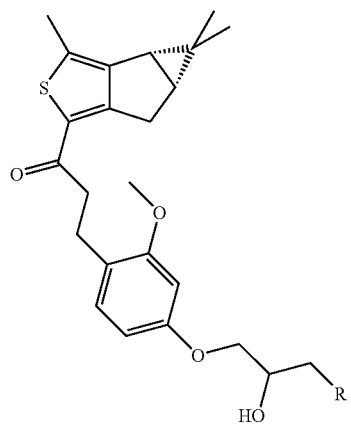

a) A solution of 3-(4-hydroxy-2-methoxy-phenyl)-1-((1aS,5aR)-1,1,2-trimethyl-1,1a,5,5a-tetrahydro-3-thia-cyclopropa[a]pentalen-4-yl)-propan-1-one (600 mg, 1.68 on silica gel eluting with heptane:EA 4:1 to give 3-(2-methoxy-4-oxiranylmethoxy-phenyl)-1-((1aS,5aR)-1,1,2-trimethyl-1,1a,5,5a-tetrahydro-3-thia-cyclopropa[a]pentalen-4-yl)-propan-1-one (459 mg) as an almost colourless oil; LC-MS: $t_R$=1.13 min, [M+1]$^+$=413.28.

b) A solution of 3-(2-methoxy-4-oxiranylmethoxy-phenyl)-1-((1aS,5aR)-1,1,2-trimethyl-1,1a,5,5a-tetrahydro-3-thia-cyclopropa[a]pentalen-4-yl)-propan-1-one methanol or ethanol is treated with the appropriate amine (≧4 eq.). The reaction mixture is stirred at 65° for 2-4 h. In the case of volatile amines, the solvent is removed under reduced pressure and the residue is purified by chromatography on prep. TLC plates using DCM containing 10-20% methanol. In the case of non-volatile amines, the reaction mixture is diluted with diethyl ether and washed twice with water. The organic layer is dried over MgSO$_4$ and the solvent is evaporated. The crude product is purified by chromatography on prep. TLC plates using DCM containing 10-20% methanol.

| Example | R | Scale (μmol) | Aspect | LC-MS $t_R$ (min) | [M + H]$^+$ |
|---|---|---|---|---|---|
| 192 | NH$_2$ | 272 | colourless foam | 0.86 | 430.27 |
| 193 | NHCH$_3$ | 272 | colourless foam | 0.88 | 444.30 |
| 194 | HN~~OH | 272 | colourless foam | 0.86 | 474.35 |

Example 193

$^1$H NMR (CDCl$_3$): δ 7.06 (d, J=8.2 Hz, 1H), 6.47 (d, J=1.8 Hz, 1H), 6.40 (dd, J=1.8, 8.2 Hz, 1H), 4.10-4.03 (m, 1H), 3.99-3.94 (m, 2H), 3.79 (s, 3H), 3.02-2.88 (m, 5H), 2.83-2.70 (m, 3H), 2.49 (s, 3H), 2.36 (s, 3H), 2.06 (s br, 2H), 1.91-1.84 (m, 2H), 1.10 (s, 3H), 0.70 (s, 3H).

Examples 195 to 198

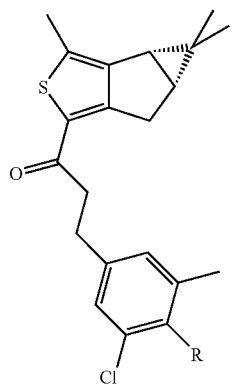

A solution of 3-(3-chloro-4-hydroxy-5-methyl-phenyl)-1-((1aS,5aR)-1,1,2-trimethyl-1,1a,5,5a-tetrahydro-3-thia-cyclo-propa[a]pentalen-4-yl)-propan-1-one (7.5 mg, 20 μmol) in isopropanol (0.8 mL) and 2 N aq. NaOH (0.25 mL) is treated with the appropriate alkylating agent (5 eq. as chloride, bromide or methane sulfonate). The reaction mixture is shaken at 70° C. for 3 h before it is purified by prep. HPLC (Waters Xterra MS18 19×50 mm 5 μm, 10 to 95% acetonitrile in water containing 0.5% formic acid) to give the desired product as colourless lyophilisate.

| | | | LC-MS | |
|---|---|---|---|---|
| Example | R | Scale (μmol) | $t_R$ (min) | [M + H]$^+$ |
| 195 | OH, O, OCH$_3$ | 20 | 1.12 | 463.36 |
| 196 | O, N(CH$_3$)$_2$ | 20 | 0.94 | 446.31 |
| 197 | O, N-pyrrolidine | 20 | 0.96 | 472.46 |
| 198 | O, N-morpholine | 20 | 0.94 | 488.38 |

Examples 199 to 202

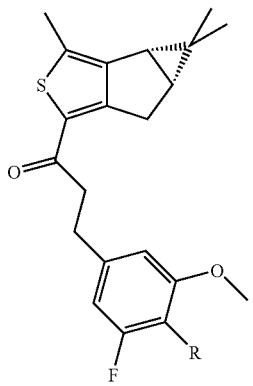

A solution of 3-(3-fluoro-4-hydroxy-5-methoxy-phenyl)-1-((1aS,5aR)-1,1,2-trimethyl-1,1a,5,5a-tetrahydro-3-thia-cyclopropa[a]pentalen-4-yl)-propan-1-one (7.5 mg, 20 μmol) in isopropanol (0.8 mL) and 2 N aq. NaOH (0.25 mL) is treated with the appropriate alkylating agent (5 eq. as chloride, bromide or methane sulfonate). The reaction mixture is shaken at 70° C. for 3 h before it is purified by prep. HPLC (Waters Xterra MS18 19×50 mm 5 μm, 10 to 95% acetonitrile in water containing 0.5% formic acid) to give the desired product as colourless lyophilisate.

| | | | LC-MS | |
|---|---|---|---|---|
| Example | R | Scale (μmol) | $t_R$ (min) | [M + H]$^+$ |
| 199 | OH, O, OCH$_3$ | 20 | 1.08 | 463.37 |
| 200 | O, N(CH$_3$)$_2$ | 20 | 0.91 | 446.38 |
| 201 | O, N-pyrrolidine | 20 | 0.94 | 472.48 |
| 202 | O, N-morpholine | 20 | 0.92 | 488.41 |

Examples 203 to 205

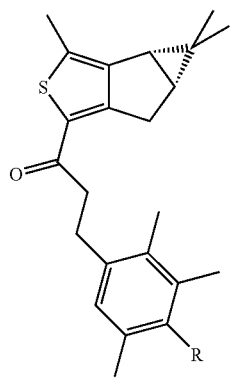

A solution of 3-(4-hydroxy-2,3,5-trimethyl-phenyl)-1-((1aS,5aR)-1,1,2-trimethyl-1,1a,5,5a-tetrahydro-3-thia-cyclopropa[a]pentalen-4-yl)-propan-1-one (7.5 mg, 20 µmol) in isopropanol (0.8 mL) and 2 N aq. NaOH (0.25 mL) is treated with the appropriate alkylating agent (5 eq. as chloride, bromide or methane sulfonate). The reaction mixture is shaken at 70° C. for 3 h before it is purified by prep. HPLC (Waters Xterra MS18 19×50 mm 5 µm, 10 to 95% acetonitrile in water containing 0.5% formic acid) to give the desired product as colourless lyophilisate.

| Example | R | Scale (µmol) | LC-MS $t_R$ (min) | $[M + H]^+$ |
|---|---|---|---|---|
| 203 | OH, O, OCH₃ | 20 | 1.12 | 457.35 |
| 204 | O, N | 20 | 0.94 | 440.40 |
| 205 | O, N, O (morpholine) | 20 | 0.95 | 482.45 |

Examples 206 to 208

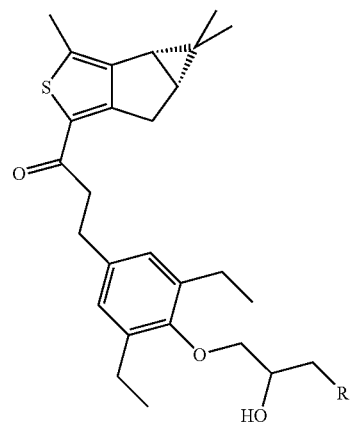

a) A solution of 3-(3,5-diethyl-4-hydroxy-phenyl)-1-((1aS,5aR)-1,1,2-trimethyl-1,1a,5,5a-tetrahydro-3-thia-cyclopropa[a]pentalen-4-yl)-propan-1-one (450 mg, 1.18 mmol) in isopropanol (10 mL) and 3 N aq. NaOH (6 mL) is treated with epichlorohydrine (326 mg, 3.53 mmol). The reaction mixture is stirred at rt for 18 h before it is diluted with EA (150 mL) and washed with water. The organic layer is dried over MgSO₄ and evaporated. An aliquot of the crude 3-(3,5-diethyl-4-oxiranylmethoxy-phenyl)-1-((1aS,5aR)-1,1,2-trimethyl-1,1a,5,5a-tetrahydro-3-thia-cyclopropa[a]pentalen-4-yl)-propan-1-one dissolved in methanol or ethanol is treated with the appropriate amine (≧4 eq.). The reaction mixture is stirred at 65-70° C. for 18 h. The solvent is removed under reduced pressure and the residue is purified by prep. HPLC to give the desired products as a colourless lyophilisate or resin.

| Example | R | Scale (µmol) | LC-MS $t_R$ (min) | $[M + H]^+$ |
|---|---|---|---|---|
| 206 | NH₂ | 137 | 0.92 | 456.26 |
| 207 | NHCH₃ | 137 | 0.93 | 470.31 |
| 208 | HN-CH₂CH₂-OH | 137 | 0.91 | 500.30 |

Example 209

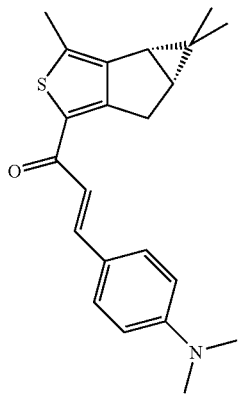

A solution of 4-dimethylaminobenzaldehyde (72 mg, 0.48 mmol), (1aS,5aR)-1-(1,1,2-trimethyl-1,1a,5,5a-tetrahydro-3-thia-cyclopropa[a]pentalen-4-yl)-ethanone (88 mg, 0.40 mmol), NaOH (640 mg, 16.0 mmol) in ethanol (5 mL) is stirred at rt for 5 h. The reaction mixture is diluted with water and the pH is adjusted to pH 10 with sat. aq. NaHCO$_3$ solution. The mixture is extracted with diethyl ether (2×100 mL). The organic extracts are washed with water, dried over MgSO$_4$ and evaporated. The crude product is crystallized from diethyl ether/heptane to give 3-(4-dimethylamino-phenyl)-1-((1aS,5aR)-1,1,2-trimethyl-1,1a,5,5a-tetrahydro-3-thia-cyclopropa[a]pentalen-4-yl)-propenone (94 mg) as an orange solid; LC-MS: $t_R$=1.15 min, [M+1]$^+$=352.28.

Example 210

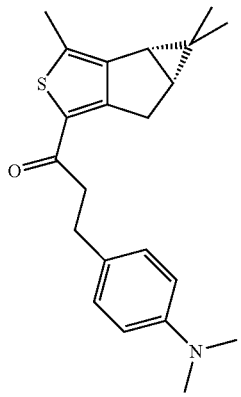

A solution of 3-(4-dimethylamino-phenyl)-1-((1aS,5aR)-1,1,2-trimethyl-1,1a,5,5a-tetrahydro-3-thia-cyclopropa[a]pentalen-4-yl)-propenone (94 mg, 0.27 mmol) in ethanol (5 mL) is treated with Pd/C (40 mg, 10% Pd) and the mixture is stirred at rt for 2 h under 1.5 bar H$_2$. The mixture is filtered, the filtrate is evaporated and the crude product is purified by CC on silica gel eluting with heptane:EA 1:1 to give 3-(4-dimethylamino-phenyl)-1-((1aS,5aR)-1,1,2-trimethyl-1,1a,5,5a-tetrahydro-3-thia-cyclopropa[a]pentalen-4-yl)-propan-1-one (70 mg) as a yellow oil; LC-MS: $t_R$=0.88 min, [M+1]$^+$=354.28.

Example 211

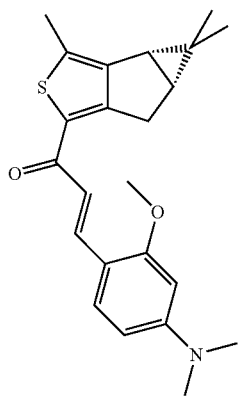

A solution of 4-dimethylamino-2-methoxybenzaldehyde (86 mg, 0.48 mmol), (1aS,5aR)-1-(1,1,2-trimethyl-1,1a,5,5a-tetrahydro-3-thia-cyclopropa[a]pentalen-4-yl)-ethanone (88 mg, 0.40 mmol), and NaOH (640 mg, 16.0 mmol) in ethanol (5 mL) is stirred at rt for 3 h. The reaction mixture is diluted with water and the pH is adjusted to pH 10 with sat. aq. NaHCO$_3$ solution. The mixture is extracted with diethyl ether (2×100 mL). The organic extracts are washed with water, dried over MgSO$_4$ and evaporated. The crude product is crystallized from diethyl ether/heptane to give 3-(4-dimethylamino-2-methoxyphenyl)-1-((1aS,5aR)-1,1,2-trimethyl-1,1a,5,5a-tetrahydro-3-thia-cyclopropa[a]pentalen-4-yl)-propenone (94 mg) as a yellow-orange solid; LC-MS: $t_R$=1.16 min, [M+1]$^+$=382.27.

Example 212

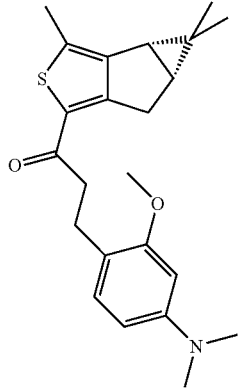

A solution of 3-(4-dimethylamino-2-methoxyphenyl)-1-((1aS,5aR)-1,1,2-trimethyl-1,1a,5,5a-tetrahydro-3-thia-cyclopropa[a]pentalen-4-yl)-propenone (94 mg, 0.25 mmol) in ethanol (5 mL) is treated with Pd/C (40 mg, 10% Pd) and the mixture is stirred at rt for 2 h under 1.5 bar H$_2$. The mixture is filtered, the filtrate is evaporated and the crude product is purified by CC on silica gel eluting with heptane:EA 1:1 to give 3-(4-dimethylamino-2-methoxyphenyl)-1-((1aS,5aR)-1,1,2-trimethyl-1,1a,5,5a-tetrahydro-3-thia-cyclopropa[a]pentalen-4-yl)-propan-1-one (72 mg) as a yellow oil; LC-MS: $t_R$=0.90 min, [M+1]$^+$=384.27.

Example 213

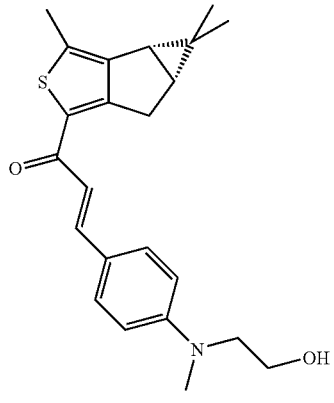

A solution of N-methyl-N-2-hydroxyethyl-4-aminobenzaldehyde (86 mg, 0.48 mmol), (1aS,5aR)-1-(1,1,2-trimethyl-1,1a,5,5a-tetrahydro-3-thia-cyclopropa[a]pentalen-4-yl)-ethanone (88 mg, 0.40 mmol), and NaOH (640 mg, 16.0 mmol) in ethanol (5 mL) is stirred at rt for 18 h. The reaction mixture is diluted with water and the pH is adjusted to pH 10 with sat. aq. NaHCO$_3$ solution. The mixture is extracted with diethyl ether (2×100 mL). The organic extracts are washed with water, dried over MgSO$_4$ and evaporated. The crude product is purified on prep. TLC plates with heptane:EA 1:1 to give 3-{4-[(2-hydroxy-ethyl)-methyl-amino]-phenyl}-1-((1aS,5aR)-1,1,2-trimethyl-1,1a,5,5a-tetrahydro-3-thia-cyclopro-pa[a]pentalen-4-yl)-propenone (88 mg) as an orange-red solid; LC-MS: $t_R$=1.07 min, [M+1]$^+$=382.37.

Example 214

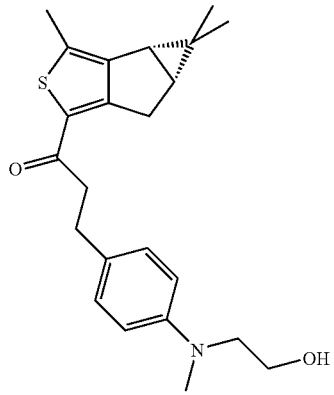

A solution of 3-{4-[(2-hydroxy-ethyl)-methyl-amino]-phenyl}-1-((1aS,5aR)-1,1,2-trimethyl-1,1a,5,5a-tetrahydro-3-thia-cyclopro-pa[a]pentalen-4-yl)-propenone (88 mg, 0.23 mmol) in ethanol (5 mL) and THF (5 mL) is treated with Pd/C (40 mg, 10% Pd) and the mixture is stirred at rt for 2 h under 1.5 bar H$_2$. The mixture is filtered, the filtrate is evaporated and the crude product is purified on prep. TLC plates with heptane:EA 1:1 to give 3-{4-[(2-hydroxy-ethyl)-methyl-amino]-phenyl}-1-((1aS,5aR)-1,1,2-trimethyl-1,1a,5,5a-tetrahydro-3-thia-cyclopropa[a]pentalen-4-yl)-propan-1-one (49 mg) as a yellow oil; LC-MS: $t_R$=0.85 min, [M+1]$^+$=384.27.

Example 215

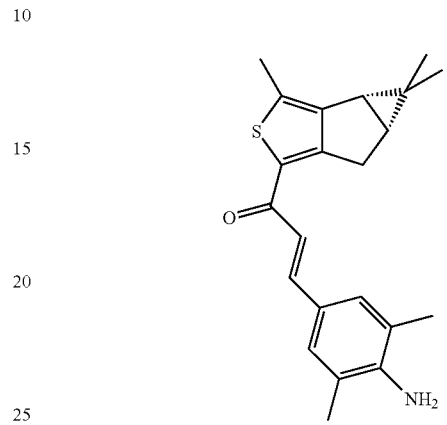

A solution of 4-amino-3,5-dimethylbenzaldehyde (746 mg, 5.0 mmol), (1aS,5aR)-1-(1,1,2-trimethyl-1,1a,5,5a-tetrahydro-3-thia-cyclopropa[a]pentalen-4-yl)-ethanone (550 mg, 2.5 mmol) in 10% NaOH in methanol (14 mL) is stirred at 70° C. for 1.5 h. The reaction mixture is diluted with water (180 mL) and extracted with EA (2×80 mL). The organic extracts are dried over Na$_2$SO$_4$ and evaporated. The crude product is purified by prep. HPLC (Phenomenex Aqua, 75×30 mm ID, 10 μm, 10-95% acetonitrilie in water containing 0.5% formic acid) to give 3-(4-amino-3,5-dimethyl-phenyl)-1-((1aS,5aR)-1,1,2-trimethyl-1,1a,5,5a-tetrahydro-3-thia-cyclopropa[a]pentalen-4-yl)-propenone (560 mg) as a yellow resin; LC-MS: $t_R$=1.12 min, [M+1]$^+$=352.24.

Example 216

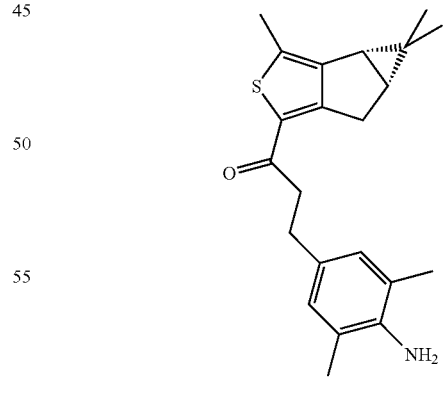

A solution of 3-(4-amino-3,5-dimethyl-phenyl)-1-((1aS,5aR)-1,1,2-trimethyl-1,1a,5,5a-tetrahydro-3-thia-cyclopropa[a]pentalen-4-yl)-propenone (527 mg, 1.5 mmol) in ethanol (20 mL) is treated with Pd/C (400 mg, 10% Pd) and the mixture is stirred at rt for 18 h under 1 bar H$_2$. The mixture is filtered, the filtrate is evaporated and dried to give 3-(4-amino-3,5-dimethyl-phenyl)-1-((1aS,5aR)-1,1,2-trimethyl- 1,1a,5,5a-tetrahydro-3-thia-cyclopropa[a]pentalen-4-yl)-propan-1-one (490 mg) as a yellow resin; LC-MS: $t_R$=0.92 min, $[M+1]^+$=354.30; $^1$H NMR (CDCl$_3$): δ 6.80 (s, 2H), 3.47 (s br, 2H), 3.05-2.75 (m, 6H), 2.37 (s, 3H), 2.16 (s, 6H), 1.89-1.85 (m, 2H), 1.11 (s, 3H), 0.70 (s, 3H).

Examples 217 to 222

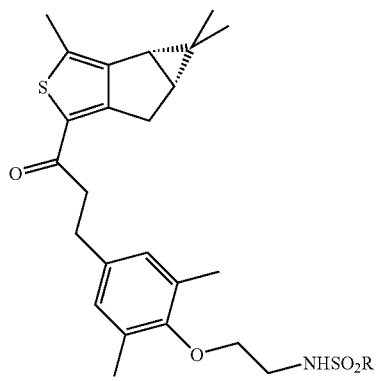

A solution of 3-[4-(2-amino-ethoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one (20 mg, 0.051 mmol) and DIPEA (10.4 mg, 0.081 mmol) in DCM (2 mL) is treated with the appropriate sulfonylchloride or sulfamoylchloride (1.2 eq.) and the reaction mixture is stirred at rt for 2 h. The solvent is removed in vacuo and the crude product is purified by prep. HPLC (Waters Zorbax SB AQ, 10 to 95% acetonitrile in water containing 0.5% formic acid). Product containing fractions are combined, diluted with EA and washed with water. The organic phase is evaporated and dried to give the desired product as a colourless resin.

|  |  | Scale | LC-MS | |
|---|---|---|---|---|
| Example | R | (μmol) | $t_R$ (min) | $[M + H]^+$ |
| 217 | —CH$_3$ | 51 | 1.07 | 476.04 |
| 218 | —CH$_2$CH$_3$ | 51 | 1.12 | 490.24 |
| 219 | —CH$_2$CH$_2$CH$_3$ | 51 | 1.14 | 504.25 |
| 220 | —NH—CH$_2$CH$_3$ | 51 | 1.07 | 505.06 |
| 221 | —NH—CH$_2$CH$_2$CH$_2$CH$_3$ | 51 | 1.14 | 533.06 |
| 222 | —N(CH$_3$)$_2$ | 51 | 1.14 | 505.06 |

Example 217

$^1$H NMR (CDCl$_3$): δ 6.87 (s, 2H), 4.84 (t br, J=6 Hz, 1H), 3.91-3.85 (m, 2H), 3.56-3.43 (m, 2H), 3.05 (s, 3H), 3.02-2.85 (m, 5H), 2.79 (d, J=18.8 Hz, 1H), 2.38 (s, 3H), 2.25 (s, 6H), 1.93-1.86 (m, 2H), 1.12 (s, 3H), 0.71 (s, 3H).

Examples 223 to 227

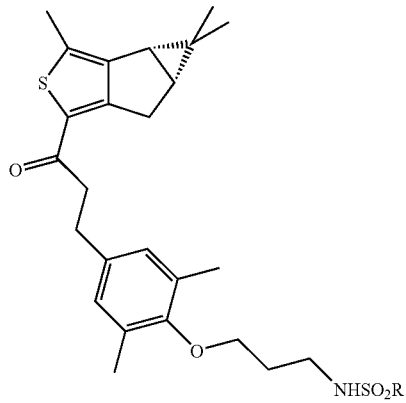

A solution of 3-[4-(3-amino-propoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one (15 mg, 0.037 mmol) and DIPEA (7.5 mg, 0.059 mmol) in DCM (2 mL) is treated with the appropriate sulfonylchloride or sulfamoylchloride (1.2 eq.) and the reaction mixture is stirred at rt for 1 h. The solvent is removed in vacuo and the crude product is purified chromatography on prep. TLC plates with heptane:EA 1:1 to give the desired product as a pale yellow resin.

|  |  | Scale | LC-MS | |
|---|---|---|---|---|
| Example | R | (μmol) | $t_R$ (min) | $[M + H]^+$ |
| 223 | —CH$_3$ | 37 | 1.06 | 490.05 |
| 224 | —CH$_2$CH$_3$ | 37 | 1.11 | 504.07 |
| 225 | —CH$_2$CH$_2$CH$_3$ | 37 | 1.15 | 518.08 |
| 226 | —NH—CH$_2$CH$_3$ | 37 | 1.11 | 519.08 |
| 227 | —N(CH$_3$)$_2$ | 37 | 1.14 | 519.05 |

Examples 228 to 230

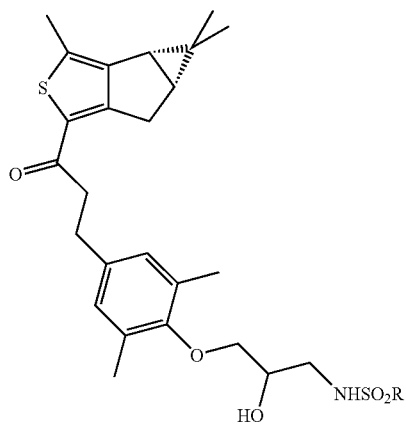

A solution of 3-[4-(3-amino-2-hydroxy-propoxy)-3,5-dimethyl-phenyl]-1-((1aS,5aR)-1,1,2-trimethyl-1,1a,5,5a- tetrahydro-3-thia-cyclopropa[a]pentalen-4-yl)-propan-1-one (20 mg, 0.049 mmol) in DMSO (2 mL) is treated with the appropriate sulfonamide potassium salt (3 eq.) and the reaction mixture is stirred at 50° C. for 20 h. The reaction mixture is separated by prep. HPLC (Water Zorbax SB AQ, 10-95% acetonitrile in water containing 0.5% formic acid) to give the desired product as a pale yellow resin.

| Example | R | Scale (µmol) | LC-MS $t_R$ (min) | $[M + H]^+$ |
|---|---|---|---|---|
| 228 | —CH$_3$ | 49 | 1.04 | 506.18 |
| 229 | —CH$_2$CH$_3$ | 49 | 1.05 | 520.23 |
| 230 | —CH$_2$CH$_2$CH$_3$ | 49 | 1.08 | 534.22 |

Example 228

$^1$H NMR (CDCl$_3$). δ 6.86 (s, 2H), 4.81 (t br, J=6 Hz, 1H), 4.21-4.12 (m, 1H), 3.86-3.75 (m, 2H), 3.51-3.42 (m, 1H), 3.37-3.25 (m, 1H), 3.02 (s, 3H), 3.01-2.85 (m, 5H), 2.79 (d, J=18.8 Hz, 1H), 2.38 (s, 3H), 2.24 (s, 6H), 1.93-1.87 (m, 2H), 1.12 (s, 3H), 0.71 (s, 3H).

Example 231

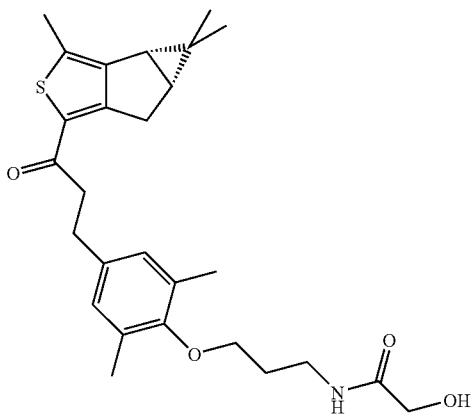

A solution of 3-[4-(3-amino-propoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one (18 mg, 0.043 mmol, Example 81) in DCM (2 mL) is treated with DIPEA (22 mg, 0.171 mmol), TBTU (19 mg, 0.06 mmol) and glycolic acid (5 mg, 0.064 mmol). The mixture is stirred at rt for 1.5 h before it is separated by chromatography on prep. TLC plates with DCM:methanol 9:1 to give N-(3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-propyl)-2-hydroxy-acetamide (7 mg) as a white solid; LC-MS: $t_R$=1.01 min, [M+1]$^+$=470.07.

Example 232

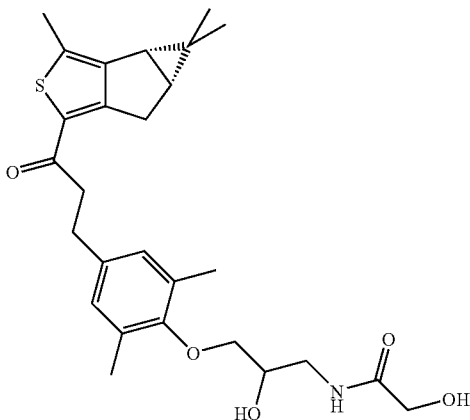

To a solution of 3-[4-(3-amino-2-hydroxy-propoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one (17.6 mg, 42 µmol) in DCM (2 mL) is added DIPEA (21 mg, 165 µmol), TBTU (19 mg, 58 µmol) and hydroxy-acetic acid (5 mg, 62 µmol) and the reaction mixture is stirred at rt for 1.5 h before it is separated on prep. TLC plates with DCM containing 10% of methanol. This gives N-(3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-2-hydroxy-propyl)-2-hydroxy-acetamide (7 mg) as a colourless solid; LC-MS: $t_R$=0.98 min, [M+1]$^+$=486.04.

Example 233

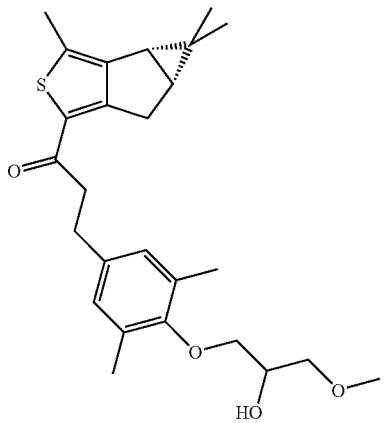

3-[4-(2-Hydroxy-3-methoxy-propoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one is prepared by treating 3-(3,5-dimethyl-4-oxiranylmethoxy-phenyl)-1-((1aS,5aR)-1,1,2-trimethyl-1,1a,5,5a-tetrahydro-3-thia-cyclopropa[a]pentalen-4-yl)-propan-1-one with sodium methylate in methanol at 65° C. for 16 h in analogy to the procedure given in Example 99; LC-MS: $t_R$=1.10 min, [M+1]$^+$=443.18.

Example 234

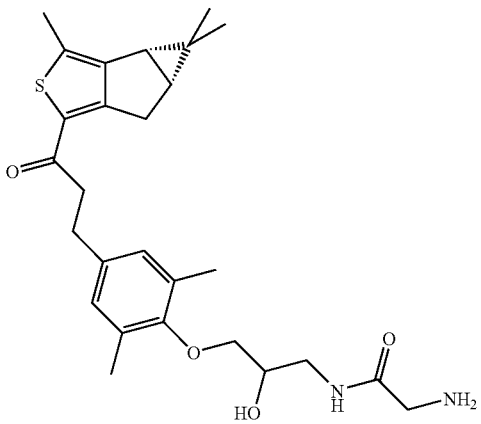

A solution of 3-[4-(3-amino-2-hydroxy-propoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one (70 mg, 0.164 mmol, Example 99) in DCM (3 mL) is treated with DIPEA (85 mg, 0.655 mmol), TBTU (74 mg, 0.23 mmol) and tert. butoxycarbonyl glycine (43 mg, 0.246 mmol) and the reaction mixture is stirred at rt for 1 h. The mixture is diluted with EA and washed with sat. aq. NaHCO$_3$ and brine. The organic extract is dried over MgSO$_4$, filtered and evaporated. The residue is dissolved in DCM (2 mL) and TFA (0.1 mL) is added. The mixture is stirred at rt for 3 h before another portion of TFA (0.02 mL) is added. Stirring is continued for 1 h. The mixture is diluted with EA, washed twice with a sat. aq. NaHCO$_3$ solution, dried over MgSO$_4$, filtered and evaporated. The crude product is purified by chromatography on prep. TLC plates with DCM:methanol 9:1 to give 2-amino-N-(3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-2-hydroxy-propyl)-acetamide (3 mg) as a colourless resin; LC-MS: t$_R$=0.86 min, [M+1]$^+$=485.33.

Example 235

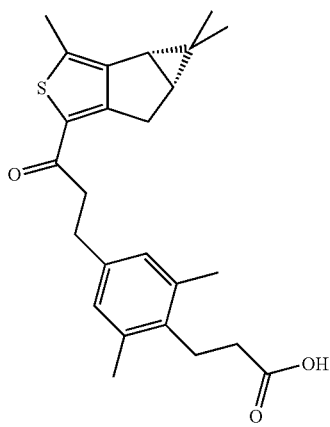

a) To an ice-cooled solution of 4-hydroxy-3,5-dimethylbenzaldehyde (6.0 g, 40 mmol) in DCM (60 mL) and pyridine (10 mL), trifluoromethanesulfonic acid anhydride (12.4 g, 44 mmol) is added over a period of 20 min. Upon complete addition, the ice bath is removed and the reaction is stirred for further 2 h at rt. The mixture is diluted with EA (200 mL), washed three times with water, dried over MgSO$_4$, filtered and evaporated. The residue is purified by flash chromatography on silica gel eluting with heptane:EA 4:1 to give trifluoro-methanesulfonic acid 4-formyl-2,6-dimethyl-phenyl ester (5.9 g) as a colourless oil; LC-MS: t$_R$=1.04 min.

b) To a stirred solution of the above triflate (5.8 g, 20.6 mmol) in dry DMF (75 mL) is sequentially added triethylamine (4.16 g, 41.1 mmol), methyl acrylate (17.7 g, 206 mmol), DPPP (466 mg, 1.13 mmol) and Pd(OAc)$_2$ (231 mg, 1.03 mmol) under nitrogen. The mixture is stirred at 115° C. for 5 h, cooled to rt, diluted with diethyl ether (350 mL) and washed twice with 1 N aq. HCl and once with a sat. aq. NaHCO$_3$ solution. The organic extract is dried over MgSO$_4$, filtered and evaporated. The residue is purified by flash chromatography on silica gel eluting with heptane: EA 5:1 to give 3-(4-formyl-2,6-dimethyl-phenyl)-acrylic acid methyl ester (3.6 g) as a colourless liquid; LC-MS: t$_R$=0.96 min.

c) A suspension of 3-(4-formyl-2,6-dimethyl-phenyl)-acrylic acid methyl ester (3.6 g, 16.5 mmol) in methanol (70 mL) and 1.25 N aq. NaOH (45 mL) is stirred at rt for 1 h. The methanol is evaporated and the aq. solution is extracted twice with DCM. The aq. layer is acidified with 2 N aq. HCl and extracted twice with EA. The combined organic extracts are dried over MgSO$_4$, filtered and evaporated. The obtained solid is recrystalized from EA (100 mL) to give 3-(4-formyl-2,6-dimethyl-phenyl)-acrylic acid (2.4 g) as a white solid; LC-MS: t$_R$=0.84 min.

d) A solution of 1-((1aS,5aR)-1,1,2-trimethyl-1,1a,5,5a-tetrahydro-3-thia-cyclopropa[a]pentalen-4-yl)-ethanone (150 mg, 0.681 mmol) and 3-(4-formyl-2,6-dimethyl-phenyl)-acrylic acid (140 mg, 0.681 mmol) in methanolic NaOH (7 mL, 10 g NaOH/100 mL methanol) is stirred at rt for 3 days. The mixture is cooled to 0° C. and then neutralized with 2 N aq. HCl. The mixture is diluted with DCM and washed with water followed by brine. The organic extract is dried over MgSO$_4$, filtered and evaporated. The crude product is purified by prep. HPLC (Grom-Sil 120 ODS-4-HE, 30×75 mm, 10 µm, acetonitrile/water(0.5% HCOOH), 30% to 95% acetonitrile) to give 3-{2,6-dimethyl-4-[3-oxo-3-((1aS,5aR)-1,1,2-trimethyl-1,1a,5,5a-tetrahydro-3-thia-cyclopropa[a]pentalen-4-yl)-propenyl]-phenyl}-acrylic acid (110 mg) as a yellow solid; LC-MS: t$_R$=1.13 min, [M+1]$^+$=407.32.

e) To a solution of 3-{2,6-dimethyl-4-[3-oxo-3-((1aS,5aR)-1,1,2-trimethyl-1,1a,5,5a-tetrahydro-3-thia-cyclopropa[a]pentalen-4-yl)-propenyl]-phenyl}-acrylic acid (106 mg, 0.261 mmol) in ethanol (10 mL) and DIPEA (90 µL), Pd/C (50 mg, 10% Pd, moistened with 50% water) is added and the mixture is stirred at rt under 10 bar of H$_2$ overnight. The catalyst is filtered off and the filtrate is evaporated. The crude product is purified by prep. HPLC (Grom-Sil 120 ODS-4-HE, 30×75 mm, 10 µm, acetonitrile/water (0.5% HCOOH), 20% to 95% acetonitrile) to give 3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenyl}-propionic acid (69 mg) as a colourless oil; LC-MS: t$_R$=1.11 min, [M+1]$^+$=411.26; $^1$H NMR (CDCl$_3$): δ 6.84 (s, 2H9, 3.02-2.83 (m, 7H), 2.80 (d, J=18.8 Hz, 1H), 2.53-2.46 (m, 2H), 2.38 (s, 3H), 2.32 (s, 6H), 1.91-1.88 (m, 2H), 1.11 (s, 3H), 0.71 8s, 3H).

Example 236

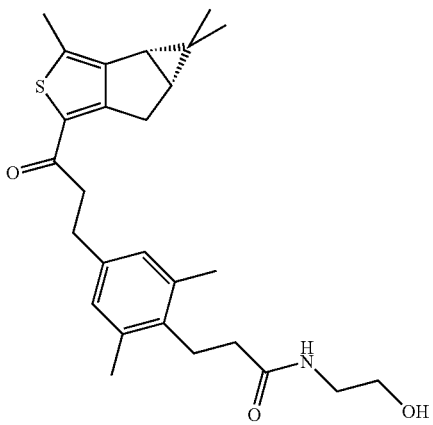

To a solution of 3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenyl}-propionic acid (10 mg, 22 µmol) in DMF (0.5 mL), TBTU (8 mg, 24 µmol) and DIPEA (10 mg, 72.6 µmol) is added. The mixture is stirred at rt for 5 min before ethanolamine (7 mg, 110 µmol) is added. Stirring is continued for 16 h at rt. The mixture is diluted with acetonitril (0.5 mL) and formic acid (25 µL) and separated by prep. HPLC (Waters SymmetryC18 19×50 mm 5 µm, 80% to 0% water (0.5% HCOOH) in acetonitrile) to give 3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenyl}-N-(2-hydroxy-ethyl)-propionamide (7 mg) as a colourless resin; LC-MS: $t_R$=1.03 min, $[M+1]^+$=454.35.

Example 237

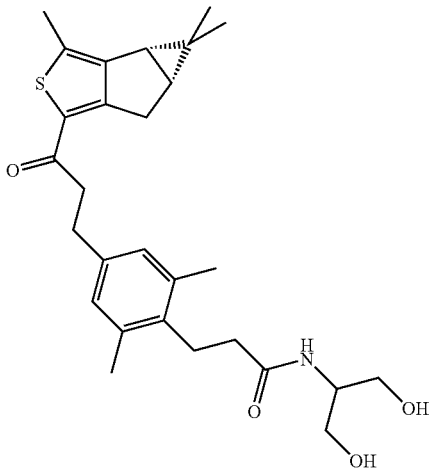

3-{2,6-Dimethyl-4-[3-oxo-3-((1aS,5aR)-1,1,2-trimethyl-1,1a,5,5a-tetrahydro-3-thia-cyclopropa[a]pentalen-4-yl)-propyl]-phenyl}-N-(2-hydroxy-1-hydroxymethyl-ethyl)-propionamide is prepared in analogy to Example 236 using serinol instead of ethanolamine; LC-MS: $t_R$=0.98 min, $[M+1]^+$=484.42.

Example 238

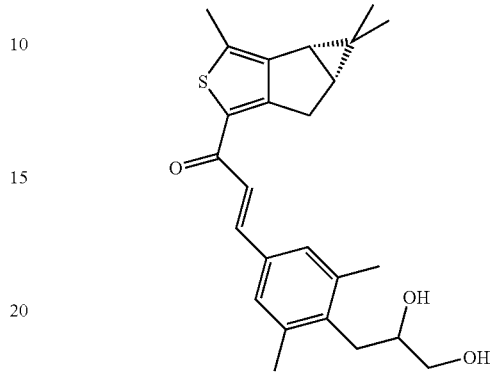

a) A solution of 2,5-dibromoxylene (8.0 g, 30.3 mmol) in diethyl ether (120 mL) is cooled to −78° C. and then treated with n-buthyllithium (20 mL, 1.6 M in hexane). After stirring for 40 min, DMF (6 mL) is slowly added. The mixture is warmed to rt and stirred for 1 h. The mixture is cooled again to −78° C. before another portion of n-butyllithium (5 mL) is added. The reaction mixture is allowed to warm to rt and stirred for another hour. The reaction is quenched by adding 5% aq. HCl. The mixture is extracted with EA, and the extract is concentrated in vacuo. The crude product is purified by CC on silica gel eluting with heptane:EA 5:1 to give 4-bromo-3,5-dimethyl-benzaldehyde (8.2 g) as a white soft solid.

b) A solution of 4-bromo-3,5-dimethyl-benzaldehyde (8.15 g, 38.25 mmol), p-toluenesulfonic acid (50 mg) and 1,3-propanediol (9.5 mL) in toluene (100 mL) is heated to 110° C. for 3 h. The reaction flask is equipped with a Dean-Stark apparatus and heating is continued at 110° C. for 16 h. The reaction mixture is cooled to rt, washed with sat. aq. NaHCO₃ and the solvent is removed in vacuo. The crude product is purified by CC on silica gel eluting with heptane:EA 9:1 to give 2-(4-bromo-3,5-dimethyl-phenyl)-[1,3]dioxane (5.97 g) as a colourless oil.

c) The corresponding Grignard-reagent is prepared form 2-(4-bromo-3,5-dimethyl-phenyl)-[1,3]dioxane (2.5 g, 9.22 mmol) and Mg (258 mg, 10.6 mmol) in THF (50 mL). To this reagent allylbromide (1.23 g, 10.14 mmol) is added dropwise at rt. The reaction mixture becomes warm (40° C.) and it is stirred for 16 h. The reaction is quenched by adding water. The mixture is extracted with EA. The organic extract is dried over MgSO₄, filtered and concentrated. The crude product is purified by CC on silica gel eluting with heptane:EA 10:1 to give 2-(4-allyl-3,5-dimethyl-phenyl)-[1,3]dioxane (1.8 g) as a colourless oil; LC-MS: $t_R$=1.02 min, $[M+1]^+$=233.22, ¹H NMR (CDCl₃): δ 7.12 (s, 2H), 5.94-5.80(m, 1H), 5.44 s 1H), 4.95 (dd, J=1.8, 10.0 Hz, 1H), 4.80 (dd, J=1.8, 17.0 Hz, 1H), 4.30-4.21 (m, 2H), 4.04-3.92 (m, 2H), 3.40-3.34 (m, 2H), 2.32-2.26 (m, 8H).

d) A solution of 2-(4-allyl-3,5-dimethyl-phenyl)-[1,3]dioxane (790 mg, 3.4 mmol) in acetone (10 mL) is treated with OsO₄ (1 mL of a 2.5% solution in tert. butanol), NMO hydrate (551 mg, 4.08 mmol) and water (0.5 mL). The mixture is stirred at rt for 2.5 h before it is diluted with DCM, washed with 10% aq. citric acid solution (2×50 mL), dried over MgSO₄, filtered and evaporated. The product is crystallized from DCM/heptane to give 3-(4-[1,3]dioxan-2-yl-2,6-dimethyl-phenyl)-propane-1,2-diol (335 mg) as a grey powder; ¹H NMR (CDCl₃): δ 7.15 (s, 2H), 5.42 8s, 1H), 4.26 (dd, J=4.6, 10.6 Hz, 2H), 3.98 (dt, $J_d$=1.8 Hz, $J_t$=12.3 Hz, 2H), 3.92-3.81 (m, 2H), 3.66 (dd, J=2.9, 11.1 Hz, 1H), 3.55 (dd, J=7.0 11.1 Hz, 1H), 2.88 (dd, J=8.8, 14.1 Hz, 1H), 2.74 (dd, J=5.3, 13.5 Hz, 1H), 2.34 (s, 6H), 2.30-2.14 (m, 2H), 1.90 (s br, 2H).

e) A solution of 1-((1aS,5aR)-1,1,2-trimethyl-1,1a,5,5a-tetrahydro-3-thia-cyclopropa[a]pentalen-4-yl)-ethanone (220 mg, 1.0 mmol) and 3-(4-[1,3]dioxan-2-yl-2,6-dimethyl-phenyl)-propane-1,2-diol (300 mg, 1.25 mmol) in ethanol (2 mL) and 5 N HCl in isopropanol (1 mL) is stirred at rt overnight. The reaction mixture is diluted with DCM and washed with water. The organic extract is dried over MgSO₄, filtered and evaporated. The crude product is purified by CC on silica gel eluting with EA to give 3-[4-(2,3-dihydroxy-propyl)-3,5-dimethyl-phenyl]-1-((1aS,5aR)-1,1,2-trimethyl-1,1a,5,5a-tetrahydro-3-thia-cyclopropa[a]pentalen-4-yl)-propenone (265 mg) as yellow crystals; LC-MS: $t_R$=1.05 min, [M+1]⁺=411.24

Example 239

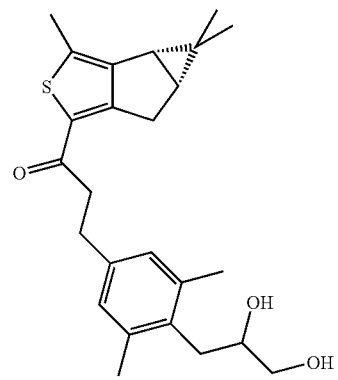

To a solution of 3-[4-(2,3-dihydroxy-propyl)-3,5-dimethyl-phenyl]-1-((1aS,5aR)-1,1,2-trimethyl-1,1a,5,5a-tetrahydro-3-thia-cyclopropa[a]pentalen-4-yl)-propenone (260 mg, 0.63 mmol) in ethanol (5 mL) and THF (5 mL), Pd/C (80 mg, 10% Pd) is added. The mixture is stirred at rt under 1.8 bar of H₂ for 18 h before it is filtered and concentrated. The crude product is purified by CC on silica gel eluting with EA:heptane 4:1 to give 3-[4-(2,3-dihydroxy-propyl)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one (220 mg) as a colourless solid; LC-MS: $t_R$=1.03 min, [M+1]⁺=413.28.

Example 240

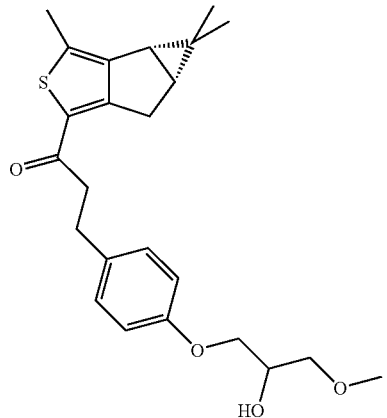

3-[4-(2-Hydroxy-3-methoxy-propoxy)-phenyl]-1-((1aS,5aR)-1,1,2-trimethyl-1,1a,5,5a-tetrahydro-3-thia-cyclopropa[a]pentalen-4-yl)-propan-1-one is prepared in analogy to Example 99; LC-MS: $t_R$=1.07 min, [M+1]⁺=415.18.

Examples 241 to 247

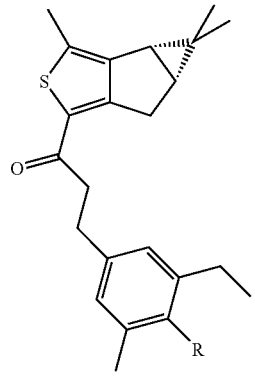

The following examples are prepared in analogy to previous examples:

| Example | R | prepared in analogy to Example | LC-MS $t_R$ (min) | [M + H]⁺ |
|---|---|---|---|---|
| 241 | 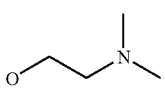 | 69 | 0.95 | 440.44 |

| Example | R | prepared in analogy to Example | LC-MS $t_R$ (min) | [M + H]+ |
|---|---|---|---|---|
| 242 | 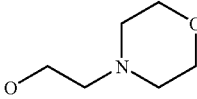 | 76 | 0.96 | 482.43 |
| 243 | 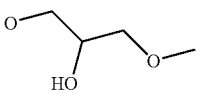 | 233 | 1.13 | 457.45 |
| 244 | 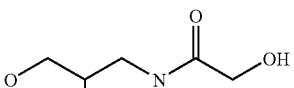 | 232 | 1.00 | 500.20 |
| 245 | 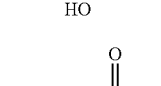 | 235 | 1.12 | 425.37 |
| 246 | 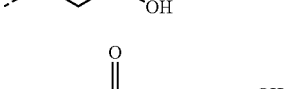 | 236 | 1.06 | 468.44 |
| 247 | 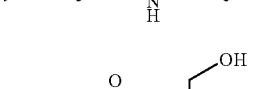 | 237 | 1.00 | 498.38 |
Example 245
$^1$H NMR (CDCl$_3$): δ 6.91 (s, 1H), 6.88 (s, 1H), 3.02-2.91 (m, 7H), 2.79 (d, J=18.8 Hz, 1H), 2.64 (q, J=7.0 Hz, 2H), 2.55-2.47 (m, 2H), 2.38 (s, 3H), 2.32 (s, 3H), 1.90-1.87 (m, 2H), 1.22 (t, J=7.0 Hz, 3H), 1.11 (s, 3H), 0.71 (s, 3H).
Example 248
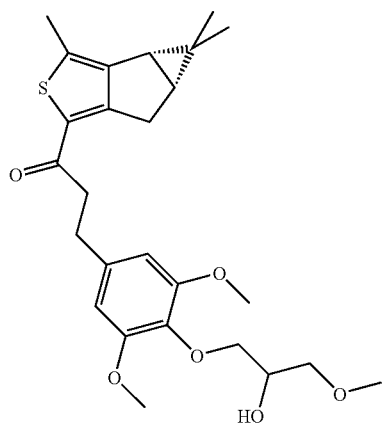
3-[4-(2-Hydroxy-3-methoxy-propoxy)-3,5-dimethoxy-phenyl]-1-((1aS,5aR)-1,1,2-trimethyl-1,1a,5,5a-tetrahydro-3-thia-cyclopropa[a]pentalen-4-yl)-propan-1-one is prepared in analogy to Example 99; LC-MS: $t_R$=1.06 min, [M+1]+=475.18.
Examples 249 to 252
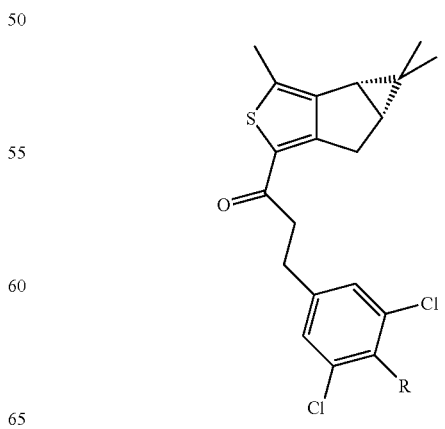

The following examples are prepared in analogy to previous examples:

| Example | R | prepared in analogy to Example | LC-MS $t_R$ (min) | $[M + H]^+$ |
|---|---|---|---|---|
| 249 | (dimethylaminoethoxy) | 69 | 0.95 | 466.27 |
| 250 | (pyrrolidinylethoxy) | 75 | 0.97 | 492.34 |
| 251 | (morpholinylethoxy) | 76 | 0.95 | 508.33 |
| 252 | (2-hydroxy-3-methoxypropoxy) | 233 | 1.13 | 483.28 |

Example 253

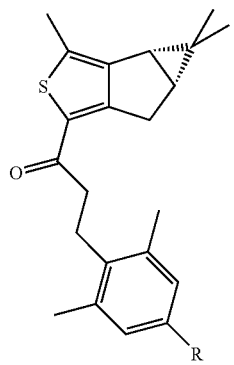

The following example is prepared in analogy to previous example:

| Example | R | prepared in analogy to Example | LC-MS $t_R$ (min) | $[M + H]^+$ |
|---|---|---|---|---|
| 253 | (2-hydroxy-3-methoxypropoxy) | 233 | 1.11 | 443.32 |

Example 254

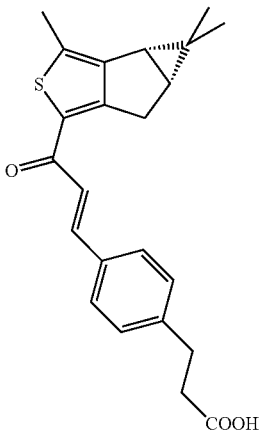

a) To a solution of 3-(4-formyl-phenyl)-acrylic acid (2.8 g, 16 mmol) in ethanol (120 mL) and DIPEA (3 mL), Pd/C (350 mg, 10% Pd) is added and the mixture is stirred at rt for 2 h under 1 atm of $H_2$. The mixture is filtered through celite and the filtrate is evaporated to leave 3-(4-hydroxymethyl-phenyl)-propionic acid (2.18 g) as a colourless oil; $^1$H NMR ($D_6$-DMSO): δ 12.1 (s br, 1H), 7.22-7.10 (m, 4H), 5.06 (t, J=5.3 Hz, 1H), 4.42 (d, J=5.3 Hz, 2H), 2.76 (t, J=7.6 Hz, 2H), 2.52-2.46 (m, 2H+solvent).

b) To a solution of 3-(4-hydroxymethyl-phenyl)-propionic acid (720 mg, 4 mmol) in ethanol (20 mL), $MnO_2$ (350 mg, 4 mmol) is added and the resulting suspension is stirred at 80° C. for 16 h before another portion of $MnO_4$ (500 mg, 5.7 mmol) is added. Stirring is continued at 80° C. for 2 days. The mixture is filtered through celite and the solvent of the filtrate is evaporated to afford crude 3-(4-formyl-phenyl)-propionic acid (500 mg) as a yellow oil; LC-MS: $t_R$=0.72 min.

c) A solution of 1-((1aS,5aR)-1,1,2-trimethyl-1,1a,5,5a-tetrahydro-3-thia-cyclopropa[a]pentalen-4-yl)-ethanone (176 mg, 0.8 mmol), 3-(4-formyl-phenyl)-propionic acid (142 mg, 0.8 mmol) and NaOH (2.24 g, 56 mmol) in methanol (20 mL) is stirred at 70° C. for 1 h. The mixture is diluted with water (400 mL) and the pH is adjusted to pH 2 by adding 2 N aq. HCl. The solution is extracted twice with DCM and the combined organic extracts are dried over $Na_2SO_4$, filtered and concentrated. The crude product is purified by prep. HPLC (Waters Xterra MS18 30×75 mm, 10 µm, 90% to 5% water containing 0.5% formic acid in acetonitrile) to give 3-{4-[3-oxo-3-((1aS,5aR)-1,1,2-trimethyl-1,1a,5,5a-tetrahydro-3-thia-cyclopropa[a]pentalen-4-yl)-propenyl]-phenyl}-propionic acid (125 mg) as a yellow resin; LC-MS: $t_R$=1.07 min, $[M+1]^+$=381.18.

Examples 255 to 259

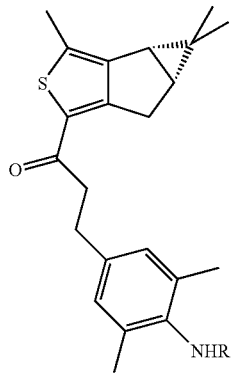

To a solution of 3-(4-amino-3,5-dimethyl-phenyl)-1-((1aS,5aR)-1,1,2-trimethyl-1,1a,5,5a-tetrahydro-3-thia-cyclopropa[a]pentalen-4-yl)-propan-1-one (7 mg, 0.02 mmol, Example 216) and the appropriate alkylating agent (5 eq.) in DMF (0.5 mL), NaHCO$_3$ (25 mg) and NaI (5 mg) is added. The mixture is stirred at 120° C. for 3 h, cooled to rt, diluted with acetic acid (0.2 mL) and separated by prep. HPLC (Waters Symmetry C18 19×50 mm 5 μm, 10 to 95% acetonitril in water containing 0.5% formic acid) to give the desired products as colourless to pale yellow resins.

| | | LC-MS | |
|---|---|---|---|
| Example | R | $t_R$ (min) | $[M + H]^+$ |
| 255 | ~~~\ | 0.85 | 382.39 |
| 256 | ~~~/ | 0.89 | 396.38 |
| 257 | ~~~OH | 0.83 | 398.41 |
| 258 | ~~~~OH | 0.83 | 412.42 |
| 259 | ~~~COOCH$_3$ | 1.27 | 426.37 |

Example 260

GTPγS Assay to Determine EC$_{50}$ Values

GTPγS binding assays are performed in 96 well microtiter plates (Nunc, 442587) in a final volume of 200 μl, using membrane preparations of CHO cells expressing recombinant human S1P1 receptor. Assay conditions are 20 mM Hepes (Fluka, 54461), 100 mM NaCl (Fluka, 71378), 5 mM MgCl$_2$ (Fluka, 63064), 0.1% BSA (Calbiochem, 126609), 1 μM GDP (Sigma, G-7127), 2.5% DMSO (Fluka, 41644), 50 μM $^{35}$S-GTPγS (Amersham Biosciences, SJ1320). The pH is 7.4. Test compounds are dissolved and diluted in 100% DMSO and pre-incubated at room temperature for 30 min in 150 μl of the above assay buffer, in the absence of $^{35}$S-GTPγS. After addition of 50 μl of $^{35}$S-GTPγS, the assay is incubated for 1 h at room temperature. The assay is terminated by transfer of the reaction mixture to a Multiscreen plate (Millipore, MAHFC1H60) using a cell harvester from Packard Biosciences, and the plates are washed with ice-cold 10 mM Na$_2$HPO$_4$/NaH$_2$PO$_4$ (70%/30%), dried, sealed at the bottom and, after addition of 25 μl MicroScint20 (Packard Biosciences, order#6013621), sealed on the top. Membrane-bound $^{35}$S-GTPγS is measured with a TopCount from Packard Biosciences.

EC$_{50}$ is the concentration of agonist inducing 50% of the maximal specific $^{35}$S-GTPγS binding. Specific binding is determined by subtracting non-specific binding from maximal binding. Maximal binding is the amount of cpm bound to the Multiscreen plate in the presence of 10 μM of S1P. Non-specific binding is the amount of binding in the absence of an agonist in the assay.

Table 1 shows the EC$_{50}$ value of some compounds of the present invention. The EC$_{50}$ values were determined according to the method described above.

TABLE 1

| Compound of Example | EC$_{50}$ [nM] |
|---|---|
| 1 | 12 |
| 2 | 3 |
| 13 | 13 |
| 31 | 6 |
| 37 | 58 |
| 48 | 2 |
| 60 | 1.4 |
| 64 | 4 |
| 96 | 1.0 |
| 99 | 1.1 |
| 149 | 2 |
| 175 | 28 |
| 233 | 2.3 |
| 234 | 2.7 |
| 237 | 2.9 |
| 239 | 0.8 |
| 244 | 1.1 |

Example 261

Assessment of In Vivo Efficacy

The efficacy of the compounds of Formula (I) is assessed by measuring the circulating lymphocytes after oral administration of 3 to 30 mg/kg of a compound of Formula (I) to normotensive male Wistar rats. The animals are housed in climate-controlled conditions with a 12 h-light/dark cycle, and have free access to normal rat chow and drinking water. Blood is collected before and 3, 6 and 24 h after drug administration. Full blood is subjected to hematology using Advia Hematology system (Bayer Diagnostics, Zürich, Switzerland).

All data are presented as mean±SEM. Statistical analyses are performed by analysis of variance (ANOVA) using Statistica (StatSoft) and the Student-Newman-Keuls procedure for multiple comparisons. The null hypothesis is rejected when $p<0.05$.

As an example, Table 2 shows the effect on lymphocyte counts 6 h after oral administration of 10 mg/kg of three compounds of the present invention to normotensive male Wistar rats as compared to a group of animals treated with vehicle only.

TABLE 2

| Compound of Example | Lymphocyte counts |
|---|---|
| 71 | −68% |
| 82 | −59% |
| 107 | −59% |

The invention claimed is:

1. A compound selected from the group consisting of thiophenes of the Formula (I)

Formula (I)

wherein

A represents —CH$_2$CH$_2$—, —CH=CH—, —NH—CH$_2$—, —CH$_2$—O—, or —CH$_2$—NH—;

R$^1$ represents hydrogen, C$_{1-5}$-alkyl, C$_{1-5}$-alkoxy, or halogen;

R$^2$ represents hydrogen, C$_{1-5}$-alkyl, C$_{1-5}$-alkoxy, trifluoromethyl, trifluoromethoxy, or halogen;

R$^3$ represents 2,3-dihydroxypropyl, —CH$_2$—(CH$_2$)$_k$—NR$^{31}$R$^{32}$, (azetidine-3-carboxylic acid)-1-yl-methyl, (azetidine-3-carboxylic acid C$_{1-5}$-alkylester)-1-yl-methyl, 2-[(azetidine-3-carboxylic acid)-1-yl]-ethyl, 2-[(azetidine-3-carboxylic acid C$_{1-5}$-alkylester)-1-yl]-ethyl, 3-[(azetidine-3-carboxylic acid)-1-yl]-propyl, 3-[(azetidine-3-carboxylic acid C$_{1-5}$-alkylester)-1-yl]-propyl, (pyrrolidine-3-carboxylic acid)-1-yl-methyl, (pyrrolidine-3-carboxylic acid C$_{1-5}$-alkylester)-1-yl-methyl, (pyrrolidine-2-carboxylic acid)-1-yl-methyl, (pyrrolidine-2-carboxylic acid C$_{1-5}$-alkylester)-1-yl-methyl, 2-[(pyrrolidine-3-carboxylic acid)-1-yl]-ethyl, 2-[(pyrrolidine-3-carboxylic acid C$_{1-5}$-alkylester)-1-yl]-ethyl, 2-[(pyrrolidine-2-carboxylic acid)-1-yl]-ethyl, 2-[(pyrrolidine-2-carboxylic acid C$_{1-5}$-alkylester)-1-yl]-ethyl, 3-[(pyrrolidine-3-carboxylic acid)-1-yl]-propyl, 3-[(pyrrolidine-3-carboxylic acid C$_{1-5}$-alkylester)-1-yl]-propyl, 3-[(pyrrolidine-2-carboxylic acid)-1-yl]-propyl, 3-[(pyrrolidine-2-carboxylic acid C$_{1-5}$-alkylester)-1-yl]-propyl, —CH$_2$—(CH$_2$)$_n$—COOH, —CH$_2$—(CH$_2$)$_n$—CONR$^{31}$R$^{32}$, —CO—NHR$^{31}$, 1-(1-(3-carboxy-azetidinyl))-2-acetyl, 1-(1-(2-carboxy-pyrrolidinyl))-2-acetyl, 1-(1-(3-carboxy-pyrrolidinyl))-2-acetyl, 1-(1-(3-carboxy-azetidinyl))-3-propionyl, 1-(1-(2-carboxy-pyrrolidinyl))-3-propionyl, 1-(1-(3-carboxy-pyrrolidinyl))-3-propionyl, —(CH$_2$)$_n$CH(OH)—CH$_2$—NR$^{31}$R$^{32}$, 2-hydroxy-3-methoxypropoxy, —OCH$_2$—(CH$_2$)$_m$—NR$^{31}$R$^{32}$, 2-pyrrolidin-1-yl-ethoxy, 3-pyrrolidin-1-yl-propoxy, 2-piperazin-1-yl-ethoxy, 2-[4-(C$_{1-5}$-alkyl)-piperazin-1-yl]-ethoxy, 2-[4-(2-hydroxy-ethyl)-piperazin-1-yl]-ethoxy, 3-piperazin-1-yl-propoxy, 3-[4-(C$_{1-5}$-alkyl)-piperazin-1-yl]-propoxy, 3-[4-(2-hydroxy-ethyl)-piperazin-1-yl]-propoxy, 2-morpholin-4-yl-ethoxy, 3-morpholin-4-yl-propoxy, 2-[(azetidine-3-carboxylic acid)-1-yl]-ethoxy, 2-[(azetidine-3-carboxylic acid C$_{1-5}$-alkylester)-1-yl]-ethoxy, 2-[(pyrrolidine-3-carboxylic acid)-1-yl]-ethoxy, 2-[(pyrrolidine-3-carboxylic acid C$_{1-5}$-alkylester)-1-yl]-ethoxy, 2-[(pyrrolidine-2-carboxylic acid)-1-yl]-ethoxy, 2-[(pyrrolidine-2-carboxylic acid C$_{1-5}$-alkylester)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid C$_{1-5}$-alkylester)-1-yl]-propoxy, 3-[(pyrrolidine-3-carboxylic acid)-1-yl]-propoxy, 3-[(pyrrolidine-3-carboxylic acid C$_{1-5}$-alkylester)-1-yl]-propoxy, 3-[(pyrrolidine-2-carboxylic acid)-1-yl]-propoxy, 3-[(pyrrolidine-2-carboxylic acid C$_{1-5}$-alkylester)-1-yl]-propoxy, 3-[(2-hydroxy-pyrrolidine)-1-yl]-propoxy, 3-[(3-hydroxy-pyrrolidine)-1-yl]-propoxy, —O—CH$_2$—CONR$^{31}$R$^{32}$, 1-(1-(3-carboxy-azetidinyl))-1-oxo-2-ethoxy, 1-(1-(pyrrolidine-2-carboxylic acid)-1-yl)-1-oxo-2-ethoxy, 1-(1-(pyrrolidine-3-carboxylic acid)-1-yl)-1-oxo-2-ethoxy, 3-carbamoyl-propoxy, 3-(C$_{1-5}$-alkylcarbamoyl)propoxy, 3-(2-hydroxyethylcarbamoyl)propoxy, —OCH$_2$—CH(OH)—CH$_2$—NR$^{31}$R$^{32}$, 3-[(azetidine-3-carboxylic acid)-1-yl]-2-hydroxypropoxy, 3-[(azetidine-3-carboxylic acid C$_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid C$_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid C$_{1-5}$-alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-(C$_{1-5}$-alkyl)-piperazin-1-yl]propoxy, 2-hydroxy-3-[4-(2-hydroxy-ethyl)-piperazin-1-yl]-propoxy, 2-hydroxy-3-morpholin-4-yl-propoxy, —NR$^{31}$R$^{32}$, —NHCO—R$^{31}$, —CH$_2$—(CH$_2$)$_k$—NHSO$_2$R$^{33}$, —(CH$_2$)$_n$CH(OH)—CH$_2$—NHSO$_2$R$^{33}$, —OCH$_2$—(CH$_2$)$_m$—NHSO$_2$R$^{33}$, —OCH$_2$—CH(OH)—CH$_2$—NHSO$_2$R$^{33}$, —CH$_2$—(CH$_2$)$_k$—NHCOR$^{34}$, —(CH$_2$)$_n$CH(OH)—CH$_2$—NHCOR$^{34}$, —OCH$_2$—(CH$_2$)$_m$—NHCOR$^{34}$, or —OCH$_2$—CH(OH)—CH$_2$—NHCOR$^{34}$;

R$^{31}$ represents hydrogen, methyl, ethyl, n-propyl, isopropyl, 2-hydroxyethyl, 2-hydroxy-1-hydroxymethyl-ethyl, 2-C$_{1-5}$-alkoxyethyl, 3-hydroxypropyl, 3-C$_{1-5}$-alkoxypropyl, 2-aminoethyl, 2-(C$_{1-5}$-alkylamino)ethyl, 2-(di-(C$_{1-5}$-alkyl)amino)ethyl, carboxymethyl, C$_{1-5}$-alkylcarboxymethyl, 2-carboxyethyl, or 2-(C$_{1-5}$-alkylcarboxy)ethyl;

R$^{32}$ represents hydrogen, methyl, or ethyl;

R$^{33}$ represents methyl, ethyl, propyl, isopropyl, butyl, 2-hydroxyethyl, 2-methoxyethyl, methylamino, ethylamino, propylamino, isopropylamino, n-butylamino, or dimethylamino;

R$^{34}$ represents hydroxymethyl, hydroxyethyl, aminomethyl, methylaminomethyl, dimethylaminomethyl, aminoethyl, 2-methylamino-ethyl, or 2-dimethylamino-ethyl;

k represents the integer 1, 2, or 3;

m represents the integer 1 or 2;

n represents 0, 1, or 2; and

R⁴ represents hydrogen, C$_{1-5}$-alkyl, methoxy or halogen,
or an optically pure enantiomer, a mixture of enantiomers, a diastereomer, a mixture of diastereomers, a diastereomeric racemate, or a mixture of diastereomeric racemates, or a salt, a solvent complex, or a morphological form, of said compound.

2. The compound according to claim 1, wherein R³ represents 2,3-dihydroxypropyl, —CH$_2$—(CH$_2$)$_k$—NR$^{31}$R$^{32}$, (azetidine-3-carboxylic acid)-1-yl-methyl, (azetidine-3-carboxylic acid C$_{1-5}$-alkylester)-1-yl-methyl, 2-[(azetidine-3-carboxylic acid)-1-yl]-ethyl, 2-[(azetidine-3-carboxylic acid C$_{1-5}$-alkylester)-1-yl]-ethyl, 3-[(azetidine-3-carboxylic acid)-1-yl]-propyl, 3-[(azetidine-3-carboxylic acid C$_{1-5}$-alkylester)-1-yl]-propyl, (pyrrolidine-3-carboxylic acid)-1-yl-methyl, (pyrrolidine-3-carboxylic acid C$_{1-5}$-alkylester)-1-yl-methyl, (pyrrolidine-2-carboxylic acid)-1-yl-methyl, (pyrrolidine-2-carboxylic acid C$_{1-5}$-alkylester)-1-yl-methyl, 2-[(pyrrolidine-3-carboxylic acid)-1-yl]-ethyl, 2-[(pyrrolidine-3-carboxylic acid C$_{1-5}$-alkylester)-1-yl]-ethyl, 2-[(pyrrolidine-2-carboxylic acid)-1-yl]-ethyl, 2-[(pyrrolidine-2-carboxylic acid C$_{1-5}$-alkylester)-1-yl]-ethyl, 3-[(pyrrolidine-3-carboxylic acid)-1-yl]-propyl, 3-[(pyrrolidine-3-carboxylic acid C$_{1-5}$-alkylester)-1-yl]-propyl, 3-[(pyrrolidine-2-carboxylic acid)-1-yl]-propyl, 3-[(pyrrolidine-2-carboxylic acid C$_{1-5}$-alkylester)-1-yl]-propyl, —CH$_2$—(CH$_2$)$_n$—CONR$^{31}$R$^{32}$, —CO—NHR$^{31}$, 1-(1-(3-carboxy-azetidinyl))-2-acetyl, 1-(1-(2-carboxy-pyrrolidinyl))-2-acetyl, 1-(1-(3-carboxy-pyrrolidinyl))-2-acetyl, 1-(1-(3-carboxy-azetidinyl))-3-propionyl, 1-(1-(2-carboxy-pyrrolidinyl))-3-propionyl, 1-(1-(3-carboxy-pyrrolidinyl))-3-propionyl, —(CH$_2$)$_n$CH(OH)—CH$_2$—NR$^{31}$R$^{32}$, 2-hydroxy-3-methoxy-propoxy, —OCH$_2$—(CH$_2$)$_m$—NR$^{31}$R$^{32}$, 2-pyrrolidin-1-yl-ethoxy, 3-pyrrolidin-1-yl-propoxy, 2-piperazin-1-yl-ethoxy, 2-[4-(C$_{1-5}$-alkyl)-piperazin-1-yl]-ethoxy, 2-[4-(2-hydroxy-ethyl)-piperazin-1-yl]-ethoxy, 3-piperazin-1-yl-propoxy, 3-[4-(C$_{1-5}$-alkyl)-piperazin-1-yl]-propoxy, 3-[4-(2-hydroxy-ethyl)-piperazin-1-yl]-propoxy, 2-morpholin-4-yl-ethoxy, 3-morpholin-4-yl-propoxy, 2-[(azetidine-3-carboxylic acid)-1-yl]-ethoxy, 2-[(azetidine-3-carboxylic acid C$_{1-5}$-alkylester)-1-yl]-ethoxy, 2-[(pyrrolidine-3-carboxylic acid)-1-yl]-ethoxy, 2-[(pyrrolidine-3-carboxylic acid C$_{1-5}$-alkylester)-1-yl]-ethoxy, 2-[(pyrrolidine-2-carboxylic acid)-1-yl]-ethoxy, 2-[(pyrrolidine-2-carboxylic acid C$_{1-5}$-alkylester)-1-yl] ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid C$_{1-5}$-alkylester)-1-yl]-propoxy, 3-[(pyrrolidine-3-carboxylic acid)-1-yl]-propoxy, 3-[(pyrrolidine-3-carboxylic acid C$_{1-5}$-alkylester)-1-yl]-propoxy, 3-[(pyrrolidine-2-carboxylic acid)-1-yl]-propoxy, 3-[(pyrrolidine-2-carboxylic acid C$_{1-5}$-alkylester)-1-yl]-propoxy, 3-[(2-hydroxy-pyrrolidine)-1-yl]-propoxy, 3-[(3-hydroxy-pyrrolidine)-1-yl]-propoxy, —O—CH$_2$—CONR$^{31}$R$^{32}$, 1-(1-(3-carboxy-azetidinyl))-1-oxo-2-ethoxy, 1-(1-(pyrrolidine-2-carboxylic acid)-1-yl)-1-oxo-2-ethoxy, 1-(1-(pyrrolidine-3-carboxylic acid)-1-yl)-1-oxo-2-ethoxy, 3-carbamoyl-propoxy, 3-(C$_{1-5}$-alkylcarbamoyl)propoxy, 3-(2-hydroxyethylcarbamoyl)propoxy, —OCH$_2$—CH(OH)—CH$_2$-NR$^{31}$R$^{32}$, 3-[(azetidine-3-carboxylic acid)-1-yl]-2-hydroxypropoxy, 3-[(azetidine-3-carboxylic acid C$_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid C$_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid C$_{1-5}$-alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-(C$_{1-5}$-alkyl)-piperazin-1-yl]-propoxy, 2-hydroxy-3-[4-(2-hydroxy-ethyl)-piperazin-1-yl]-propoxy, 2-hydroxy-3-morpholin-4-yl-propoxy, —NR$^{31}$R$^{32}$, —NHCO—R$^{31}$, —CH$_2$—(CH$_2$)$_k$—NHSO$_2$R$^{33}$, —(CH$_2$)$_n$CH(OH)—CH$_2$—NHSO$_2$R$^{33}$, —OCH$_2$—(CH$_2$)$_m$—NHSO$_2$R$^{33}$, —OCH$_2$—CH(OH)—CH$_2$—NHSO$_2$R$^{33}$, —CH$_2$—(CH$_2$)$_k$—NHCOR$^{34}$, —(CH$_2$)$_n$CH(OH)—CH$_2$—NHCOR$^{34}$, —OCH$_2$—(CH$_2$)$_m$—NHCOR$^{34}$, or —OCH$_2$—CH(OH)—CH$_2$—NHCOR$^{34}$, and R⁴ represents hydrogen, C$_{1-5}$-alkyl or halogen.

3. The compound according to claim 1, wherein the compound constitutes the (1aS,5aR)-isomer of the 1,1,2-trimethyl-1,1a,5,5a-tetrahydro-3-thia-cyclopropa pentalene derivative.

4. The compound according to claim 1, wherein A represents —CH$_2$—CH$_2$—.

5. The compound according to claim 1, wherein A represents —NH—CH$_2$—.

6. The compound according to claim 1, wherein A represents —CH$_2$—O—.

7. The compound according to claim 1, wherein R¹ represents hydrogen, and R² and R⁴ represent a methyl group.

8. The compound according to claim 1, wherein R⁴ is in the ortho-position with respect to R³.

9. The compound according to claim 1, wherein R¹ represents hydrogen, R² represents a methyl group, and R⁴ represents an ethyl group in the ortho-position with respect to R³.

10. The compound according to claim 1, wherein R¹ represents hydrogen, R² represents a methoxy group, and R⁴ represents chloro or fluoro both in the ortho-position with respect to R³.

11. The compound according to claim 1, wherein R¹ represents hydrogen, R² represents a methyl group and R⁴ represents chloro in the ortho-position with respect to R³.

12. The compound according to claim 1, wherein R³ represents 2,3-dihydroxypropyl, —CH$_2$—(CH$_2$)$_k$—NR$^{31}$R$^{32}$, (azetidine-3-carboxylic acid)-1-yl-methyl, (azetidine-3-carboxylic acid C$_{1-5}$-alkylester)-1-yl-methyl, 2-[(azetidine-3-carboxylic acid)-1-yl]-ethyl, 2-[(azetidine-3-carboxylic acid C$_{1-5}$-alkylester)-1-yl]-ethyl, 3-[(azetidine-3-carboxylic acid)-1-yl]-propyl, 3-[(azetidine-3-carboxylic acid C$_{1-5}$-alkylester)-1-yl]-propyl, (pyrrolidine-3-carboxylic acid)-1-yl-methyl, (pyrrolidine-3-carboxylic acid C$_{1-5}$-alkylester)-1-yl-methyl, (pyrrolidine-2-carboxylic acid)-1-yl-methyl, (pyrrolidine-2-carboxylic acid C$_{1-5}$-alkylester)-1-yl-methyl, 2-[(pyrrolidine-3-carboxylic acid)-1-yl]-ethyl, 2-[(pyrrolidine-3-carboxylic acid C$_{1-5}$-alkylester)-1-yl]-ethyl, 2-[(pyrrolidine-2-carboxylic acid)-1-yl]-ethyl, 2-[(pyrrolidine-2-carboxylic acid C$_{1-5}$-alkylester)-1-yl]ethyl, 3-[(pyrrolidine-3-carboxylic acid)-1-yl]-propyl, 3-[(pyrrolidine-3-carboxylic acid C$_{1-5}$-alkylester)-1-yl]-propyl, 3-[(pyrrolidine-2-carboxylic acid)-1-yl]-propyl, 3-[(pyrrolidine-2-carboxylic acid C$_{1-5}$-alkylester)-1-yl]-propyl, —CH$_2$—(CH$_2$)$_n$—COOH, —CH$_2$—(CH$_2$)$_n$—CONR$^{31}$R$^{32}$, —CO—NHR$^{31}$, or —(CH$_2$)$_n$CH(OH)—CH$_2$—NR$^{31}$R$^{32}$.

13. The compound according to claim 1, wherein R³ represents —OCH$_2$—(CH$_2$)$_m$—NR$^{31}$R$^{32}$, 2-pyrrolidin-1-yl-ethoxy, 3-pyrrolidin-1-yl-propoxy, 2-piperazin-1-yl-ethoxy, 2-[4-(C$_{1-5}$-alkyl)-piperazin-1-yl]ethoxy, 2-[4-(2-hydroxy-ethyl)-piperazin-1-yl]-ethoxy, 3-piperazin-1-yl-propoxy, 3-[4-(C$_{1-5}$-alkyl)-piperazin-1-yl]-propoxy, 3-[4-(2-hydroxy-ethyl)-piperazin-1-yl]-propoxy, 2-morpholin-4-yl-ethoxy, 3-morpholin-4-yl-propoxy, 2-[(azetidine-3-carboxylic acid)-1-yl]-ethoxy, 2-[(azetidine-3-carboxylic acid C$_{1-5}$-alkylester)-1-yl]ethoxy, 2-[(pyrrolidine-3-carboxylic acid)-1-yl]- ethoxy, 2-[(pyrrolidine-3-carboxylic acid $C_{1-5}$-alkylester)-1-yl]ethoxy, 2-[(pyrrolidine-2-carboxylic acid)-1-yl]-ethoxy, 2-[(pyrrolidine-2-carboxylic acid $C_{1-5}$-alkylester)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(azetidine-3-carboxylic acid $C_{1-5}$-alkylester)-1-yl]-propoxy, 3-[(pyrrolidine-3-carboxylic acid)-1-yl]-propoxy, 3-[(pyrrolidine-3-carboxylic acid $C_{1-5}$-alkylester)-1-yl]-propoxy, 3-[(pyrrolidine-2-carboxylic acid)-1-yl]-propoxy, 3-[(pyrrolidine-2-carboxylic acid $C_{1-5}$-alkylester)-1-yl]-propoxy, 3-[(2-hydroxy-pyrrolidine)-1-yl]-propoxy, 3-[(3-hydroxy-pyrrolidine)-1-yl]-propoxy, —O—CH$_2$—CONR$^{31}$R$^{32}$, 3-carbamoyl-propoxy, 3-($C_{1-5}$-alkylcarbamoyl)propoxy, 3-(2-hydroxyethylcarbamoyl)propoxy, —OCH$_2$—CH(OH)—CH$_2$—NR$^{31}$R$^{32}$, 3-[(azetidine-3-carboxylic acid)-1-yl]-2-hydroxypropoxy, 3-[(azetidine-3-carboxylic acid $C_{1-5}$-alkylester)-1-yl]-2-hydroxypropoxy, 2-hydroxy-3-[(pyrrolidine-3-carboxylic acid)-1-yl]-propoxy, 2-hydroxy-3-[(pyrrolidine-3-carboxylic acid $C_{1-5}$-alkylester)-1-yl]-propoxy, 2-hydroxy-3-[(pyrrolidine-2-carboxylic acid)-1-yl]-propoxy, 2-hydroxy-3-[(pyrrolidine-2-carboxylic acid $C_{1-5}$-alkylester)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, 2-hydroxy-3-[4-($C_{1-5}$-alkyl)piperazin-1-yl]-propoxy, 2-hydroxy-3-[4-(2-hydroxy-ethyl)-piperazin-1-yl]-propoxy, or 2-hydroxy-3-morpholin-4-yl-propoxy.

14. The compound according to claim 1, wherein $R^3$ represents —OCH$_2$—(CH$_2$)$_m$—NR$^{31}$R$^{32}$, —O—CH$_2$—CONR$^{31}$R$^{32}$, or —OCH$_2$—CH(OH)—CH$_2$—NR$^{31}$R$^{32}$, wherein $R^{31}$ represents methyl or 2-hydroxyethyl, and $R^{32}$ represents hydrogen.

15. The compound according to claim 1, wherein $R^3$ represents —OCH$_2$—(CH$_2$)$_m$—NR$^{31}$R$^{32}$, 2-[(azetidine-3-carboxylic acid)-1-yl]-ethoxy, 2-[(pyrrolidine-3-carboxylic acid)-1-yl]-ethoxy, 2-[(pyrrolidine-2-carboxylic acid)-1-yl]-ethoxy, 2-[(2-hydroxy-pyrrolidine)-1-yl]-ethoxy, 2-[(3-hydroxy-pyrrolidine)-1-yl]-ethoxy, 3-[(azetidine-3-carboxylic acid)-1-yl]-propoxy, 3-[(pyrrolidine-3-carboxylic acid)-1-yl]-propoxy, 3-[(pyrrolidine-2-carboxylic acid)-1-yl]-propoxy, 3-[(2-hydroxy-pyrrolidine)-1-yl]-propoxy, 3-[(3-hydroxy-pyrrolidine)-1-yl]-propoxy, —O—CH$_2$—CONR$^{31}$R$^{32}$, —OCH$_2$—CH(OH)—CH$_2$—NR$^{31}$R$^{32}$, 3-[(azetidine-3-carboxylic acid)-1-yl]-2-hydroxypropoxy, 2-hydroxy-3-[(pyrrolidine-3-carboxylic acid)-1-yl]-propoxy, 2-hydroxy-3-[(pyrrolidine-2-carboxylic acid)-1-yl]-propoxy, 2-hydroxy-3-[(2-hydroxy-pyrrolidine)-1-yl]-propoxy, 2-hydroxy-3-[(3-hydroxy-pyrrolidine)-1-yl]-propoxy, 2-hydroxy-3-pyrrolidin-1-yl-propoxy, 2-hydroxy-3-piperazin-1-yl-propoxy, or 2-hydroxy-3-[4-($C_{1-5}$-alkyl)-piperazin-1-yl]-propoxy.

16. The compound according to claim 1, wherein $R^3$ represents —CH$_2$—(CH$_2$)$_k$—NHSO$_2$R$^{33}$, —(CH$_2$)$_n$CH(OH)—CH$_2$—NHSO$_2$R$^{33}$, —OCH$_2$—(CH$_2$)$_m$—NHSO$_2$R$^{33}$, —OCH$_2$—CH(OH)—CH$_2$—NHSO$_2$R$^{33}$, —CH$_2$—(CH$_2$)$_k$—NHCOR$^{34}$, —(CH$_2$)$_n$CH(OH)—CH$_2$—NHCOR$^{34}$, —OCH$_2$—(CH$_2$)$_m$—NHCOR$^{34}$, or —OCH$_2$—CH(OH)—CH$_2$—NHCOR$^{34}$.

17. The compound according to claim 1 selected from the group consisting of:

3-[4-(3-amino-propyl)-phenyl]-1-((1aS,5aR)-1,1,2-trimethyl-1,1a,5,5a-tetrahydro-3-thia-cyclopropa[a]pentalen-4-yl)-propan-1-one;

3-[4-(3-methylamino-propyl)-phenyl]-1-((1aS,5aR)-1,1,2-trimethyl-1,1a,5,5a-tetrahydro-3-thia-cyclopropa[a]pentalen-4-yl)-propan-1-one;

3-{4-[3-(2-hydroxy-ethylamino)-propyl]-phenyl}-1-((1aS,5aR)-1,1,2-trimethyl-1,1a,5,5a-tetrahydro-3-thia-cyclopropa[a]pentalen-4-yl)-propan-1-one;

3-{4-[3-(2-hydroxy-1-hydroxymethyl-ethylamino)-propyl]-phenyl}-1-((1aS,5aR)-1,1,2-trimethyl-1,1a,5,5a-tetrahydro-3-thia-cyclopropa[a]pentalen-4-yl)-propan-1-one;

1-{4-[3-oxo-3-((1aS,5aR)-1,1,2-trimethyl-1,1a,5,5a-tetrahydro-3-thia-cyclopropa[a]pentalen-4-yl)-propyl]benzyl}-azetidine-3-carboxylic acid;

3-(2-hydroxy-3-{2-methyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-propylamino)-propionic acid;

3-[3-chloro-4-(2-hydroxy-3-methylamino-propoxy)-phenyl]-1-((1aS,5aR)-1,1,2-trimethyl-1,1a,5,5a-tetrahydro-3-thia-cyclopropa[a]pentalen-4-yl)-propan-1-one;

3-(3-{2-chloro-4-[3-oxo-3-((1aS,5aR)-1,1,2-trimethyl-1,1a,5,5a-tetrahydro-3-thia-cyclopropa[a]pentalen-4-yl)-propyl]-phenoxy}-2-hydroxy-propylamino)-propionic acid;

3-[3,5-dimethyl-4-(2-methylamino-ethoxy)-phenyl]-1-((1aS,5aR)-1,1,2-trimethyl-1,1a,5,5a-tetrahydro-3-thia-cyclopropa[a]pentalen-4-yl)-propan-1-one;

3-[4-(2-dimethylamino-ethoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one;

3-{4-[2-(2-hydroxy-ethylamino)-ethoxy]-3,5-dimethyl-phenyl}-1-((1aS,5aR)-1,1,2-trimethyl-1,1a,5,5a-tetrahydro-3-thia-cyclopropa[a]pentalen-4-yl)-propan-1-one;

3-{4-[2-(2-hydroxy-1-hydroxymethyl-ethylamino)-ethoxy]-3,5-dimethyl-phenyl}-1-((1aS,5aR)-1,1,2-trimethyl-1,1a,5,5a-tetrahydro-3-thia-cyclopropa[a]pentalen-4-yl)-propan-1-one;

3-[3,5-dimethyl-4-(2-pyrrolidin-1-yl-ethoxy)-phenyl]-1-((1aS,5aR)-1,1,2-trimethyl-1,1a,5,5a-tetrahydro-3-thia-cyclopropa[a]pentalen-4-yl)-propan-1-one;

1-(2-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-ethyl)-azetidine-3-carboxylic acid;

3-{4-[3-(2-hydroxy-ethylamino)-propoxy]-3,5-dimethyl-phenyl}-1-((1aS,5aR)-1,1,2-trimethyl-1,1a,5,5a-tetrahydro-3-thia-cyclopropa[a]pentalen-4-yl)-propan-1-one; (3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-propylamino)-acetic acid;

3-[4-(3-amino-2-hydroxy-propoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one;

3-[4-(2-hydroxy-3-methylamino-propoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one;

3-{4-[2-hydroxy-3-(2-hydroxy-ethylamino)-propoxy]-3,5-dimethyl-phenyl}-1-((1aS,5aR)-1,1,2-trimethyl-1,1a,5,5a-tetrahydro-3-thia-cyclopropa[a]pentalen-4-yl)-propan-1-one;

3-{4-[2-hydroxy-3-(2-hydroxy-1-hydroxymethyl-ethylamino)-propoxy]-3,5-dimethyl-phenyl}-1-((1aS,5aR)-1,1,2-trimethyl-1,1a,5,5a-tetrahydro-3-thia-cyclopropa[a]pentalen-4-yl)-propan-1-one;

(3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-2-hydroxy-propyl amino)-acetic acid;

1-(3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-2-hydroxy-propyl)-azetidine-3-carboxylic acid;

2-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-acetamide;

2-{2,6-dimethyl-4-[3-oxo-3-((1aS,5a,1,2-trimethyl-1,1a,5,5a-tetrahydro-3-thia-cyclopropa[a]pentalen-4-yl)-propyl]-phenoxy}-N-(2-hydroxy-ethyl)-acetamide;

3-{3-ethyl-4-[2-hydroxy-3-(2-hydroxy-ethylamino)-propoxy]-5-methyl-phenyl}-1-((1a R,5aS)-1,1,2-trimethyl-1,1a,5,5a-tetrahydro-3-thia-cyclopropa[a]pentalen-4-yl)-propan-1-one;

3-[3-chloro-5-methoxy-4-(2-methylamino-ethoxy)-phenyl]-1-((1aS,5aR)-1,1,2-trimethyl-1,1a,5,5a-tetrahydro-3-thia-cyclopropa[a]pentalen-4-yl)-propan-1-one;

3-[3-chloro-4-(2-dimethylamino-ethoxy)-5-methoxy-phenyl]-1-((1aS,5aR)-1,1,2-trimethyl-1,1a,5,5a-tetrahydro-3-thia-cyclopropa[a]pentalen-4-yl)-propan-1-one;

3-{3-chloro-4-[2-(2-hydroxy-ethylamino)-ethoxy]-5-methoxy-phenyl}-1-((1aS,5aR)-1,1,2-trimethyl-1,1a,5,5a-tetrahydro-3-thia-cyclopropa[a]pentalen-4-yl)-propan-1-one;

1-(2-{2-chloro-6-methoxy-4-[3-oxo-3-((1aS,5aR)-1,1,2-trimethyl-1,1a,5,5a-tetrahydro-3-thia-cyclopropa[a]pentalen-4-yl)-propyl]-phenoxy}-ethyl)-azetidine-3-carboxylic acid;

3-{3-chloro-4-[3-(2-hydroxy-ethylamino)-propoxy]-5-methoxy-phenyl}-1-((1aS,5aR)-1,1,2-trimethyl-1,1a,5,5a-tetrahydro-3-thia-cyclopropa[a]pentalen-4-yl)-propan-1-one;

3-{3-chloro-4-[2-hydroxy-3-(2-hydroxy-ethylamino)-propoxy]-5-methoxy-phenyl}1-1-((1aS,5aR)-1,1,2-trimethyl-1,1a,5,5a-tetrahydro-3-thia-cyclopropa[a]pentalen-4-yl)-propan-1-one;

3-(3-{2-chloro-6-methoxy-4-[3-oxo-3-((1aS,5aR)-1,1,2-trimethyl-1,1a,5,5a-tetrahydro-3-thia-cyclopropa[a]pentalen-4-yl)-propyl]-phenoxy}-2-hydroxy-propylamino)-propionic acid;

3-[3-chloro-4-(2-hydroxy-3-methoxy-propoxy)-5-methyl-phenyl]-1-((1aS,5aR)-1,1,2-trimethyl-1,1a,5,5a-tetrahydro-3-th ia-cyclopropa[a]pentalen-4-yl)-propan-1-one;

N-(2-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-ethyl)-methanesulfonamide;

ethanesulfonic acid (2-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-ethyl)-amide;

propane-1-sulfonic acid (2-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-ethyl)-amide;

N-(3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-propyl)-methanesulfonamide;

N-(3-{2,6-dimethyl-4-[3-oxo-34(1aS,5aR)-1,1,2-trimethyl-1,1a,5,5a-tetrahydro-3-thia-cyclopropa[a]pentalen-4-yl)-propyl]-phenoxy}-2-hydroxy-propyl)-methanesulfonamide;

ethanesulfonic acid (3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-2-hydroxy-propyl)-amide;

propane-1-sulfonic acid (3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-2-hydroxy-propyl)-amide;

N-(3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-2-hydroxy-propyl)-2-hydroxy-acetamiden; and N-(3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-propyl)-2-hydroxy-acetamide.

18. The compound according to claim 1 selected from the group consisting of:

3-[4-(2-hydroxy-3-methoxy-propoxy)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one;

2-amino-N-(3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-2-hydroxy-propyl)-acetamide;

3-{2,6-dimethyl-4-[3-oxo-3-((1aS,5aR)-1,1,2-trimethyl-1,1a,5,5a-tetrahydro-3-thia-cyclopropa[a]pentalen-4-yl)-propyl]-phenyl}-N-(2-hydroxy-1-hydroxymethyl-ethyl)-propionamide[H];

3-[4-(2,3-dihydroxy-propyl)-3,5-dimethyl-phenyl]-1-((1aR,5aS)-1,1,2-trimethyl-1,1a,5,5a-tetrahydro-3-thia-cyclopropa[a]pentalen-4-yl)-propan-1-one;

N-(3-{2-ethyl-6-methyl-4-[3-oxo-3-((1aS,5aR)-1,1,2-trimethyl-1,1a,5,5a-tetrahydro-3-thia-cyclopropa[a]pentalen-4-yl)-propyl]-phenoxy}-2-hydroxy-propyl)-2-hydroxy-acetamide;

3-{2-ethyl-6-methyl-4-[3-oxo-3-((1aS,5aR)-1,1,2-trimethyl-1,1a,5,5a-tetrahydro-3-thia-cyclopropa[a]pentalen-4-yl)-propyl]-phenyl}-N-(2-hydroxy-ethyl)-propionamide;

3-{2-ethyl-6-methyl-4-[3-oxo-3-((1aS,5aR)-1,1,2-trimethyl-1,1a,5,5a-tetrahydro-3-thia-cyclopropa[a]pentalen-4-yl)-propyl]-phenyl}-N-(2-hydroxy-1-hydroxymethyl-ethyl)-propionamide;

3-[3,5-dichloro-4-(2-hydroxy-3-methoxy-propoxy)-phenyl]-1-((1aS,5aR)-1,1,2-trimethyl-1,1a,5,5a-tetrahydro-3-thia-cyclopropa[a]pentalen-4-yl)-propan-1-one;

3-[4-(2-hydroxy-ethylamino)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one; and 3-[4-(3-hydroxy-propylamino)-3,5-dimethyl-phenyl]-1-((1aS,5aR)-1,1,2-trimethyl-1,1a,5,5a-tetrahydro-3-thia-cyclopropa[a]pentalen-4-yl)-propan-1-one.

19. A pharmaceutical composition comprising a compound according to claim 1 and a pharmaceutically acceptable carrier.

20. A method for preventing rejection of transplanted organs selected from kidney, liver, heart and lung comprising administering to a patient in need thereof a pharmaceutically active amount of the compound of claim 1.

21. A method for preparing a pharmaceutical composition, comprising mixing one or more compound(s) of claim 1 with an inert excipient.

22. A method for treating a disease or disorder selected from rheumatoid arthritis, multiple sclerosis, psoriasis, psoriatic arthritis, Crohn's disease, Hashimoto's thyroiditis; and atopic dermatitis, comprising administering to a patient in need thereof a pharmaceutically active amount of the compound of claim 1.

* * * * *